US010238677B2

(12) United States Patent
Von Geldern et al.

(10) Patent No.: US 10,238,677 B2
(45) Date of Patent: Mar. 26, 2019

(54) TREATMENT OF FILARIAL DISEASES

(71) Applicants: AbbVie Inc., North Chicago, IL (US); Liverpool School of Tropical Medicine, Liverpool (GB)

(72) Inventors: Thomas W. Von Geldern, North Chicago, IL (US); Dale J. Kempf, North Chicago, IL (US); Kennan C. Marsh, North Chicago, IL (US); Mark John Taylor, Liverpool (GB); Stephen Andrew Ward, Liverpool (GB); Louise Ford, Liverpool (GB); Joseph Turner, Liverpool (GB)

(73) Assignees: LIVERPOOL SCHOOL OF TROPICAL MEDICINE, Liverpool (GB); ABBVIE INC., North Chicago, IL (US)

( * ) Notice: Subject to any disclaimer, the term of this patent is extended or adjusted under 35 U.S.C. 154(b) by 0 days.

(21) Appl. No.: 15/542,208

(22) PCT Filed: Jan. 8, 2016

(86) PCT No.: PCT/US2016/012687
§ 371 (c)(1),
(2) Date: Jul. 7, 2017

(87) PCT Pub. No.: WO2016/112317
PCT Pub. Date: Jul. 14, 2016

(65) Prior Publication Data
US 2017/0368088 A1 Dec. 28, 2017

Related U.S. Application Data

(60) Provisional application No. 62/101,484, filed on Jan. 9, 2015.

(51) Int. Cl.
*A61K 31/365* (2006.01)
*A61K 31/7048* (2006.01)
*C07H 17/08* (2006.01)

(52) U.S. Cl.
CPC ........ *A61K 31/7048* (2013.01); *A61K 31/365* (2013.01); *C07H 17/08* (2013.01); *Y02A 50/421* (2018.01)

(58) Field of Classification Search
None
See application file for complete search history.

(56) References Cited

U.S. PATENT DOCUMENTS 4,436,733 A 3/1984 Kirst
10,072,040 B2 9/2018 von Geldern et al.

2009/0131343 A1 5/2009 Phan et al.
2011/0245191 A1 10/2011 Rosentel, Jr. et al.
2014/0243408 A1 8/2014 Conder et al.
2015/0259374 A1 9/2015 von Geldern et al.
2016/0200757 A1 7/2016 von Geldern et al.

FOREIGN PATENT DOCUMENTS

JP S5813595 A 1/1983
WO WO-2015138458 A1 9/2015

OTHER PUBLICATIONS

Ansel's Pharmaceutical Dosage Forms and Drug Delivery Systems, Allen L.V., ed., Lippincott Williams & Wilkins, 2005, 738 pages.
Ash L.R., et al., "Development of Subperiodic Brugia Malayi in the Jird, Meriones Unguiculatus, with Notes on Infections in Other Rodents," The Journal of Parasitology, Oct. 1970, vol. 56 (5), pp. 969-973.
Clare R.H., et al., "Development and Validation of a High-throughput Anti-wolbachia Whole-cell Screen: A Route to Macrofilaricidal Drugs Against Onchocerciasis and Lymphatic Filariasis," Journal of Biomolecular Screening, Jan. 2015, vol. 20 (1), pp. 64-69.
Furniss B.S., et al., Vogel's Textbook of Practical Organic Chemistry, 5th Edition, Longman Scientific & Technical, 1989, Essex CM20 2JE, England, Table of Contents.
Greene T.W., et al., Protective Groups in Organic Synthesis, 4th Edition, John Wiley and Sons, Inc., 2006, Table of Contents.
Halliday A., et al., "A Murine Macrofilaricide Pre-clinical Screening Model for Onchocerciasis and Lymphatic Filariasis," Parasites & Vectors, Oct. 24, 2014, vol. 7, p. 472.
Hoerauf A., et al., "Targeting of Wolbachia Endobacteria in Litomosoides Sigmodontis: Comparison of Tetracyclines with Chloramphenicol, Macrolides and Ciprofloxacin," Tropical Medicine & International Health, Apr. 2000, vol. 5 (4), pp. 275-279.
Hoerauf A., et al., "Tetracycline Therapy Targets Intracellular Bacteria in the Filarial Nematode Litomosoides Sigmodontis and Results in Filarial Infertility," The Journal of Clinical Investigation, Jan. 1999, vol. 103 (1), pp. 11-18.
Hoover J.E., Remington's Pharmaceutical Sciences, 15th Edition, 1975, Mack Publishing Co., Table of Contents.
International Search Report and Written Opinion for Application No. PCT/US2016/012687, dated Apr. 7, 2016, 7 pages.
IUPAC 1974 Recommendations for Section E, Fundamental Stereochemistry, Pure and Applied Chemistry, 1976, vol. 45, pp. 13-30.
Johnston K.L., et al., "Lipoprotein Biosynthesis as a Target for Anti-wolbachia Treatment of Filarial Nematodes," Parasites & Vectors, Oct. 14, 2010, vol. 3, p. 99.

(Continued)

*Primary Examiner* — Layla D Berry
(74) *Attorney, Agent, or Firm* — Neal, Gerber & Eisenberg LLP

(57) ABSTRACT

The present invention pertains to prevention of and/or treatment for filariasis. In particular, the present invention pertains to the use of tylosin A and its analogs and derivatives to prevent or treat filarial worm infection and/or diseases associated with filarial worm infection. The present invention also pertains to pharmaceutical compositions comprising tylosin A or an analog or derivative thereof for use in preventing or treating filarial worm infection and/or diseases associated with filarial worm infection.

28 Claims, No Drawings

(56) References Cited

OTHER PUBLICATIONS

Kiyoshima K., et al., "Application of Dibutyltin Oxide Method to Regioselective Acylation and Alkylation of Tylosin at C-4"., Chemical & Pharmaceutical Bulletin, Apr. 1989, vol. 37 (4), pp. 861-865.
McGarry H.F., et al., "Population Dynamics of Wolbachia Bacterial Endosymbionts in Brugia Malayi," Molecular and Biochemical Parasitology, May 2004, vol. 135 (1), pp. 57-67.
Narandja A., et al., "10,11,12,13-Tetrahydro Derivatives of Tylosin. Ii. Synthesis, Antibacterial Activity and Tissue of 4'-Deoxy-10,11,12,13-Tetrahydrodesmycosin.," The Journal of Antibiotics, 1995, vol. 48 (3), pp. 248-253.
O'Neill S.L., et al., "In Vitro Cultivation of Wolbachia Pipientis in an Aedes Albopictus Cell Line," Insect Molecular Biology, Feb. 1997, vol. 6 (1), pp. 33-39.
Orihel T.C., et al., "Loa Loa: Development and Course of Patency in Experimentally-infected Primates," Tropical Medicine and Parasitology, Dec. 1985, vol. 36 (4), pp. 215-224.
Osei-Atweneboana M.Y., et al., "Phenotypic Evidence of Emerging Ivermectin Resistance in Onchocerca Volvulus," PLoS Neglected Tropical Diseases, Mar. 29, 2011, vol. 5 (3), pp. e998.
Ottesen E.A., et al., "A Controlled Trial of Ivermectin and Diethylcarbamazine in Lymphatic Filarias," The New England Journal of Medicine, 1990, vol. 322 (16), pp. 1113-1117.
Taylor M.J., et al., "Anti-wolbachia Drug Discovery and Development: Safe Macrofilaricides for Onchocerciasis and Lymphatic Filariasis," Parasitology, Jan. 2014, vol. 141 (1), pp. 119-127.
Taylor M.J., et al., "Macrofilaricidal Activity After Doxycycline Treatment of Wuchereria Bancrofti: A Double-blind, Randomised Placebo-controlled Trial," Lancet, Jun. 18-24, 2005, vol. 365 (9477), pp. 2116-2221.
Townson S., et al., "Onchocerca Parasites and Wolbachia Endosymbionts: Evaluation of a Spectrum of Antibiotic Types for Activity Against Onchocerca Gutturosa in Vitro," Filaria Journal, Mar. 24, 2006, vol. 5, p. 4.
Tsuchiya M., et al., "Studies of Tylosin Derivatives Effective Against Macrolide-Resistant Strains: Synthesis and Structure-Activity Relationships," Journal of Antibiotics, Japan Antibiotics Research Association, Tokyo, JP, 1982, vol. 35 (6), pp. 661-671.
Turner J.D., et al., "Wolbachia Endosymbiotic Bacteria of Brugia Malayi Mediate Macrophage Tolerance to Tir- and Cd40-specific Stimuli in a Myd88/tlr2-dependent Manner," The Journal of Immunology, Jul. 15, 2006, vol. 177 (2), pp. 1240-1249.
Vijayasekaran, V. et al., "A study of low-dose ivermectin and diethyl carbamazine (DEC): a double-blind controlled clinical trial in lymphatic filariasis," European Journal of Pharmacology, 1990, vol. 183(5), pp. 1654-1655.
Bowman D.D., et al., "Macrocyclic Lactones and Dirofilaria Immitis Microfilariae," Topics in Companion Animal Medicine, Nov. 2011, vol. 26 (4), pp. 160-172.
Extended European Search Report for Application No. EP16735493 dated Jun. 29, 2018, 6 pages.
Hoerauf A., et al., "Effects of 6-week Azithromycin Treatment on the Wolbachia Endobacteria of Onchocerca Volvulus," Parasitology Research, Jul. 2008, vol. 103 (2), pp. 279-286.
Johnston K.L., et al., "Repurposing of Approved Drugs from the Human Pharmacopoeia to Target Wolbachia Endosymbionts of Onchocerciasis and Lymphatic Filariasis," International Journal for Parasitology—drugs and Drug Resistance, Dec. 2014, vol. 4 (3), pp. 278-286.

TREATMENT OF FILARIAL DISEASES

CROSS-REFERENCE TO RELATED APPLICATIONS

This application claims priority to U.S. Provisional Application No. 62/101,484 filed Jan. 9, 2015, the entire contents of which are incorporated herein by reference.

STATEMENT REGARDING FEDERALLY SPONSORED RESEARCH OR DEVELOPMENT

Not applicable.

JOINT RESEARCH AGREEMENT

Subject matter disclosed in this application was made by or on behalf of AbbVie Inc. and/or Liverpool School of Tropical Medicine, whom are parties to a joint research agreement that was in effect on or before the effective filing date of this application, and such subject matter was made as a result of activities undertaken within the scope of the joint research agreement.

TECHNICAL FIELD

The present invention relates to prevention of and/or treatment for filarial worm infections and diseases caused by filarial worm infection. The present invention relates to the use of tylosin A and its analogs and derivatives to prevent or treat filarial worm infection and/or diseases associated with filarial worm infection. The present invention also relates to pharmaceutical compositions comprising tylosin A or an analog or derivative thereof for use in preventing or treating filarial worm infection and/or diseases associated with filarial worm infection.

BACKGROUND

*Wolbachia* is a genus of bacteria that infects arthropods, including insects and crusteans, and filarial worms such as *Onchocerca volvulus*, *Wuchereria bancrofti*, *Brugia malayi*, and *Brugia timori*. The bacteria reside in cytoplasmic vacuoles and are essential for development, reproduction and long-term survival of filarial worms.

*Onchocerca volvulus* is a causative agent of onchocerciasis, or river blindness, in humans. Manifestations of onchocerciasis result primarily from the intense inflammatory reaction to *Wolbachia* bacteria released into the skin and eyes upon the death of microfilaria. Onchocerciasis affects up to 37 million people worldwide and is most abundant in Africa.

*Wuchereria bancrofti*, *Brugia malayi*, and *Brugia timori* are causative agents of lymphatic filariasis, or elephantiasis, in humans. People suffering with lymphatic filariasis can develop hydrocele and lymphedema leading to elephantiasis. It is estimated that up to 120 million people in 83 countries worldwide are affected by lymphatic filariasis.

Two of the major constraints of treatment of filarial diseases are (i) the absence of a macrofilaricidal drug (or for onchocerciasis, one which permanently sterilizes the worm) and (ii) the risk of worms developing drug-resistance. For example, currently available treatments for onchocerciasis include ivermectin, which kills worm larvae, but has little or no activity against adult *Onchocerca volvulus* parasites. Thus, infected patients must be retreated with ivermectin for several years until the adult worms die naturally. The most commonly used dose interval is 12 months; however, retreatment with ivermectin may be considered at intervals as short as 3 months. In addition, there are also potential signs of resistance to ivermectin within the parasite in a few areas. Osei-Atweneboana M Y, et al. (2011) Phenotypic Evidence of Emerging Ivermectin Resistance in *Onchocerca volvulus*. PLoS Negl Trop Dis 5(3): e998. In addition, there is a danger in treating patients co-infected with both (i) *Wuchereria bancrofti*, *Brugia malayi*, *Brugia timori*, and/or *Onchocerca volvulus*; and (ii) *Loa loa* with ivermectin. In such co-infected patients, ivermectin treatment can cause severe reactions, including encephalopathy, leading to coma or even death. Thus, alternative, and more effective, treatments for filarial worm diseases and, in particular, onchocerciasis and lymphatic filariasis are needed.

Antibiotics, such as doxycycline, minocycline, and rifampicin, have been demonstrated to be effective against *Wolbachia*. Taylor et al., (2005) Lancet. 365(9477):2116-2121 and Townson S, et al., (2006) Filaria J. 5:4. However, it has been reported that other classes of antibiotics, such as penicillins, aminoglycosides, and macrolides are ineffective at depleting *Wolbachia* from filariae. Hoerauf A, et al. (1999) Journal of Clinical Investigation 103(1):11-18 and Hoerauf A, et al. (2000) Trop Med Int Health 5(4):275-279.

Existing anti-*Wolbachia* drugs are non-optimal; they require a relatively long course of treatment (~4 weeks) and often exclude certain subjects, including pregnant women and children under the age of 9 (e.g., with tetracyclines). Thus, there exists a need for better anti-*Wolbachia* treatments, such as those providing a shorter treatment regimen (e.g., 7 days or less) and usable in currently restricted populations (Taylor et al. *Parasitology*, 141(1):119-27).

SUMMARY OF THE INVENTION

In one aspect, the present invention includes a method of treating a subject infected with a filarial worm. In certain embodiments, the method includes administering a therapeutically effective amount of a macrolide antibiotic to the subject. In certain embodiments, the macrolide antibiotic is tylosin A, a tylosin A analog, a tylosin A derivative, or a salt thereof. In certain embodiments, the filarial worm is infected with a bacterium belonging to the genera *Wolbachia*.

In one aspect, the present invention includes a method of treating a subject infected with a filarial worm. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to the subject. In certain embodiments, the filarial worm is *Onchocerca volvulus*. In certain embodiments, the filarial worm is *Wuchereria bancrofti*. In certain embodiments, the filarial worm is *Brugia malayi*. In certain embodiments, the filarial worm is *Brugia timori*. In certain embodiments, the filarial worm is *Dirofilaria immitis*, which is a causative agent of canine cardiovascular dirofilariasis, or canine heartworm disease. In certain embodiments, the filarial worm is infected with a bacterium belonging to the genera *Wolbachia*.

In one aspect, the present invention includes a method of treating a human subject co-infected, or suspected to be co-infected, with (i) *Wuchereria bancrofti*, *Brugia malayi*, *Brugia timori*, and/or *Onchocerca volvulus*; and (ii) *Loa loa*. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to the human subject. In certain embodiments, the treatment selectively kills *Wuchereria bancrofti*, *Brugia malayi*, *Brugia timori*, and/or *Onchocerca volvulus* microfilariae but not *Loa loa* microfilariae. In this way, adverse effects associated with killing vast numbers of *Loa loa* microfilariae can be avoided. In certain embodiments, the human subject has been diagnosed with a *Loa loa* infection using a standard diagnostic test (e.g., an assessment of *Loa loa* microfilariae in the subject's blood). In certain other embodiments, the human subject is suspected of having a *Loa loa* infection. For example, the human subject may come from a region co-endemic for loiasis and lymphatic filariasis or onchocerciasis.

In another aspect, the present invention includes a method of inhibiting growth of a filarial worm and/or killing a filarial worm. In certain embodiments, the method includes contacting a filarial worm with a macrolide antibiotic. In certain embodiments, the macrolide antibiotic is tylosin A, a tylosin A analog, a tylosin A derivative, or a salt thereof. In certain embodiments, the filarial worm is infected with a bacterium belonging to the genera *Wolbachia*.

In another aspect, the present invention includes a method of inhibiting growth of a filarial worm and/or killing a filarial worm. In certain embodiments, the method includes contacting a filarial worm with a compound of Formula (I), (I-1), (II), (III), (IV), (V), (VI), (VII), (VIII), (IX), or a pharmaceutically acceptable salt thereof, in an amount effective to inhibit growth of the filarial worm and/or kill the filarial worm. In certain embodiments, the filarial worm is *Onchocerca volvulus*. In certain embodiments, the filarial worm is *Wuchereria bancrofti*. In certain embodiments, the filarial worm is *Brugia malayi*. In certain embodiments, the filarial worm is *Brugia timori*. In certain embodiments, the filarial worm is *Dirofilaria immitis*. In certain embodiments, the filarial worm is infected with a bacterium belonging to the genera *Wolbachia*.

In another aspect, the present invention includes a method of treating a subject having a *Wolbachia* infection. In certain embodiments, the method includes administering a therapeutically effective amount of a macrolide antibiotic to the subject. In certain embodiments, the *Wolbachia* infection is associated with a filarial worm infection.

In another aspect, the present invention includes a method of treating a subject having a *Wolbachia* infection. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to the subject. In certain embodiments, the *Wolbachia* infection is associated with a filarial worm infection.

In another aspect, the present invention includes a method of inhibiting growth of bacteria associated with a filarial worm and/or killing bacteria associated with a filarial worm. In certain embodiments, the method includes contacting the bacteria associated with the filarial worm with a macrolide antibiotic in an amount effective to inhibit growth of the bacteria and/or kill the bacteria. In certain embodiments, the macrolide antibiotic is tylosin A, a tylosin A analog, a tylosin A derivative, or a salt thereof. In certain embodiments, the bacteria belong to the genera *Wolbachia*.

In another aspect, the present invention includes a method of inhibiting growth of bacteria associated with a filarial worm and/or killing bacteria associated with a filarial worm. In certain embodiments, the method includes contacting the bacteria associated with the filarial worm with a compound of Formula (I), (I-1), (II), (III), (IV), (V), (VI), (VII), (VIII), (IX), or a pharmaceutically acceptable salt thereof, in an amount effective to inhibit growth of the bacteria and/or kill the bacteria. In certain embodiments, the bacteria belong to the genera *Wolbachia*. In certain embodiments, the filarial worm is *Onchocerca volvulus*. In certain embodiments, the filarial worm is *Wuchereria bancrofti*. In certain embodiments, the filarial worm is *Brugia malayi*. In certain embodiments, the filarial worm is *Brugia timori*. In certain embodiments, the filarial worm is *Dirofilaria immitis*.

In another aspect, the present invention includes a method of treating a disease caused by a filarial worm infection. In certain embodiments, the method includes administering a therapeutically effective amount of a macrolide antibiotic to a subject having a disease caused by a filarial worm infection. In certain embodiments, the macrolide antibiotic is tylosin A, a tylosin A analog, a tylosin A derivative, or a salt thereof. In certain embodiments, the disease is heartworm disease. In other embodiments, the disease is onchocerciasis. In still other embodiments, the disease is lymphatic filariasis.

In another aspect, the present invention includes a method of treating a disease caused by a filarial worm infection. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to a subject having a disease caused by a filarial worm infection. In certain embodiments, the disease is heartworm disease. In other embodiments, the disease is onchocerciasis. In still other embodiments, the disease is lymphatic filariasis.

In another aspect, the present invention includes a method of treating heartworm disease. In certain embodiments, the method includes administering a therapeutically effective amount of a macrolide antibiotic to a subject having heartworm disease. In certain embodiments, the macrolide antibiotic is tylosin A, a tylosin A analog, a tylosin A derivative, or a salt thereof. In certain embodiments, the heartworm disease is caused by infections of *Dirofilaria immitis*. In certain embodiments, the subject is an animal, such as a dog. In certain embodiments, the animal is characterized as being asymptomatic to having mild heartworm disease. In certain embodiments, the animal is characterized as having moderate heartworm disease. In certain embodiments, the animal is characterized as having severe heartworm disease.

In another aspect, the present invention includes a method of treating heartworm disease. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to a subject having heartworm disease. In certain embodiments, the heartworm disease is caused by infections of *Dirofilaria immitis*. In certain embodiments, the subject is an animal, such as a dog. In certain embodiments, the animal is characterized as being asymptomatic to having mild heartworm disease. In certain embodiments, the animal is characterized as having moderate heartworm disease. In certain embodiments, the animal is characterized as having severe heartworm disease.

In another aspect, the present invention includes a method of treating onchocerciasis. In certain embodiments, the method includes administering a therapeutically effective amount of a macrolide antibiotic to a subject having onchocerciasis. In certain embodiments, the macrolide antibiotic is tylosin A, a tylosin A analog, a tylosin A derivative, or a salt thereof. In certain embodiments, the onchocerciasis is due to the filarial worm parasite *Onchocerca volvulus*.

In another aspect, the present invention includes a method of treating onchocerciasis. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to a subject having onchocerciasis. In certain embodiments, the onchocerciasis is due to the filarial worm parasite *Onchocerca volvulus*.

In another aspect, the present invention includes a method of treating lymphatic filariasis. In certain embodiments, the method includes administering a therapeutically effective amount of a macrolide antibiotic to a subject having lymphatic filariasis. In certain embodiments, the macrolide antibiotic is tylosin A, a tylosin A analog, a tylosin A derivative, or a salt thereof. In certain embodiments, the lymphatic filariasis is due to the filarial worm parasite *Wuchereria bancrofti*. In certain embodiments, the lymphatic filariasis is due to the filarial worm parasite *Brugia malayi*. In certain embodiments, the lymphatic filariasis is due to the filarial worm parasite *Brugia timori*.

In another aspect, the present invention includes a method of treating lymphatic filariasis. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to a subject having lymphatic filariasis. In certain embodiments, the lymphatic filariasis is due to the filarial worm parasite *Wuchereria bancrofti*. In certain embodiments, the lymphatic filariasis is due to the filarial worm parasite *Brugia malayi*. In certain embodiments, the lymphatic filariasis is due to the filarial worm parasite *Brugia timori*.

In another aspect, the present invention includes a method of eliminating adult filarial worms. In certain embodiments, the method includes administering a therapeutically effective amount of a macrolide antibiotic to a subject infected with adult filarial worms. In certain embodiments, the macrolide antibiotic is tylosin A, a tylosin A analog, a tylosin A derivative, or a salt thereof. In certain embodiments, the filarial worms are *Onchocerca volvulus* worms. In certain embodiments, the filarial worms are *Wuchereria bancrofti* worms. In certain embodiments, the filarial worms are *Brugia malayi* worms. In certain embodiments, the filarial worms are *Brugia timori* worms. In certain embodiments, the filarial worms are *Dirofilaria immitis* worms.

In another aspect, the present invention includes a method of eliminating adult filarial worms. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to a subject infected with adult filarial worms. In certain embodiments, the filarial worms are *Onchocerca volvulus* worms. In certain embodiments, the filarial worms are *Wuchereria bancrofti* worms. In certain embodiments, the filarial worms are *Brugia malayi* worms. In certain embodiments, the filarial worms are *Brugia timori* worms. In certain embodiments, the filarial worms are *Dirofilaria immitis* worms.

In another aspect, the present invention includes a method of sterilizing adult filarial worms. In certain embodiments, the method includes administering a therapeutically effective amount of a macrolide antibiotic to a subject infected with filarial worms. In certain embodiments, the macrolide antibiotic is tylosin A, a tylosin A analog, a tylosin A derivative, or a salt thereof. In certain embodiments, the filarial worms are *Onchocerca volvulus* worms. In certain embodiments, the filarial worms are *Wuchereria bancrofti* worms. In certain embodiments, the filarial worms are *Brugia malayi* worms. In certain embodiments, the filarial worms are *Brugia timori* worms. In certain embodiments, the filarial worms are *Dirofilaria immitis* worms.

In another aspect, the present invention includes a method of sterilizing adult filarial worms. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to a subject infected with adult filarial worms. In certain embodiments, the filarial worms are *Onchocerca volvulus* worms. In certain embodiments, the filarial worms are *Wuchereria bancrofti* worms. In certain embodiments, the filarial worms are *Brugia malayi* worms. In certain embodiments, the filarial worms are *Brugia timori* worms. In certain embodiments, the filarial worms are *Dirofilaria immitis* worms.

In another aspect, the present invention includes a method of decreasing microfilariae in a subject infected with filarial worms. In certain embodiments, the method includes administering a therapeutically effective amount of a macrolide antibiotic to the subject. In certain embodiments, the macrolide antibiotic is tylosin A, a tylosin A analog, a tylosin A derivative, or a salt thereof. In certain embodiments, the filarial worms are *Onchocerca volvulus* worms. In certain embodiments, the filarial worms are *Wuchereria bancrofti* worms. In certain embodiments, the filarial worms are *Brugia malayi* worms. In certain embodiments, the filarial worms are *Brugia timori* worms. In certain embodiments, the filarial worms are *Dirofilaria immitis* worms.

In another aspect, the present invention includes a method of decreasing microfilariae in a subject infected with filarial worms. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to the subject. In certain embodiments, the filarial worms are *Onchocerca volvulus* worms. In certain embodiments, the filarial worms are *Wuchereria bancrofti* worms. In certain embodiments, the filarial worms are *Brugia malayi* worms. In certain embodiments, the filarial worms are *Brugia timori* worms. In certain embodiments, the filarial worms are *Dirofilaria immitis* worms.

In one aspect, the present invention includes a method of treating a subject having a disease caused by a filarial worm infection by administering an antibiotic compound for a treatment duration of no more than fourteen (14) days. In certain embodiments, the treatment duration is no more than seven (7) days, including but not limited to, no more than six (6) days, no more than five (5) days, no more than four (4) days, no more than three (3) days, no more than (2) days, no more than one (1) day, e.g., the treatment duration being seven (7) days. In certain embodiments, the method includes administering a therapeutically effective amount of a macrolide antibiotic to a subject having a disease caused by a filarial worm infection. In certain embodiments, the macrolide antibiotic is tylosin A, a tylosin A analog, a tylosin A derivative, or a salt thereof. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to a subject having a disease caused by a filarial worm infection. In certain embodiments, the disease is heartworm disease. In other embodiments, the disease is onchocerciasis. In still other embodiments, the disease is lymphatic filariasis.

In one aspect, the present invention includes a method of treating a subject with a filarial worm infection by administering an antibiotic compound for a treatment duration of no more than fourteen (14) days. In certain embodiments, the treatment duration is no more than seven (7) days, including but not limited to, no more than six (6) days, no more than five (5) days, no more than four (4) days, no more than three (3) days, no more than two (2) days, no more than one (1) day, e.g., the treatment duration being seven (7) days. In certain embodiments, the method includes administering a therapeutically effective amount of a macrolide antibiotic to the subject. In certain embodiments, the macrolide antibiotic is tylosin A, a tylosin A analog, a tylosin A derivative, or a salt thereof. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to the subject. In certain embodiments, the filarial worm is *Onchocerca volvulus*. In certain embodiments, the filarial worm is *Wuchereria bancrofti*. In certain embodiments, the filarial worm is *Brugia malayi*. In certain embodiments, the filarial worm is *Brugia timori*. In certain embodiments, the filarial worm is *Dirofilaria immitis*. In certain embodiments, the filarial worm is infected with a bacterium belonging to the genera *Wolbachia*.

These and other objects of the invention are described in the following paragraphs. These objects should not be deemed to narrow the scope of the invention.

DETAILED DESCRIPTION OF THE INVENTION

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. Definitions

As used in the specification and the appended claims, unless specified to the contrary, the following terms have the meaning indicated:

The term "acyl" means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "alkenyl" means a straight or branched hydrocarbon chain containing one or more carbon-carbon double bonds and, typically, from 2 to 10 carbon atoms. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" means a straight or branched saturated hydrocarbon chain, typically containing from 1 to 10 carbon atoms. Representative examples of alkyl include, but are not limited to, methyl, ethyl, n-propyl, isopropyl, n-butyl, isobutyl, sec-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. In certain instances, the hydrogen atoms of the alkyl groups may be optionally substituted by one or more substituents, including, but not limited to, acyl, alkoxy, alkynyl, carboxy, halogen, and hydroxy.

The term "lower alkyl" or "$C_1$-$C_6$-alkyl" means a straight or branched hydrocarbon chain containing from 1 to 6 carbon atoms. In some instances, the number of carbon atoms in a hydrocarbon substituent (e.g., alkyl, alkenyl, alkynyl, aryl, or cycloalkyl) is indicated by the prefix "$C_x$-$C_y$—", wherein x is the minimum and y is the maximum number of carbon atoms in the substituent. Thus, for example, "$C_1$-$C_6$-alkyl" refers to an alkyl substituent containing from 1 to 6 carbon atoms. Likewise, "$C_6$-$C_{10}$-aryl" refers to an aryl substituent containing from 6 to 10 carbon ring atoms. Similarly, "$C_3$-$C_8$-cycloalkyl" refers to a cycloalkyl substituent containing from 3 to 8 carbon ring atoms.

The term "alkylene" means a divalent group derived from a straight or branched hydrocarbon chain, typically containing 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" means a straight or branched hydrocarbon chain containing one or more carbon-carbon triple bonds and, typically, from 2 to 10 carbon atoms. Representative examples of alkynyl include, but are not limited to, ethynyl, 2-propynyl, 3-propynyl, 2-butynyl, and 3-butynyl and the like.

The term "aryl" means an aromatic carbocyclyl containing from 6 to 14 carbon ring atoms. An aryl may be monocyclic or polycyclic (i.e., may contain more than one ring). In the case of a polycyclic aryl, only one ring of the polycyclic system is required to be aromatic while the remaining ring(s) may be saturated, partially saturated or unsaturated. Representative examples of aryl include, but are not limited to, phenyl, naphthalenyl, indenyl, indanyl, and tetrahydronapthyl. Unless otherwise specified herein, the aryl groups can be substituted or unsubstituted. Thus, the hydrogen atoms of the aryl groups may be optionally substituted by one or more substituents, including, but not limited to, acyl, alkenyl, alkoxy, alkyl, alkynyl, carboxy, haloalkyl, halogen, hydroxy, and hydroxyalkyl.

The term "arylalkyl" means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "carbocyclyl" means a saturated cyclic, partially saturated cyclic, or completely unsaturated cyclic hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

The term "carbonyl" means a —C(O)— group.

The term "carboxy" means a —$CO_2H$ group.

The term "cycloalkyl" means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include, but are not limited to, cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls. Unless otherwise specified herein, the cycloalkyl groups can be substituted or unsubstituted. Thus, the hydrogen atoms of the cycloalkyl groups may be optionally substituted by one or more substituents, including, but not limited to, acyl, alkenyl, alkoxy, alkyl, alkynyl, carboxy, haloalkyl, halogen, hydroxy, and hydroxyalkyl.

The term "cycloalkylalkyl" means a cycloalkyl group, as defined herein, appended to the parent molecular moiety through an alkylene group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "halo" or "halogen" means an atom selected from fluorine, chlorine, bromine, and iodine.

The term "haloalkyl" means an alkyl group, as defined herein, in which one or more hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" means an aromatic heterocyclyl containing from 5 to 14 ring atoms. A heteroaryl may be monocyclic or polycyclic (i.e., may contain more than one ring). In the case of a polycyclic heteroaryl, only one ring of the polycyclic system is required to be aromatic while the remaining ring(s) may be saturated, partially saturated or unsaturated. Representative examples of heteroaryl include, but are not limited to, 6-membered ring substituents such as pyridyl, pyrazyl, pyrimidinyl, pyridazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; fused ring substituents such as benzothiazolyl, benzothiofuranyl, benzisoxazolyl, benzoxazolyl, purinyl; benzopyranyl, quinolinyl, isoquinolinyl, cinnolinyl, quinazolinyl, and benzoxazinyl. Unless otherwise specified herein, the heteroaryl groups can be substituted or unsubstituted. Thus, the hydrogen atoms of the heteroaryl groups may be optionally substituted by one or more substituents, including, but not limited to, acyl, alkenyl, alkoxy, alkyl, alkynyl, carboxy, haloalkyl, halogen, hydroxy, and hydroxyalkyl.

The term "heteroarylalkyl" means a heteroaryl, as defined herein, appended to the parent molecular moiety through an alkylene group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heteroatom" means a nitrogen, oxygen, or sulfur atom.

The term "heterocycloalkyl" means a saturated heterocyclyl. Unless otherwise specified herein, the heterocycloalkyl groups can be substituted or unsubstituted. Thus, the hydrogen atoms of the heterocycloalkyl groups may be optionally substituted by one or more substituents, including, but not limited to, acyl, alkenyl, alkoxy, alkyl, alkynyl, carboxy, haloalkyl, halogen, hydroxy, and hydroxyalkyl.

The term "heterocyclyl" or "heterocyclic" means a saturated, partially saturated, or completely unsaturated ring structure containing a total of 3 to 14 ring atoms, where at least one of the ring atoms is a heteroatom (i.e., oxygen, nitrogen, or sulfur), with the remaining ring atoms being independently selected from the group consisting of carbon, oxygen, nitrogen, and sulfur. A heterocyclic ring may be a single-ring (monocyclic) or polycyclic ring structure. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl.

The term "hydroxyl" or "hydroxy" means an —OH group.

The term "hydroxyalkyl" means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

If a particular substituent is described as being "substituted", it means that there are one or more substituents other than hydrogen attached to that particular substituent. Thus, for example, a substituted alkyl is an alkyl in which at least one non-hydrogen substituent is in the place of a hydrogen atom on the alkyl. If a particular substituent is described as being "optionally substituted", that particular substituent may be either (1) not substituted or (2) substituted.

The terms "treat", "treating" and "treatment" refer to a method of alleviating or abrogating a condition, disorder, or disease and/or the attendant symptoms thereof.

The terms "prevent", "preventing" and "prevention" refer to a method of preventing the onset of a condition, disorder, or disease and/or the attendant symptoms thereof or barring a subject from acquiring a condition, disorder, or disease. As used herein, "prevent", "preventing" and "prevention" also include delaying the onset of a condition, disorder, or disease and/or the attendant symptoms thereof and reducing a subject's risk of acquiring a condition, disorder, or disease.

The term "pharmaceutically acceptable" is used adjectivally to mean that the modified noun is appropriate for use as a pharmaceutical product or as a part of a pharmaceutical product.

The term "therapeutically effective amount" means a sufficient amount of the compound to treat a condition, disorder, or disease, at a reasonable benefit/risk ratio applicable to any medical treatment. When used in a medical treatment, a therapeutically effective amount of one of the present compounds can be employed in pure form or, where such forms exist, in pharmaceutically acceptable salt or ester, or amide form. Alternatively, the compound can be administered as a pharmaceutical composition containing the compound of interest in combination with one or more pharmaceutically acceptable carriers.

The term "subject" includes humans and other primates as well as domesticated and semi-domesticated animals including, but not limited to, poultry, honeybees, cows, sheep, goats, pigs, horses, dogs, cats, rabbits, rats, mice and the like. The term "poultry" encompasses all types of domestic fowl, including, but not limited to chickens, turkey, ducks, geese, the ratite group of birds and game birds. In certain embodiments, the subject is a human.

B. Methods of Use

In one aspect, the present invention provides a method of treating a disease caused by a filarial worm infection. In certain embodiments, a macrolide antibiotic is used in human medical therapy, particularly in the treatment of worm-associated disease. In certain embodiments, a macrolide antibiotic is used in veterinary medical therapy, particularly in the treatment of worm-associated disease. In certain embodiments, the method includes administering a therapeutically effective amount of a macrolide antibiotic to a subject having a disease caused by a filarial worm infection. In certain embodiments, the macrolide antibiotic is tylosin A, a tylosin A analog, a tylosin A derivative, or a salt thereof. In certain embodiments, the macrolide antibiotic is tylosin tartrate (commercially available as Tylan®). In certain embodiments, the macrolide antibiotic is tylvalosin tartrate (commercially available as Aivlosin®) or tilmicosin phosphate (commercially available as Micotil®). In certain embodiments, the macrolide antibiotic is tylosin B, or a salt thereof.

In one aspect, the present invention provides a method of treating a disease caused by a filarial worm infection. In certain embodiments, a compound of Formula (I), (I-1), (II), (III), (IV), (V), (VI), (VII), (VIII), (IX), or a pharmaceutically acceptable salt thereof, is used in human medical therapy, particularly in the treatment of worm-associated disease. In certain embodiments, a compound of Formula (I), (I-1), (II), (III), (IV), (V), (VI), (VII), (VIII), (IX), or a pharmaceutically acceptable salt thereof, is used in veterinary medical therapy, particularly in the treatment of worm-associated disease. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to a subject having a disease caused by a filarial worm infection.

In another aspect, the present invention provides a method of preventing a disease caused by a filarial worm infection. In certain embodiments, a macrolide antibiotic is used in human medical therapy, particularly in the prevention of worm-associated disease. In certain embodiments, a macrolide antibiotic is used in veterinary medical therapy, particularly in the prevention of worm-associated disease. In certain embodiments, the method includes administering a therapeutically effective amount of a macrolide antibiotic to a subject to prevent a disease caused by a filarial worm infection. In certain embodiments, the macrolide antibiotic is tylosin A, a tylosin A analog, a tylosin A derivative, or a salt thereof. In certain embodiments, the macrolide antibiotic is tylosin tartrate (commercially available as Tylan®). In certain embodiments, the macrolide antibiotic is tylvalosin tartrate (commercially available as Aivlosin®) or tilmicosin phosphate (commercially available as Micotil®).

In another aspect, the present invention provides a method of preventing a disease caused by a filarial worm infection. In certain embodiments, a compound of Formula (I), (I-1), (II), (III), (IV), (V), (VI), (VII), (VIII), (IX), or a pharmaceutically acceptable salt thereof, is used in human medical therapy, particularly in the prevention of worm-associated disease. In certain embodiments, a compound of Formula (I), (I-1), (II), (III), (IV), (V), (VI), (VII), (VIII), (IX), or a pharmaceutically acceptable salt thereof, is used in veterinary medical therapy, particularly in the prevention of worm-associated disease. In certain embodiments, the method includes administering a therapeutically effective amount of a compound of Formula (I), (I-1), (II), (III), (IV), (V), (VI), (VII), (VIII), (IX), or a pharmaceutically acceptable salt thereof, to a subject to prevent a disease caused by a filarial worm infection.

In another aspect, the present invention provides a method of preventing or treating a parasitic disease. In certain embodiments, the parasitic disease is associated with a worm. In certain embodiments, the parasitic disease is caused by a worm. In certain embodiments, the parasitic disease is associated with a helminth. In certain embodiments, the parasitic disease is associated with a nematode. In certain embodiments, the nematode is *Wuchereria bancrofti*. In certain embodiments, the nematode is *Brugia malayi*. In certain embodiments, the nematode is *Brugia timori*. In certain embodiments, the nematode is *Dirofilaria immitis*. In certain embodiments, the parasitic disease is associated with a trematode. In certain embodiments, the parasitic disease is associated with *Schistosoma*. In certain embodiments, the parasitic disease is associated with *Schistosoma mansoni*. In certain embodiments, the parasitic disease is enterobiasis, oxyuriasis, ascariasis, dracunculiasis, filariasis, onchocerciasis, schistosomiasis, or trichuriasis. In certain embodiments, the parasitic disease is schistosomiasis. In certain embodiments, the parasitic disease is urinary schistosomiasis. In certain embodiments, the parasitic disease is intestinal schistosomiasis. In certain embodiments, the parasitic disease is Asian intestinal schistosomiasis. In certain embodiments, the parasitic disease is visceral schistosomiasis. In certain embodiments, the parasitic disease is acute schistosomiasis. In certain embodiments, the parasitic disease is lymphatic filariasis. In certain embodiments, the parasitic disease is bancroftian filariasis. In certain embodiments, the parasitic disease is subcutaneous filariasis. In certain embodiments, the parasitic disease is serious cavity filariasis. In certain embodiments, the parasitic disease is elephantiasis. In certain embodiments, the parasitic disease is elephantiasis tropica. In certain embodiments, the parasitic disease is onchocerciasis.

In certain aspects, the present methods include a step of administering a macrolide antibiotic, tylosin A, tylosin B, a tylosin A analog, a tylosin A derivative, a compound of Formula (I), (I-1), (II), (III), (IV), (V), (VI), (VII), (VIII), (IX), or a pharmaceutically acceptable salt thereof, to a subject. In certain embodiments, the methods comprise administering a macrolide antibiotic, tylosin A, tylosin B, a tylosin A analog, a tylosin A derivative, a compound of Formula (I), (I-1), (II), (III), (IV), (V), (VI), (VII), (VIII), (IX), or a pharmaceutically acceptable salt thereof, to a subject for no more than fourteen (14) days. In certain embodiments, the methods comprise administering a macrolide antibiotic, tylosin A, tylosin B, a tylosin A analog, a tylosin A derivative, a compound of Formula (I), (I-1), (II), (III), (IV), (V), (VI), (VII), (VIII), (IX), or a pharmaceutically acceptable salt thereof, to a subject for no more than seven (7) days. In certain embodiments, the subject is in need of treatment for a fliarial infection. In certain embodiments, the subject is a pediatric subject. In certain embodiments, the subject is less than nine (9) years of age. In certain embodiments, the subject is less than eight (8) years of age. In certain embodiments, the subject is a pregnant woman. In certain embodiments, the subject is a post-partum woman. In certain embodiments, the subject is a woman of childbearing potential. In certain embodiments, the subject is an individual attempting to conceive a child.

Compounds disclosed herein exhibit potency against filarial worms, and, therefore, have the potential to kill and/or inhibit the growth of such filarial worms. Thus, one aspect of the present invention includes a method of killing a filarial worm, comprising: contacting the filarial worm with tylosin, a tylosin A analog, a tylosin A derivative, a compound of Formula (I), (I-1), (II), (III), (IV), (V), (VI), (VII), (VIII), (IX), or a pharmaceutically acceptable salt thereof, in an amount effective to kill the filarial worm. Another aspect of the present invention includes a method of inhibiting growth of a filarial worm, comprising: contacting the filarial worm with tylosin, a tylosin A analog, a tylosin A derivative, a compound of Formula (I), (I-1), (II), (III), (IV), (V), (VI), (VII), (VIII), (IX), or a pharmaceutically acceptable salt thereof, in an amount effective to inhibit growth of the filarial worm. In certain embodiments, the worm is an egg. In certain embodiments, the egg is an unfertilized egg. In certain embodiments, the egg is fertilized egg. In certain embodiments, the worm is a larva. In certain embodiments, the worm is mature. In certain embodiments, the worm is fully mature. In certain embodiments, the worm is contacted with tylosin, a tylosin A analog, a tylosin A derivative, a compound of Formula (I), (I-1), (II), (III), (IV), (V), (VI), (VII), (VIII), (IX), or a pharmaceutically acceptable salt thereof, inside an animal. In certain embodiments, the worm is contacted with tylosin, a tylosin A analog, a tylosin A derivative, a compound of Formula (I), (I-1), (II), (III), (IV), (V), (VI), (VII), (VIII), (IX), or a pharmaceutically acceptable salt thereof, outside an animal.

Compounds disclosed herein exhibit potency against bacteria which are associated with filarial worms. Thus, one aspect of the present invention includes a method of killing bacteria associated with a filarial worm, comprising: contacting the bacteria associated with a filarial worm with tylosin, a tylosin A analog, a tylosin A derivative, a compound of Formula (I), (I-1), (II), (III), (IV), (V), (VI), (VII), (VIII), (IX), or a pharmaceutically acceptable salt thereof, in an amount effective to kill the bacteria. Another aspect of the present invention includes a method of inhibiting growth of a bacteria associated with a filarial worm, comprising: contacting the bacteria associated with a filarial worm with tylosin, a tylosin A analog, a tylosin A derivative, a compound of Formula (I), (I-1), (II), (III), (IV), (V), (VI), (VII), (VIII), (IX), or a pharmaceutically acceptable salt thereof, in an amount effective to inhibit growth of the bacteria. In certain embodiments, the bacteria are contacted with the compound of Formula I, or the pharmaceutically acceptable salt thereof, inside the filarial worm. In certain embodiments, the bacteria are contacted with tylosin, a tylosin A analog, a tylosin A derivative, a compound of Formula (I), (I-1), (II), (III), (IV), (V), (VI), (VII), (VIII), (IX), or a pharmaceutically acceptable salt thereof, outside the filarial worm.

As discussed herein, compounds disclosed herein are useful for treating and preventing certain diseases and disorders in humans and animals. In certain embodiments, tylosin, a tylosin A analog, a tylosin A derivative, a compound of Formula (I), (I-1), (II), (III), (IV), (V), (VI), (VII), (VIII), (IX), or a pharmaceutically acceptable salt thereof, is used to treat disease caused by filarial worm infection, including, but not limited to, heartworm disease, onchocerciasis, and lymphatic filariasis. In certain embodiments, treatment or prevention of such diseases and disorders can be effected by administering tylosin, a tylosin A analog, a tylosin A derivative, a compound of Formula (I), (I-1), (II), (III), (IV), (V), (VI), (VII), (VIII), (IX), or a pharmaceutically acceptable salt thereof, either alone or in combination with another active agent as part of a combination therapy. The term "combination" as in the phrase "in combination with another active agent" includes co-administration of a first agent and a second agent, which for example may be dissolved or intermixed in the same pharmaceutically acceptable carrier, or administration of a first agent, followed by the second agent, or administration of the second agent, followed by the first agent. The present methods and compositions, therefore, include methods of combination therapeutic treatment and combination pharmaceutical compositions. The term "combination therapy" refers to the administration of two or more therapeutic substances, such as a macrolide antibiotic and another drug (e.g., an antihelminthic agent such as ivermectin, albendazole, flubendazole, diethylcarbamazine, or emodepside). The other drug(s) may be administered concomitant with, prior to, or following the administration of the macrolide antibiotic.

The preferred total daily dose of a compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). In certain embodiments, dosage unit compositions contain such amounts or submultiples thereof to make up the daily dose. In many instances, the administration of the compound or salt will be repeated a plurality of times. In certain embodiments, multiple doses per day typically may be used to increase the total daily dose, if desired.

Factors affecting the preferred dosage regimen include the type, age, weight, sex, diet, and condition of the patient; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

C. Compounds for Prevention or Treatment of Filariasis

In certain embodiments, the present methods employ a macrolide antibiotic, including, but not limited to, tylosin A or a salt thereof.

In certain embodiments, the present methods employ tylosin A (2-((4R,5S,6S,7R,9R,11E,13E,15R,16R)-6-(((2R, 3R,4R,5S,6R)-5-(((2S,4R,5S,6S)-4,5-dihydroxy-4,6-dimethyltetrahydro-2H-pyran-2-yl)oxy)-4-(dimethylamino)-3-hydroxy-6-methyltetrahydro-2H-pyran-2-yl)oxy)-16-ethyl-4-hydroxy-15-((((2R,3R,4R,5R,6R)-5-hydroxy-3,4-dimethoxy-6-methyltetrahydro-2H-pyran-2-yl)oxy)methyl)-5,9,13-trimethyl-2,10-dioxooxacyclohexadeca-11, 13-dien-7-yl)acetaldehyde) or a salt thereof, which is a macrolide antibiotic that is commonly used to treat veterinary infections. Tylosin A is commercially available as, for example, tylosin tartrate (Tylan®).

In certain embodiments, the present methods employ tylvalosin or a salt thereof. Tylvalosin is commercially available as, for example, tylvalosin tartrate (Aivlosin®).

In certain embodiments, the present methods employ desmycosin, or Tylosin B, or a salt thereof.

In certain embodiments, the present methods employ tilmicosin or a salt thereof. Tilmicosin is commercially available as, for example, tilmicosin phosphate (Micotil®).

In certain embodiments, the present methods employ a compound having a structure of Formula (I), (II), (III), (IV), (V), (VI), (VII), or (VIII) or a salt thereof as further defined herein. In various embodiments, there can be variables that occur more than one time in any substituent or in the compound or any other formulae herein. Definition of a variable on each occurrence is independent of its definition at another occurrence. Further, combinations of variables or substituents are permissible only if such combinations result in stable compounds. Stable compounds are compounds that can be isolated from a reaction mixture.

In certain embodiments, the present methods employ a compound having a structure of Formula (I):

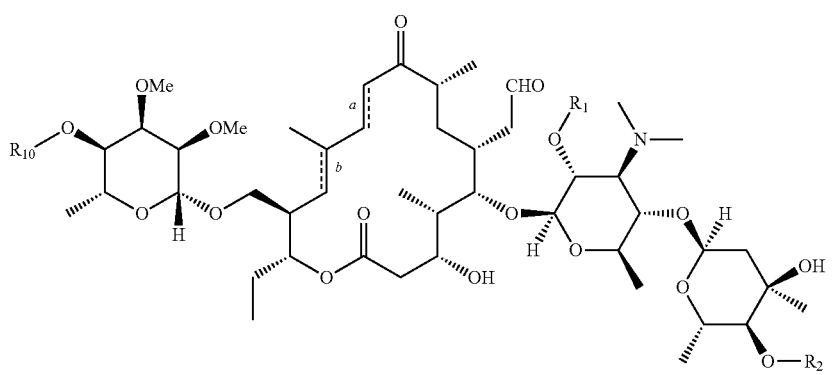

and salts thereof, wherein:

$R_1$ represents hydrogen or —C(O)$R_3$, wherein $R_3$ represents an optionally substituted $C_1$-$C_6$-alkyl or $C_1$-$C_6$-haloalkyl;

$R_2$ represents —C(O)C($R_4$)($R_5$)($R_6$), wherein $R_4$ is selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; and each of $R_5$ and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —CH$_2$-$A_1$, wherein $A_1$ represents a 6- to 10-membered aryl or a 5- to 10-membered heteroaryl and $A_1$ is unsubstituted or substituted with one or more $R_A$, wherein each $R_A$ is independently selected from the group consisting of halogen, $C_1$-$C_6$-alkyl, $C_1$-$C_6$-haloalkyl, and —O—$R_9$, where $R_9$ represents $C_1$-$C_6$-alkyl; and $R_{10}$ represents hydrogen or —C(O)$R_{11}$, wherein $R_{11}$ represents an optionally substituted $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, or $C_3$-$C_8$-cycloalkyl-$C_1$-$C_4$-alkyl; and each of a and b independently represents either a single bond or a double bond.

In certain embodiments, $R_1$ is hydrogen.

In certain embodiments, $R_1$ is —C(O)$R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl.

In certain embodiments, $R_2$ is —C(O)C($R_4$)($R_5$)($R_6$). In certain embodiments, $R_4$ is hydrogen. In certain embodiments, each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_5$ is $C_1$-$C_6$ alkyl. In certain embodiments, $R_6$ is $C_1$-$C_6$ alkyl. In certain embodiments, each of $R_4$, $R_5$, and $R_6$ are $C_1$-$C_6$ alkyl.

In certain embodiments, each of $R_4$, $R_5$, and $R_6$ are $C_1$-$C_6$-alkyl. In certain embodiments, $R_4$, $R_5$, and $R_6$ are the same. For example, in certain embodiments, each of $R_4$, $R_5$, and $R_6$ are methyl. In certain embodiments, at least two of $R_4$, $R_5$, and $R_6$ are the same. In certain embodiments, $R_4$, $R_5$, and $R_6$ are different.

In certain embodiments, $R_2$ is —C(O)N($R_7$)($R_8$). In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

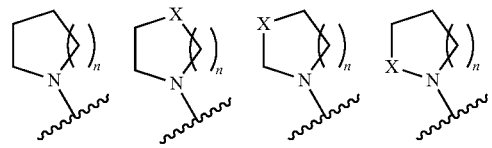

where X is O, S, or N($R_B$). $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_2$ is —CH$_2$-$A_1$ and $A_1$ is a 6- to 10-membered aryl or a 5- to 10-membered heteroaryl. In certain embodiments, $A_1$ is phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

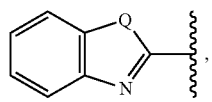

where Q is O, S, or N(R$_C$). R$_C$ is selected from hydrogen, C$_1$-C$_6$-alkyl, or C$_1$-C$_6$-haloalkyl.

In certain embodiments, A$_1$ is unsubstituted. In certain embodiments, A$_1$ is substituted with one or more R$_A$. In certain embodiments, R$_A$ is halogen, C$_1$-C$_6$-alkyl, C$_1$-C$_6$-haloalkyl, or —O—R$_9$. In certain embodiments, R$_A$ is —O—R$_9$ and R$_9$ is C$_1$-C$_6$-alkyl. In certain embodiments, R$_A$ is halogen, C$_1$-C$_6$-alkyl, or C$_1$-C$_6$-haloalkyl.

In certain embodiments, R$_1$ is —C(O)R$_3$ and R$_3$ is C$_1$-C$_6$-alkyl. In certain embodiments, R$_3$ is methyl. In certain embodiments, R$_3$ is propyl. In certain embodiments, R$_3$ is n-propyl. In certain embodiments, R$_3$ is isopropyl. In certain embodiments, R$_3$ is butyl. In certain embodiments, R$_3$ is n-butyl. In certain embodiments, R$_3$ is isobutyl. In certain embodiments, R$_3$ is tert-butyl.

In certain embodiments, R$_2$ is —C(O)C(R$_4$)(R$_5$)(R$_6$) and each of R$_4$, R$_5$, and R$_6$ are C$_1$-C$_6$ alkyl. In certain embodiments, R$_4$ is methyl. In certain embodiments, R$_5$ is methyl. In certain embodiments, R$_6$ is methyl. In certain embodiments, each of R$_4$, R$_5$, and R$_6$ are methyl.

In certain embodiments, R$_2$ is —C(O)N(R$_7$)(R$_8$) and one or both of R$_7$ or R$_8$ are C$_1$-C$_6$ alkyl. In certain embodiments, one or both of R$_7$ or R$_8$ are methyl. In certain embodiments, one or both of R$_7$ or R$_8$ are ethyl. In certain embodiments, one or both of R$_7$ or R$_8$ are propyl, such as n-propyl or isopropyl. In certain embodiments, one or both of R$_7$ or R$_8$ are butyl, such as n-butyl, isobutyl, or sec-butyl.

In certain embodiments, R$_2$ is —C(O)N(R$_7$)(R$_8$) and each of R$_7$ and R$_8$ are C$_1$-C$_6$ alkyl. In certain embodiments, both of R$_7$ and R$_8$ are methyl. In certain embodiments, both of R$_7$ and R$_8$ are ethyl. In certain embodiments, both of R$_7$ and R$_8$ are propyl, such as n-propyl or isopropyl. In certain embodiments, both of R$_7$ and R$_8$ are butyl, such as n-butyl, isobutyl, or sec-butyl. In certain embodiments, one of R$_7$ or R$_8$ is butyl and the other of R$_7$ or R$_8$ is ethyl.

In certain embodiments, R$_2$ is —C(O)N(R$_7$)(R$_8$) and one or both of R$_7$ or R$_8$ are C$_3$-C$_8$-cycloalkyl. In certain embodiments, both of R$_7$ and R$_8$ are C$_3$-C$_8$-cycloalkyl. In certain embodiments, both of R$_7$ and R$_8$ are cyclohexyl.

In certain embodiments, R$_2$ is —C(O)N(R$_7$)(R$_8$) and one of R$_7$ or R$_8$ is C$_1$-C$_6$ alkyl and the other of R$_7$ or R$_8$ is aryl. In certain embodiments, one of R$_7$ or R$_8$ is phenyl and the other of R$_7$ or R$_8$ is ethyl.

In certain embodiments, R$_2$ is dialkyl carbamoyl. In certain embodiments, R$_2$ is dimethyl carbamoyl. In certain embodiments, R$_2$ is diethyl carbamoyl. In certain embodiments, R$_2$ is dipropyl carbamoyl. In certain embodiments, R$_2$ is di(propan-2-yl)carbamoyl. In certain embodiments, R$_2$ is dibutyl carbamoyl. In certain embodiments, R$_2$ is bis(2-methylpropyl)carbamoyl. In certain embodiments, R$_2$ is N-butyl-N-ethylcarbamoyl.

In certain embodiments, R$_2$ is N-methyl-N-phenylcarbamoyl.

In certain embodiments, R$_2$ is dicyclohexylcarbamoyl.

In certain embodiments, R$_2$ is —C(O)N(R$_7$)(R$_8$) and R$_7$ and R$_8$ together with the nitrogen atom to which they are attached form an optionally substituted saturated or partially saturated heterocyclic ring. In certain embodiments, the heterocyclic ring is a non-aromatic ring. In certain embodiments, the heterocyclic ring is a pyrrolidine. In certain embodiments, the heterocyclic ring is a piperidine. In certain embodiments, the heterocyclic ring is a morpholine. In certain embodiments, the heterocyclic ring is an azepane.

In certain embodiments, R$_2$ is —CH$_2$-A$_1$.

In certain embodiments, A$_1$ is an unsubstituted phenyl. In certain embodiments, R$_2$ is unsubstituted benzyl.

In certain embodiments, A$_1$ is a phenyl substituted with one or more R$_A$. In certain embodiments, R$_A$ is haloalkyl. In certain embodiments, R$_A$ is trifluoromethyl. In certain embodiments, R$_A$ is halogen. In certain embodiments, R$_A$ is fluoro. In certain embodiments, R$_A$ is chloro. In certain embodiments, R$_A$ is an alkoxy, such as methoxy. In certain embodiments, R$_2$ is substituted benzyl. In certain embodiments, R$_2$ is trifluoromethylbenzyl. In certain embodiments, R$_2$ is trifluorobenzyl. In certain embodiments, R$_2$ is fluorobenzyl. In certain embodiments, R$_2$ is difluorobenzyl. In certain embodiments, R$_2$ is chlorobenzyl. In certain embodiments, R$_2$ is 4-methoxybenzyl.

In certain embodiments, A$_1$ is naphthalene. In certain embodiments, A$_1$ is benzothiazole.

In certain embodiments, R$_{10}$ is —C(O)R$_{11}$. In certain embodiments, R$_{11}$ is C$_1$-C$_6$-alkyl, such as methyl; ethyl; propyl, such as n-propyl or isopropyl; or butyl, such as n-butyl, isobutyl, or tert-butyl. In certain embodiments, R$_{11}$ is aryl, such as substituted or unsubstituted phenyl.

In certain embodiments, R$_{11}$ is methyl. In certain embodiments, R$_{110}$ is ethyl. In certain embodiments, R$_{11}$ is isopropyl.

In certain embodiments, both a and b are a double bond. In certain embodiments, at least one of a and b are a single bond. In certain embodiments, both a and b are a single bond.

In certain embodiments, both a and b are a double bond; R$_1$ and R$_{10}$ are both hydrogen; and A$_1$ is neither unsubstituted phenyl nor 4-methoxyphenyl.

In certain embodiments, both a and b are a double bond; R$_1$ and R$_{10}$ are both hydrogen or both C(O)CH$_3$; and neither R$_7$ nor R$_8$ is hydrogen.

In certain embodiments, the present methods employ a compound having a structure of Formula (I-1):

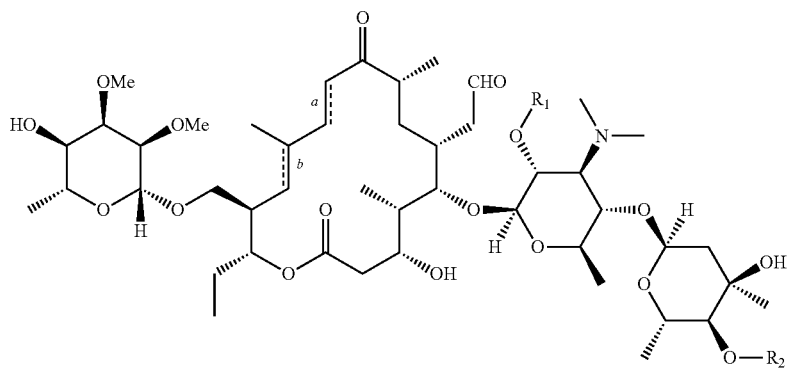

(I-1)

and salts thereof, wherein:

$R_1$ represents hydrogen or —C(O)$R_3$, wherein $R_3$ represents $C_1$-$C_6$-alkyl;

$R_2$ represents —C(O)C($R_4$)($R_5$)($R_6$), wherein $R_4$ is selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; and each of $R_5$ and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —CH$_2$-$A_1$, wherein $A_1$ represents a 6- to 10-membered aryl or a 5- to 10-membered heteroaryl and $A_1$ is unsubstituted or substituted with one or more $R_A$, wherein each $R_A$ is independently selected from the group consisting of halogen, $C_1$-$C_6$-alkyl, $C_1$-$C_6$-haloalkyl, and —O—$R_9$, where $R_9$ represents $C_1$-$C_6$-alkyl; and each of a and b independently represents either a single bond or a double bond.

In certain embodiments, $R_1$ is hydrogen.

In certain embodiments, $R_1$ is —C(O)$R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl.

In certain embodiments, $R_2$ is —C(O)C($R_4$)($R_5$)($R_6$). In certain embodiments, $R_4$ is hydrogen. In certain embodiments, each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_5$ is $C_1$-$C_6$ alkyl. In certain embodiments, $R_6$ is $C_1$-$C_6$ alkyl. In certain embodiments, each of $R_4$, $R_5$, and $R_6$ are $C_1$-$C_6$ alkyl.

In certain embodiments, each of $R_4$, $R_5$, and $R_6$ are $C_1$-$C_6$-alkyl. In certain embodiments, $R_4$, $R_5$, and $R_6$ are the same. For example, in certain embodiments, each of $R_4$, $R_5$, and $R_6$ are methyl. In certain embodiments, at least two of $R_4$, $R_5$, and $R_6$ are the same. In certain embodiments, $R_4$, $R_5$, and $R_6$ are different.

In certain embodiments, $R_2$ is —C(O)N($R_7$)($R_8$). In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

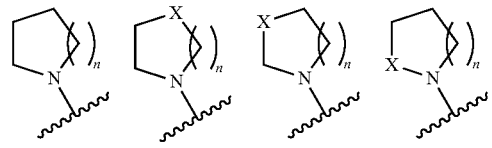

where X is O, S, or N($R_B$). $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_2$ is —CH$_2$-$A_1$ and $A_1$ is a 6- to 10-membered aryl or a 5- to 10-membered heteroaryl. In certain embodiments, $A_1$ is phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

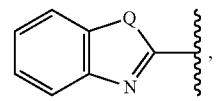

where Q is O, S, or N($R_C$). $R_C$ is selected from hydrogen, $C_1$-$C_6$-alkyl, or $C_1$-$C_6$-haloalkyl.

In certain embodiments, $A_1$ is unsubstituted. In certain embodiments, $A_1$ is substituted with one or more $R_A$. In certain embodiments, $R_A$ is halogen, $C_1$-$C_6$-alkyl, $C_1$-$C_6$-haloalkyl, or —O—$R_9$. In certain embodiments, $R_A$ is —O—$R_9$ and $R_9$ is $C_1$-$C_6$-alkyl. In certain embodiments, $R_A$ is halogen, $C_1$-$C_6$-alkyl, or $C_1$-$C_6$-haloalkyl.

In certain embodiments, $R_1$ is —C(O)$R_3$ and $R_3$ is $C_1$-$C_6$-alkyl. In certain embodiments, $R_3$ is methyl. In certain embodiments, $R_3$ is propyl. In certain embodiments, $R_3$ is n-propyl. In certain embodiments, $R_3$ is isopropyl. In certain embodiments, $R_3$ is butyl. In certain embodiments, $R_3$ is n-butyl. In certain embodiments, $R_3$ is isobutyl. In certain embodiments, $R_3$ is tert-butyl.

In certain embodiments, $R_2$ is —C(O)C($R_4$)($R_5$)($R_6$) and each of $R_4$, $R_5$, and $R_6$ are $C_1$-$C_6$ alkyl. In certain embodiments, $R_4$ is methyl. In certain embodiments, $R_5$ is methyl. In certain embodiments, $R_6$ is methyl. In certain embodiments, each of $R_4$, $R_5$, and $R_6$ are methyl.

In certain embodiments, $R_2$ is —C(O)N($R_7$)($R_8$) and one or both of $R_7$ or $R_8$ are $C_1$-$C_6$ alkyl. In certain embodiments, one or both of $R_7$ or $R_8$ are methyl. In certain embodiments, one or both of $R_7$ or $R_8$ are ethyl. In certain embodiments, one or both of $R_7$ or $R_8$ are propyl, such as n-propyl or isopropyl. In certain embodiments, one or both of $R_7$ or $R_8$ are butyl, such as n-butyl, isobutyl, or sec-butyl.

In certain embodiments, $R_2$ is —C(O)N($R_7$)($R_8$) and each of $R_7$ and $R_8$ are $C_1$-$C_6$ alkyl. In certain embodiments, both of $R_7$ and $R_8$ are methyl. In certain embodiments, both of $R_7$ and $R_8$ are ethyl. In certain embodiments, both of $R_7$ and $R_8$ are propyl, such as n-propyl or isopropyl. In certain embodiments, both of $R_7$ and $R_8$ are butyl, such as n-butyl, isobutyl, or sec-butyl. In certain embodiments, one of $R_7$ or $R_8$ is butyl and the other of $R_7$ or $R_8$ is ethyl.

In certain embodiments, $R_2$ is —C(O)N($R_7$)($R_8$) and one or both of $R_7$ or $R_8$ are $C_3$-$C_8$-cycloalkyl. In certain embodiments, both of $R_7$ and $R_8$ are $C_3$-$C_8$-cycloalkyl. In certain embodiments, both of $R_7$ and $R_8$ are cyclohexyl.

In certain embodiments, $R_2$ is —C(O)N($R_7$)($R_8$) and one of $R_7$ or $R_8$ is $C_1$-$C_6$ alkyl and the other of $R_7$ or $R_8$ is aryl. In certain embodiments, one of $R_7$ or $R_8$ is phenyl and the other of $R_7$ or $R_8$ is ethyl.

In certain embodiments, $R_2$ is dialkyl carbamoyl. In certain embodiments, $R_2$ is dimethyl carbamoyl. In certain embodiments, $R_2$ is diethyl carbamoyl. In certain embodiments, $R_2$ is dipropyl carbamoyl. In certain embodiments, $R_2$ is di(propan-2-yl)carbamoyl. In certain embodiments, $R_2$ is dibutyl carbamoyl. In certain embodiments, $R_2$ is bis(2-methylpropyl)carbamoyl. In certain embodiments, $R_2$ is N-butyl-N-ethylcarbamoyl.

In certain embodiments, $R_2$ is N-methyl-N-phenylcarbamoyl.

In certain embodiments, $R_2$ is dicyclohexylcarbamoyl.

In certain embodiments, $R_2$ is —C(O)N($R_7$)($R_8$) and $R_7$ and $R_8$ together with the nitrogen atom to which they are attached form an optionally substituted saturated or partially saturated heterocyclic ring. In certain embodiments, the heterocyclic ring is a non-aromatic ring. In certain embodiments, the heterocyclic ring is a pyrrolidine. In certain embodiments, the heterocyclic ring is a piperidine. In certain embodiments, the heterocyclic ring is a morpholine. In certain embodiments, the heterocyclic ring is an azepane.

In certain embodiments, $R_2$ is —$CH_2$-$A_1$.

In certain embodiments, $A_1$ is an unsubstituted phenyl. In certain embodiments, $R_2$ is unsubstituted benzyl.

In certain embodiments, $A_1$ is a phenyl substituted with one or more $R_4$. In certain embodiments, $R_4$ is haloalkyl. In certain embodiments, $R_4$ is trifluoromethyl. In certain embodiments, $R_4$ is halogen. In certain embodiments, $R_4$ is fluoro. In certain embodiments, $R_4$ is chloro. In certain embodiments, $R_4$ is an alkoxy, such as methoxy. In certain embodiments, $R_2$ is substituted benzyl. In certain embodiments, $R_2$ is trifluoromethylbenzyl. In certain embodiments, $R_2$ is trifluorobenzyl. In certain embodiments, $R_2$ is fluorobenzyl. In certain embodiments, $R_2$ is difluorobenzyl. In certain embodiments, $R_2$ is chlorobenzyl. In certain embodiments, $R_2$ is 4-methoxybenzyl.

In certain embodiments, $A_1$ is naphthalene. In certain embodiments, $A_1$ is benzothiazole.

In certain embodiments, both a and b are a double bond. In certain embodiments, at least one of a and b are a single bond. In certain embodiments, both a and b are a single bond.

In certain embodiments, $R_1$ is —C(O)$CH_3$ and $R_2$ is benzyl.

In certain embodiments, $R_1$ is —C(O)$CH_3$ and $R_2$ is

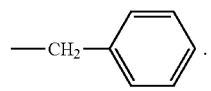

In certain embodiments, $R_1$ is —C(O)$CH_3$ and $R_2$ is trifluoromethylbenzyl.

In certain embodiments, $R_1$ is —C(O)$CH_3$ and $R_2$ is

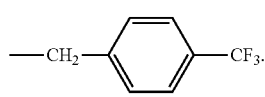

In certain embodiments, $R_1$ is —C(O)$CH_3$ and $R_2$ is fluorobenzyl.

In certain embodiments, $R_1$ is —C(O)$CH_3$ and $R_2$ is

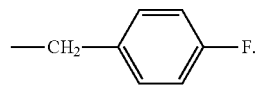

In certain embodiments, $R_1$ is —C(O)$CH_3$ and $R_2$ is chlorobenzyl.

In certain embodiments, $R_1$ is —C(O)$CH_3$ and $R_2$ is

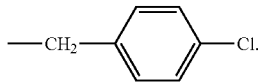

In certain embodiments, $R_1$ is —C(O)CH($CH_3$)$_2$ and $R_2$ is benzyl.

In certain embodiments, $R_1$ is —C(O)CH($CH_3$)$_2$ and $R_2$ is

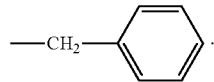

In certain embodiments, $R_1$ is —C(O)CH($CH_3$)$_2$ and $R_2$ is difluorobenzyl.

In certain embodiments, $R_1$ is —C(O)CH($CH_3$)$_2$ and $R_2$ is

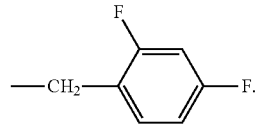

In certain embodiments, $R_1$ is —C(O)CH($CH_3$)$_2$ and $R_2$ is $CH_2$-benzothiazolyl.

In certain embodiments, $R_1$ is —C(O)CH($CH_3$)$_2$ and $R_2$ is

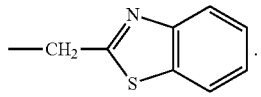

In certain embodiments, $R_1$ is —C(O)CH($CH_3$)$_2$ and $R_2$ is fluorobenzyl.

In certain embodiments, $R_1$ is —C(O)CH($CH_3$)$_2$ and $R_2$ is

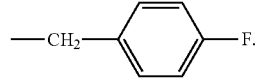

In certain embodiments, $R_1$ is —C(O)CH($CH_3$)$_2$ and $R_2$ is $CH_2$-naphthalenyl.

In certain embodiments, $R_1$ is —C(O)CH($CH_3$)$_2$ and $R_2$ is

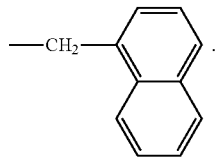

In certain embodiments, $R_1$ is hydrogen and $R_2$ is fluorobenzyl.

In certain embodiments, $R_1$ is hydrogen and $R_2$ is

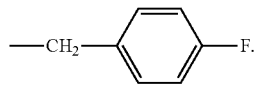

In certain embodiments, $R_1$ is —C(O)(CH$_2$)$_3$CH$_3$ and $R_2$ is fluorobenzyl.

In certain embodiments, $R_1$ is —C(O)(CH$_2$)$_3$CH$_3$ and $R_2$ is

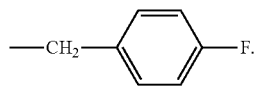

In certain embodiments, $R_1$ is —C(O)CH$_3$ and $R_2$ is —C(O)C(CH$_3$)$_3$.

In certain embodiments, $R_1$ is —C(O)CH(CH$_3$)$_2$ and $R_2$ is —C(O)C(CH$_3$)$_3$.

In certain embodiments, $R_1$ is hydrogen and $R_2$ is —C(O)C(CH$_3$)$_3$.

In certain embodiments, $R_1$ is —C(O)CH$_3$ and $R_2$ is —C(O)N(CH$_2$CH$_3$)$_2$.

In certain embodiments, $R_1$ is —C(O)CH$_3$ and $R_2$ is N-methyl-N-phenylcarbamoyl.

In certain embodiments, $R_1$ is —C(O)CH$_3$ and $R_2$ is —C(O)N(CH$_3$)(C$_6$H$_5$).

In certain embodiments, $R_1$ is —C(O)CH$_3$ and $R_2$ is —C(O)-pyrrolidinyl.

In certain embodiments, $R_1$ is —C(O)CH$_3$ and $R_2$ is

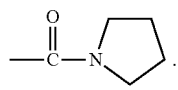

In certain embodiments, $R_1$ is —C(O)CH(CH$_3$)$_2$ and $R_2$ is —C(O)N(CH$_2$CH$_3$)$_2$.

In certain embodiments, $R_1$ is hydrogen and $R_2$ is —C(O)N(CH$_2$CH$_3$)$_2$.

In certain embodiments, $R_1$ is —C(O)CH$_3$ and $R_2$ is —C(O)-piperidinyl.

In certain embodiments, $R_1$ is —C(O)CH$_3$ and $R_2$ is

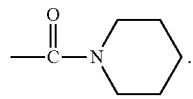

In certain embodiments, $R_1$ is —C(O)CH$_3$ and $R_2$ is —C(O)-morpholinyl.

In certain embodiments, $R_1$ is —C(O)CH$_3$ and $R_2$ is

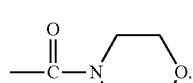

In certain embodiments, $R_1$ is —C(O)CH$_3$ and $R_2$ is —C(O)N(CH(CH$_3$)$_2$)$_2$.

In certain embodiments, $R_1$ is —C(O)CH$_3$ and $R_2$ is —C(O)N((CH$_2$)$_3$CH$_3$)$_2$.

In certain embodiments, $R_1$ is —C(O)CH$_3$ and $R_2$ is —C(O)N(CH$_2$CH(CH$_3$)$_2$)$_2$.

In certain embodiments, $R_1$ is —C(O)CH$_3$ and $R_2$ is —C(O)-azepane.

In certain embodiments, $R_1$ is —C(O)CH$_3$ and $R_2$ is

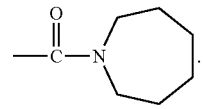

In certain embodiments, $R_1$ is —C(O)CH$_3$ and $R_2$ is dicyclohexylcarbamoyl.

In certain embodiments, $R_1$ is —C(O)CH$_3$ and $R_2$ is

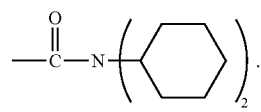

In certain embodiments, $R_1$ is —C(O)CH(CH$_3$)$_2$ and $R_2$ is —C(O)N(CH$_3$)$_2$.

In certain embodiments, $R_1$ is —C(O)CH(CH$_3$)$_2$ and $R_2$ is N-butyl-N-ethylcarbamoyl.

In certain embodiments, $R_1$ is —C(O)CH(CH$_3$)$_2$ and $R_2$ is —C(O)N(CH$_2$CH$_3$)((CH$_2$)$_3$CH$_3$).

In certain embodiments, $R_1$ is hydrogen and $R_2$ is —C(O)N(CH(CH$_3$)$_2$)$_2$.

In certain embodiments, $R_1$ is hydrogen and $R_2$ is —C(O)N((CH$_2$)$_3$CH$_3$)$_2$.

In certain embodiments, $R_1$ is hydrogen and $R_2$ is dicyclohexylcarbamoyl.

In certain embodiments, $R_1$ is H and $R_2$ is

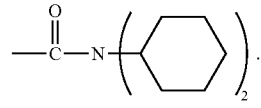

In certain embodiments, $R_1$ is —C(O)CH(CH$_3$)$_2$ and $R_2$ is —C(O)-morpholinyl.

In certain embodiments, $R_1$ is —C(O)CH(CH$_3$)$_2$ and $R_2$ is

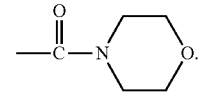

In certain embodiments, $R_1$ is —C(O)CH$_3$ and $R_2$ is difluorobenzyl.

In certain embodiments, $R_1$ is —C(O)CH$_3$ and $R_2$ is

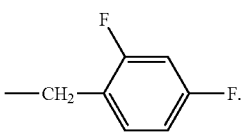

In certain embodiments, $R_1$ is —C(O)(CH$_2$)$_3$(CH$_3$) and $R_2$ is —C(O)-morpholinyl.

In certain embodiments, $R_1$ is —C(O)(CH$_2$)$_3$(CH$_3$) and $R_2$ is

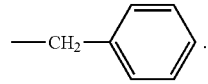

In certain embodiments, $R_1$ is —C(O)(CH$_2$)$_3$(CH$_3$) and $R_2$ is difluorobenzyl.

In certain embodiments, $R_1$ is —C(O)(CH$_2$)$_3$(CH$_3$) and $R_2$ is

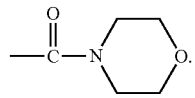

In certain embodiments, $R_1$ is hydrogen and $R_2$ is —C(O)-morpholinyl.

In certain embodiments, $R_1$ is hydrogen and $R_2$ is

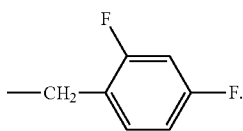

In certain embodiments, $R_1$ is hydrogen and $R_2$ is difluorobenzyl.

In certain embodiments, $R_1$ is hydrogen and $R_2$ is

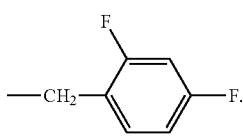

In certain embodiments, $R_1$ is hydrogen and $R_2$ is benzyl.

In certain embodiments, $R_1$ is hydrogen and $R_2$ is

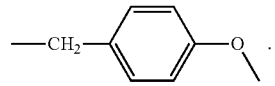

In certain embodiments, $R_1$ is hydrogen and $R_2$ is methoxybenzyl.

In certain embodiments, $R_1$ is hydrogen and $R_2$ is

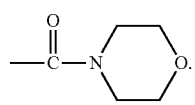

In one aspect, the present methods employ a compound of Formula (II):

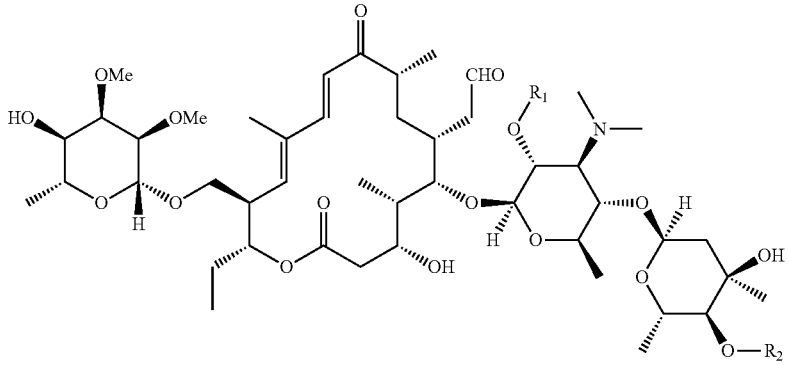

(II)

and salts thereof, wherein $R_1$ and $R_2$ are as defined above.

In particular, $R_1$ represents hydrogen or —C(O)R$_3$, wherein $R_3$ represents C$_1$-C$_6$-alkyl; and $R_2$ represents —C(O)C(R$_4$)(R$_5$)(R$_6$), wherein $R_4$ is selected from the group consisting of hydrogen, C$_1$-C$_6$-alkyl, C$_1$-C$_6$-haloalkyl, aryl, heteroaryl, C$_3$-C$_8$-cycloalkyl, heterocycloalkyl, arylalkyl, heteroarylalkyl, and C$_3$-C$_8$-cycloalkyl-C$_1$-C$_4$-alkyl; and each of $R_5$ and $R_6$ are independently selected from the group consisting of C$_1$-C$_6$-alkyl, C$_1$-C$_6$-haloalkyl, aryl, heteroaryl, C$_3$-C$_8$-cycloalkyl, heterocycloalkyl, arylalkyl, heteroarylalkyl, and C$_3$-C$_8$-cycloalkyl-C$_1$-C$_4$-alkyl; or $R_2$ represents —C(O)N(R$_7$)(R$_8$), wherein each of $R_7$ and $R_8$ are independently selected from the group consisting of C$_1$-C$_6$-alkyl, C$_1$-C$_6$-haloalkyl, aryl, heteroaryl, C$_3$-C$_8$-cycloalkyl, heterocycloalkyl, arylalkyl, heteroarylalkyl, and C$_3$-C$_8$-cycloalkyl-C$_1$-C$_4$-alkyl, or $R_7$ and $R_8$ together with the nitrogen atom to which they are attached form an optionally substituted saturated or partially saturated heterocyclic ring; or $R_2$ represents —CH$_2$-A$_1$, wherein A$_1$ represents a 6- to 10-membered aryl or a 5- to 10-membered heteroaryl and A$_1$ is unsubstituted or substituted with one or more R$_A$, wherein each R$_A$ is independently selected from the group consisting of halogen, C$_1$-C$_6$-alkyl, C$_1$-C$_6$-haloalkyl, and —O—R$_9$, where R$_9$ represents C$_1$-C$_6$-alkyl.

In certain embodiments, $R_1$ is hydrogen.

In certain embodiments, $R_1$ is —C(O)R$_3$. In certain embodiments, $R_3$ is C$_1$-C$_6$-alkyl, such as methyl; ethyl;

propyl, such as n-propyl or isopropyl; or butyl, such as n-butyl, isobutyl, or tert-butyl.

In certain embodiments, $R_2$ is —C(O)C($R_4$)($R_5$)($R_6$). In certain embodiments, $R_4$ is hydrogen. In certain embodiments, each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_5$ is $C_1$-$C_6$ alkyl. In certain embodiments, $R_6$ is $C_1$-$C_6$ alkyl. In certain embodiments, each of $R_4$, $R_5$, and $R_6$ are $C_1$-$C_6$ alkyl.

In certain embodiments, each of $R_4$, $R_5$, and $R_6$ are $C_1$-$C_6$-alkyl. In certain embodiments, $R_4$, $R_5$, and $R_6$ are the same. For example, in certain embodiments, each of $R_4$, $R_5$, and $R_6$ are methyl. In certain embodiments, at least two of $R_4$, $R_5$, and $R_6$ are the same. In certain embodiments, $R_4$, $R_5$, and $R_6$ are different.

In certain embodiments, $R_2$ is —C(O)N($R_7$)($R_8$). In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

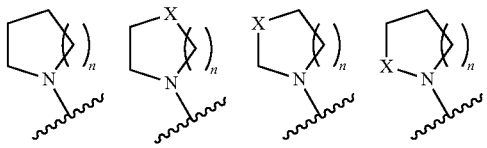

where X is O, S, or N($R_B$). $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_2$ is —$CH_2$-$A_1$ and $A_1$ is a 6- to 10-membered aryl or a 5- to 10-membered heteroaryl. In certain embodiments, $A_1$ is phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

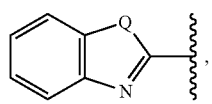

where Q is O, S, or N($R_C$). $R_C$ is selected from hydrogen, $C_1$-$C_6$-alkyl, or $C_1$-$C_6$-haloalkyl.

In certain embodiments, $A_1$ is unsubstituted. In certain embodiments, $A_1$ is substituted with one or more $R_A$. $R_A$ is independently selected at each occurrence from the group consisting of halogen, $C_1$-$C_6$-alkyl, $C_1$-$C_6$-haloalkyl, and —O—$R_9$, where $R_9$ represents $C_1$-$C_6$-alkyl. In certain embodiments, $R_A$ is independently selected at each occurrence from the group consisting of halogen, $C_1$-$C_6$-alkyl, and $C_1$-$C_6$-haloalkyl. In certain embodiments, $R_A$ is halogen. In certain embodiments, $R_A$ is fluoro. In certain embodiments, $R_A$ is chloro. In certain embodiments, $R_A$ is —O—$R_9$. In certain embodiments, $R_A$ is —O—$R_9$ and $R_9$ is methyl. In certain embodiments, $R_A$ is an alkoxy, such as methoxy.

In certain embodiments, $R_1$ is —C(O)$R_3$ and $R_3$ is $C_1$-$C_6$-alkyl. In certain embodiments, $R_3$ is methyl. In certain embodiments, $R_3$ is propyl. In certain embodiments, $R_3$ is n-propyl. In certain embodiments, $R_3$ is isopropyl. In certain embodiments, $R_3$ is butyl. In certain embodiments, $R_3$ is n-butyl. In certain embodiments, $R_3$ is isobutyl. In certain embodiments, $R_3$ is tert-butyl.

In certain embodiments, $R_2$ is —C(O)C($R_4$)($R_5$)($R_6$) and each of $R_4$, $R_5$, and $R_6$ are $C_1$-$C_6$ alkyl. In certain embodiments, $R_4$ is methyl. In certain embodiments, $R_5$ is methyl. In certain embodiments, $R_6$ is methyl. In certain embodiments, each of $R_4$, $R_5$, and $R_6$ are methyl.

In certain embodiments, $R_2$ is —C(O)N($R_7$)($R_8$) and one or both of $R_7$ or $R_8$ are $C_1$-$C_6$ alkyl. In certain embodiments, one or both of $R_7$ or $R_8$ are methyl. In certain embodiments, one or both of $R_7$ or $R_8$ are ethyl. In certain embodiments, one or both of $R_7$ or $R_8$ are propyl, such as n-propyl or isopropyl. In certain embodiments, one or both of $R_7$ or $R_8$ are butyl, such as n-butyl, isobutyl, or sec-butyl.

In certain embodiments, $R_2$ is —C(O)N($R_7$)($R_8$) and each of $R_7$ and $R_8$ are $C_1$-$C_6$ alkyl. In certain embodiments, both of $R_7$ and $R_8$ are methyl. In certain embodiments, both of $R_7$ and $R_8$ are ethyl. In certain embodiments, both of $R_7$ and $R_8$ are propyl, such as n-propyl or isopropyl. In certain embodiments, both of $R_7$ and $R_8$ are butyl, such as n-butyl, isobutyl, or sec-butyl. In certain embodiments, one of $R_7$ or $R_8$ is butyl and the other of $R_7$ or $R_8$ is ethyl.

In certain embodiments, $R_2$ is —C(O)N($R_7$)($R_8$) and one or both of $R_7$ or $R_8$ are $C_3$-$C_8$-cycloalkyl. In certain embodiments, both of $R_7$ and $R_8$ are $C_3$-$C_8$-cycloalkyl. In certain embodiments, both of $R_7$ and $R_8$ are cyclohexyl.

In certain embodiments, $R_2$ is —C(O)N($R_7$)($R_8$) and one of $R_7$ or $R_8$ is $C_1$-$C_6$ alkyl and the other of $R_7$ or $R_8$ is aryl. In certain embodiments, one of $R_7$ or $R_8$ is phenyl and the other of $R_7$ or $R_8$ is ethyl. In certain embodiments, $R_1$ is —C(O)$CH_3$ and $R_2$ is benzyl.

In certain embodiments, $R_1$ is —C(O)$CH_3$ and $R_2$ is

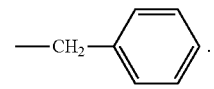

In certain embodiments, $R_1$ is —C(O)$CH_3$ and $R_2$ is trifluoromethylbenzyl.

In certain embodiments, $R_1$ is —C(O)$CH_3$ and $R_2$ is

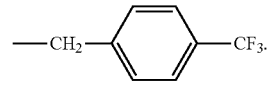

In certain embodiments, $R_1$ is —C(O)$CH_3$ and $R_2$ is fluorobenzyl.

In certain embodiments, $R_1$ is —C(O)$CH_3$ and $R_2$ is

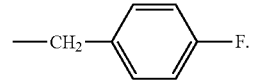

In certain embodiments, R₁ is —C(O)CH₃ and R₂ is chlorobenzyl.

In certain embodiments, R₁ is —C(O)CH₃ and R₂ is

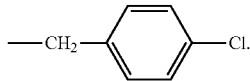

In certain embodiments, R₁ is —C(O)CH(CH₃)₂ and R₂ is benzyl.

In certain embodiments, R₁ is —C(O)CH(CH₃)₂ and R₂ is

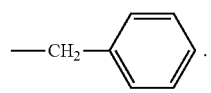

In certain embodiments, R₁ is —C(O)CH(CH₃)₂ and R₂ is difluorobenzyl.

In certain embodiments, R₁ is —C(O)CH(CH₃)₂ and R₂ is

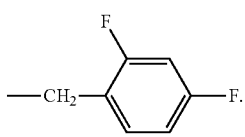

In certain embodiments, R₁ is —C(O)CH(CH₃)₂ and R₂ is CH₂-benzothiazolyl.

In certain embodiments, R₁ is —C(O)CH(CH₃)₂ and R₂ is

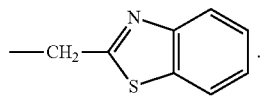

In certain embodiments, R₁ is —C(O)CH(CH₃)₂ and R₂ is fluorobenzyl.

In certain embodiments, R₁ is —C(O)CH(CH₃)₂ and R₂ is

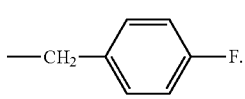

In certain embodiments, R₁ is —C(O)CH(CH₃)₂ and R₂ is CH₂-naphthalenyl.

In certain embodiments, R₁ is —C(O)CH(CH₃)₂ and R₂ is

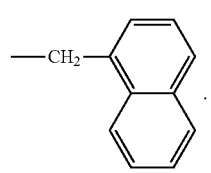

In certain embodiments, R₁ is hydrogen and R₂ is fluorobenzyl.

In certain embodiments, R₁ is hydrogen and R₂ is

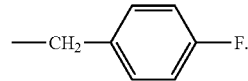

In certain embodiments, R₁ is —C(O)(CH₂)₃CH₃ and R₂ is fluorobenzyl.

In certain embodiments, R₁ is —C(O)(CH₂)₃CH₃ and R₂ is

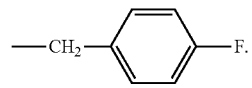

In certain embodiments, R₁ is —C(O)CH₃ and R₂ is —C(O)C(CH₃)₃.

In certain embodiments, R₁ is —C(O)CH(CH₃)₂ and R₂ is —C(O)C(CH₃)₃.

In certain embodiments, R₁ is hydrogen and R₂ is —C(O)C(CH₃)₃.

In certain embodiments, R₁ is —C(O)CH₃ and R₂ is —C(O)N(CH₂CH₃)₂.

In certain embodiments, R₁ is —C(O)CH₃ and R₂ is N-methyl-N-phenylcarbamoyl.

In certain embodiments, R₁ is —C(O)CH₃ and R₂ is —C(O)N(CH₃)(C₆H₅).

In certain embodiments, R₁ is —C(O)CH₃ and R₂ is —C(O)-pyrrolidinyl.

In certain embodiments, R₁ is —C(O)CH₃ and R₂ is

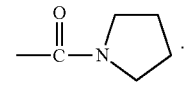

In certain embodiments, R₁ is —C(O)CH(CH₃)₂ and R₂ is —C(O)N(CH₂CH₃)₂.

In certain embodiments, R₁ is hydrogen and R₂ is —C(O)N(CH₂CH₃)₂.

In certain embodiments, R₁ is —C(O)CH₃ and R₂ is —C(O)-piperidinyl.

In certain embodiments, R₁ is —C(O)CH₃ and R₂ is

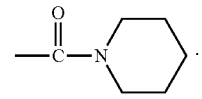

In certain embodiments, R₁ is —C(O)CH₃ and R₂ is —C(O)-morpholinyl.

In certain embodiments, R₁ is —C(O)CH₃ and R₂ is

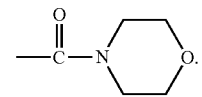

In certain embodiments, R₁ is —C(O)CH₃ and R₂ is —C(O)N(CH(CH₃)₂)₂.

In certain embodiments, R₁ is —C(O)CH₃ and R₂ is —C(O)N((CH₂)₃CH₃)₂.

In certain embodiments, $R_1$ is —C(O)CH$_3$ and $R_2$ is —C(O)N(CH$_2$CH(CH$_3$)$_2$)$_2$.

In certain embodiments, $R_1$ is —C(O)CH$_3$ and $R_2$ is —C(O)-azepane.

In certain embodiments, $R_1$ is —C(O)CH$_3$ and $R_2$ is

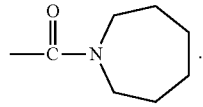

In certain embodiments, $R_1$ is —C(O)CH$_3$ and $R_2$ is dicyclohexylcarbamoyl.

In certain embodiments, $R_1$ is —C(O)CH$_3$ and $R_2$ is

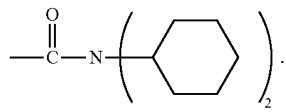

In certain embodiments, $R_1$ is —C(O)CH(CH$_3$)$_2$ and $R_2$ is —C(O)N(CH$_3$)$_2$.

In certain embodiments, $R_1$ is —C(O)CH(CH$_3$)$_2$ and $R_2$ is N-butyl-N-ethylcarbamoyl.

In certain embodiments, $R_1$ is —C(O)CH(CH$_3$)$_2$ and $R_2$ is —C(O)N(CH$_2$CH$_3$)((CH$_2$)$_3$CH$_3$).

In certain embodiments, $R_1$ is hydrogen and $R_2$ is —C(O)N(CH(CH$_3$)$_2$)$_2$.

In certain embodiments, $R_1$ is hydrogen and $R_2$ is —C(O)N((CH$_2$)$_3$CH$_3$)$_2$.

In certain embodiments, $R_1$ is hydrogen and $R_2$ is dicyclohexylcarbamoyl.

In certain embodiments, $R_1$ is H and $R_2$ is

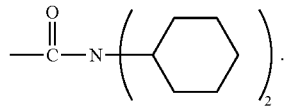

In certain embodiments, $R_1$ is —C(O)CH(CH$_3$)$_2$ and $R_2$ is —C(O)-morpholinyl.

In certain embodiments, $R_1$ is —C(O)CH(CH$_3$)$_2$ and $R_2$ is

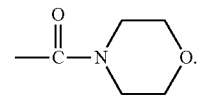

In certain embodiments, $R_1$ is —C(O)CH$_3$ and $R_2$ is difluorobenzyl.

In certain embodiments, $R_1$ is —C(O)CH$_3$ and $R_2$ is

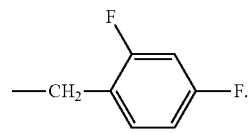

In certain embodiments, $R_1$ is —C(O)(CH$_2$)$_3$(CH$_3$) and $R_2$ is —C(O)-morpholinyl.

In certain embodiments, $R_1$ is —C(O)(CH$_2$)$_3$(CH$_3$) and $R_2$ is

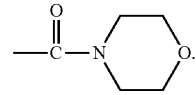

In certain embodiments, $R_1$ is —C(O)(CH$_2$)$_3$(CH$_3$) and $R_2$ is difluorobenzyl.

In certain embodiments, $R_1$ is —C(O)(CH$_2$)$_3$(CH$_3$) and $R_2$ is

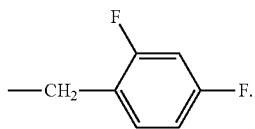

In certain embodiments, $R_1$ is hydrogen and $R_2$ is —C(O)-morpholinyl.

In certain embodiments, $R_1$ is hydrogen and $R_2$ is

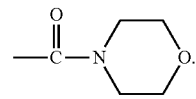

In certain embodiments, $R_1$ is hydrogen and $R_2$ is difluorobenzyl.

In certain embodiments, $R_1$ is hydrogen and $R_2$ is

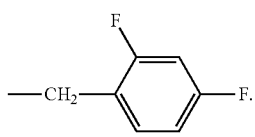

In certain embodiments, $R_1$ is hydrogen and $R_2$ is benzyl.

In certain embodiments, $R_1$ is hydrogen and $R_2$ is

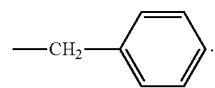

In certain embodiments, $R_1$ is hydrogen and $R_2$ is methoxybenzyl.

In certain embodiments, $R_1$ is hydrogen and $R_2$ is

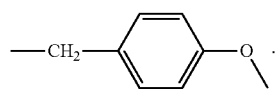

In certain embodiments, a compound of Formula (II) is synthesized as described herein. For example, a compound of Formula (II) can be synthesized as described in the Schemes or Examples described herein. In certain other embodiments, a compound of Formula (II) is generated in vivo following administration of a suitable prodrug. In certain embodiments, a suitable prodrug may include a 4‴-O-acyl moiety (e.g., a 4‴-O-acetyl, 4‴-O-propionyl, or 4‴-O-methylpropionyl moiety.

In one aspect, the present methods employ a compound of Formula (III):

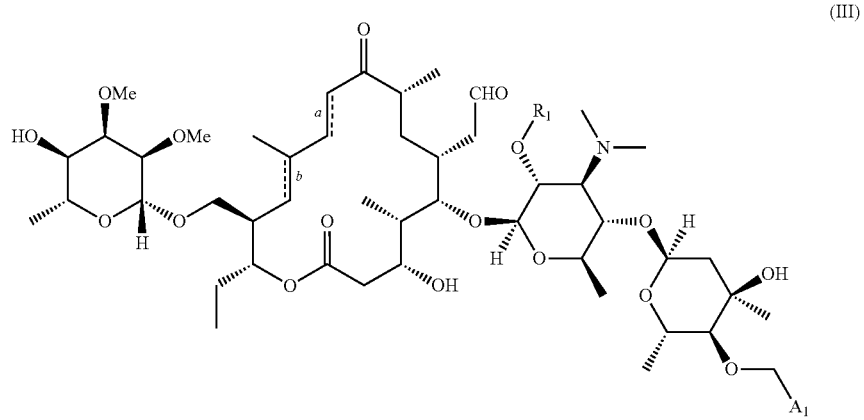

(III)

and salts thereof, wherein:

$R_1$ represents hydrogen or —C(O)$R_3$, where $R_3$ represents $C_1$-$C_6$-alkyl;

$A_1$ represents a 6- to 10-membered aryl or a 5- to 10-membered heteroaryl and $A_1$ is unsubstituted or substituted with one or more $R_A$, wherein each $R_A$ is independently selected from the group consisting of halogen, $C_1$-$C_6$-alkyl, $C_1$-$C_6$-haloalkyl, and —O—$R_9$, where $R_9$ represents $C_1$-$C_6$-alkyl; and each of a and b independently represents either a single bond or a double bond.

In certain embodiments, $R_1$ is hydrogen.

In certain embodiments, $R_1$ is —C(O)$R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl.

In certain embodiments, $A_1$ is a phenyl substituted with one or more $R_A$. In certain embodiments, $R_A$ is halogen. In certain embodiments, $A_1$ is a halophenyl or a dihalophenyl. In certain embodiments, $A_1$ is a 7- to 10-membered aryl optionally substituted with one or more $R_A$. In certain embodiments, $A_1$ is a 5- to 10-membered heteroaryl optionally substituted with one or more $R_A$. In certain embodiments, each $R_A$ independently is selected from the group consisting of halogen, $C_1$-$C_6$-alkyl, and $C_1$-$C_6$-haloalkyl. In certain embodiments, $A_1$ is substituted phenyl or an optionally substituted pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

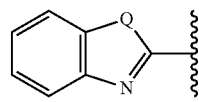

where Q is O, S, or N($R_C$). $R_C$ is selected from hydrogen, $C_1$-$C_6$-alkyl, or $C_1$-$C_6$-haloalkyl.

In certain embodiments, $A_1$ is substituted with one or more $R_A$. $R_A$ is independently selected at each occurrence from the group consisting of halogen, $C_1$-$C_6$-alkyl, $C_1$-$C_6$-haloalkyl, and —O—$R_9$, where $R_9$ represents $C_1$-$C_6$-alkyl. In certain embodiments, $R_A$ is independently selected at each occurrence from the group consisting of halogen, $C_1$-$C_6$-alkyl, and $C_1$-$C_6$-haloalkyl. In certain embodiments, $R_A$ is halogen. In certain embodiments, $R_A$ is fluoro. In certain embodiments, $R_A$ is chloro. In certain embodiments, $R_A$ is —O—$R_9$. In certain embodiments, $R_A$ is —O—$R_9$ and $R_9$ is methyl.

In certain embodiments, $A_1$ is unsubstituted phenyl. In certain embodiments, $A_1$ is a phenyl substituted with one or more $R_A$. In certain embodiments, $R_A$ is haloalkyl. In certain embodiments, $R_A$ is trifluoromethyl. In certain embodiments, $R_A$ is halogen. In certain embodiments, $R_A$ is fluoro. In certain embodiments, $R_A$ is chloro. In certain embodiments, $R_A$ is an alkoxy, such as methoxy. In certain embodiments, $A_1$ is fluorophenyl. In certain embodiments, $A_1$ is chlorophenyl. In certain embodiments, $A_1$ is 4-methoxyphenyl.

In certain embodiments, $A_1$ is a phenyl substituted with two or more $R_A$. In certain embodiments, each of the two or more $R_A$ is halogen. In certain embodiments, each of the two or more $R_A$ is fluoro. In certain embodiments, each of the two or more $R_A$ is chloro. In certain embodiments, $A_1$ is dihalophenyl. In certain embodiments, $A_1$ is difluorophenyl. In certain embodiments, $A_1$ is dichlorophenyl.

In certain embodiments, $A_1$ is a 7- to 10-membered aryl optionally substituted with one or more $R_A$. In certain embodiments, $A_1$ is naphthalene.

In certain embodiments, $A_1$ is a 5- to 10-membered heteroaryl optionally substituted with one or more $R_A$. In certain embodiments, $A_1$ is benzothiazole.

In certain embodiments, both a and b are a double bond. In certain embodiments, at least one of a and b are a single bond. In certain embodiments, both a and b are a single bond.

In one aspect, the present methods employ a compound of Formula (IV):

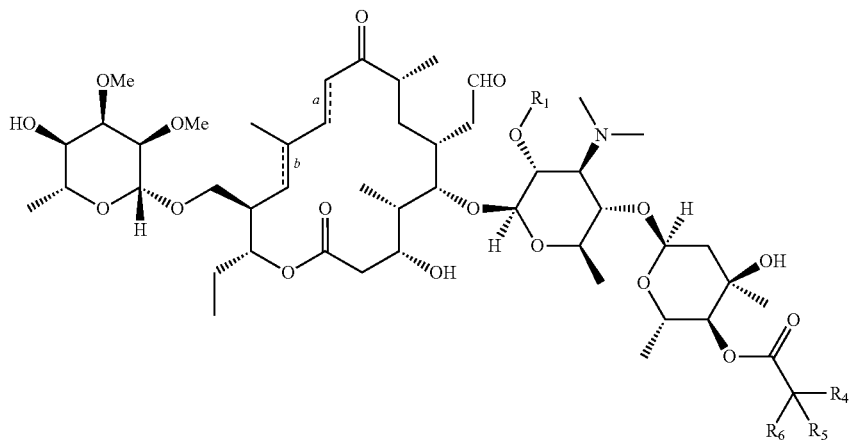

(IV)

and salts thereof, wherein:

$R_1$ represents hydrogen or —C(O)$R_3$, where $R_3$ represents $C_1$-$C_6$-alkyl;

$R_4$ is selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl;

each of $R_5$ and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; and each of a and b independently represents either a single bond or a double bond.

In certain embodiments, $R_1$ is hydrogen.

In certain embodiments, $R_1$ is —C(O)$R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl.

In certain embodiments, $R_4$ is hydrogen.

In certain embodiments, each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_4$ is methyl. In certain embodiments, $R_5$ is $C_1$-$C_6$ alkyl. In certain embodiments, $R_5$ is methyl. In certain embodiments, $R_6$ is $C_1$-$C_6$ alkyl. In certain embodiments, $R_6$ is methyl. In certain embodiments, each of $R_4$, $R_5$, and $R_6$ are $C_1$-$C_6$ alkyl.

In certain embodiments, $R_4$, $R_5$, and $R_6$ are the same. For example, in certain embodiments, each of $R_4$, $R_5$, and $R_6$ are methyl. In certain embodiments, at least two of $R_4$, $R_5$, and $R_6$ are the same. In certain embodiments, $R_4$, $R_5$, and $R_6$ are different.

In certain embodiments, both a and b are a double bond. In certain embodiments, at least one of a and b are a single bond. In certain embodiments, both a and b are a single bond.

In one aspect, the present methods employ a compound of Formula (V):

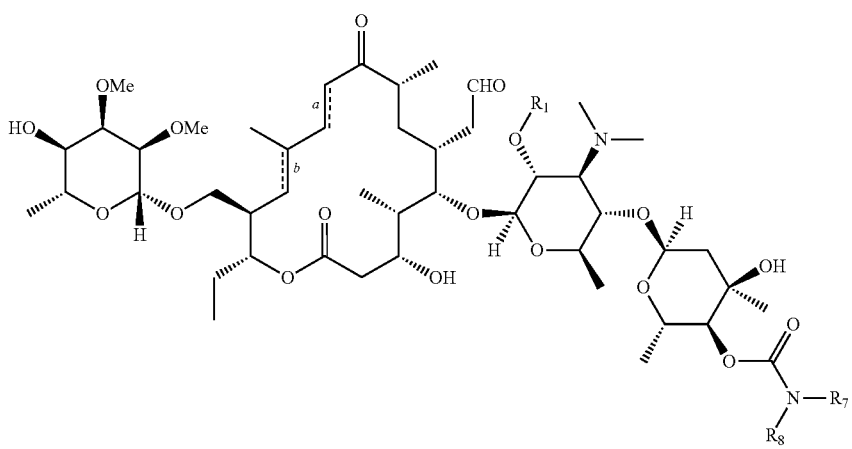

(V)

and salts thereof, wherein:

$R_1$ represents hydrogen or —C(O)$R_3$, where $R_3$ represents $C_1$-$C_6$-alkyl;

each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; and each of a and b independently represents either a single bond or a double bond.

In certain embodiments, $R_1$ is hydrogen.

In certain embodiments, $R_1$ is —C(O)$R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl.

In certain embodiments, $R_2$ is —C(O)N($R_7$)($R_8$). In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

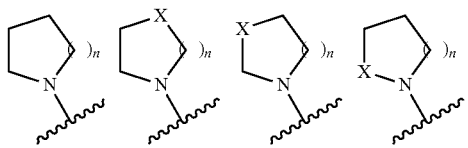

where X is O, S, or N($R_B$). $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_1$ is —C(O)$R_3$. In certain embodiments, $R_3$ is methyl. In certain embodiments, $R_3$ is propyl. In certain embodiments, $R_3$ is n-propyl. In certain embodiments, $R_3$ is isopropyl. In certain embodiments, $R_3$ is butyl. In certain embodiments, $R_3$ is n-butyl. In certain embodiments, $R_3$ is isobutyl. In certain embodiments, $R_3$ is tert-butyl.

In certain embodiments, one or both of $R_7$ or $R_8$ are $C_1$-$C_6$ alkyl. In certain embodiments, one or both of $R_7$ or $R_8$ are methyl. In certain embodiments, one or both of $R_7$ or $R_8$ are ethyl. In certain embodiments, one or both of $R_7$ or $R_8$ are propyl, such as n-propyl or isopropyl. In certain embodiments, one or both of $R_7$ or $R_8$ are butyl, such as n-butyl, isobutyl, or sec-butyl.

In certain embodiments, both of $R_7$ and $R_8$ are $C_1$-$C_6$ alkyl. In certain embodiments, both of $R_7$ and $R_8$ are methyl. In certain embodiments, both of $R_7$ and $R_8$ are ethyl. In certain embodiments, both of $R_7$ and $R_8$ are propyl, such as n-propyl or isopropyl. In certain embodiments, both of $R_7$ and $R_8$ are butyl, such as n-butyl, isobutyl, or sec-butyl. In certain embodiments, one of $R_7$ or $R_8$ is butyl and the other of $R_7$ or $R_8$ is ethyl.

In certain embodiments, one or both of $R_7$ or $R_8$ are $C_3$-$C_8$-cycloalkyl. In certain embodiments, both of $R_7$ and $R_8$ are $C_3$-$C_8$-cycloalkyl. In certain embodiments, both of $R_7$ and $R_8$ are cyclohexyl.

In certain embodiments, one or both of $R_7$ or $R_8$ are aryl. In certain embodiments, one or both of $R_7$ or $R_8$ are phenyl. In certain embodiments, one or both of $R_7$ or $R_8$ are unsubstituted phenyl.

In certain embodiments, one of $R_7$ or $R_8$ is $C_1$-$C_6$ alkyl and the other of $R_7$ or $R_8$ is aryl. In certain embodiments, one of $R_7$ or $R_8$ is phenyl and the other of $R_7$ or $R_8$ is methyl or ethyl. In certain embodiments, one of $R_7$ or $R_8$ is unsubstituted phenyl and the other of $R_7$ or $R_8$ is methyl.

In certain embodiments, $R_7$ and $R_8$ together with the nitrogen atom to which they are attached form an optionally substituted saturated or partially saturated heterocyclic ring. In certain embodiments, the heterocyclic ring is a non-aromatic ring. In certain embodiments, the heterocyclic ring is a pyrrolidine. In certain embodiments, the heterocyclic ring is a piperidine. In certain embodiments, the heterocyclic ring is a morpholine. In certain embodiments, the heterocyclic ring is an azepane.

In certain embodiments, both a and b are a double bond. In certain embodiments, at least one of a and b are a single bond. In certain embodiments, both a and b are a single bond.

In one aspect, the present methods employ a compound of Formula (VI):

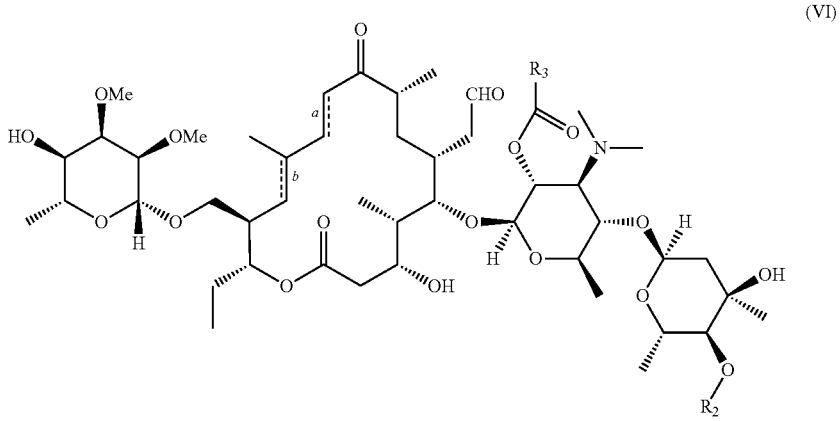

(VI)

and salts thereof, wherein:

$R_3$ represents $C_1$-$C_6$-alkyl;

$R_2$ represents —C(O)C($R_4$)($R_5$)($R_6$), wherein each of $R_4$, $R_5$, and $R_6$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —$CH_2$-$A_1$, wherein $A_1$ represents a 6- to 10-membered aryl or a 5- to 10-membered heteroaryl and $A_1$ is unsubstituted or substituted with one or more $R_A$, wherein each $R_A$ is independently selected from the group consisting of halogen, $C_1$-$C_6$-alkyl, $C_1$-$C_6$-haloalkyl, and —O—$R_9$, where $R_9$ represents $C_1$-$C_6$-alkyl; and each of a and b independently represents either a single bond or a double bond.

In certain embodiments, $R_3$ is methyl. In certain embodiments, $R_3$ is ethyl. In certain embodiments, $R_3$ is propyl, such as isopropyl. In certain embodiments, $R_3$ is butyl, such as n-butyl.

In certain embodiments, $R_2$ is —$C(O)C(R_4)(R_5)(R_6)$. Each of $R_4$, $R_5$, and $R_6$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_5$ is $C_1$-$C_6$ alkyl. In certain embodiments, $R_6$ is $C_1$-$C_6$ alkyl. In certain embodiments, each of $R_4$, $R_5$, and $R_6$ are $C_1$-$C_6$ alkyl.

In certain embodiments, $R_2$ is —$C(O)N(R_7)(R_8)$. In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

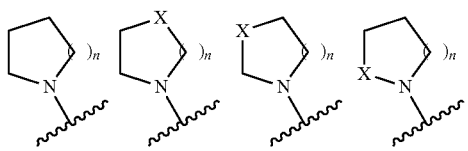

where X is O, S, or $N(R_B)$. $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_2$ is —$CH_2$-$A_1$. $A_1$ is a 6- to 10-membered aryl or a 5- to 10-membered heteroaryl. In certain embodiments, $A_1$ is phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

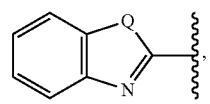

where Q is O, S, or $N(R_C)$. $R_C$ is selected from hydrogen, $C_1$-$C_6$-alkyl, or $C_1$-$C_6$-haloalkyl.

In certain embodiments, $A_1$ is unsubstituted. In certain embodiments, $A_1$ is substituted with one or more $R_A$. In certain embodiments, $R_A$ is halogen, $C_1$-$C_6$-alkyl, $C_1$-$C_6$-haloalkyl, or —O—$R_9$. In certain embodiments, $R_A$ is —O—$R_9$ and $R_9$ is $C_1$-$C_6$-alkyl. In certain embodiments, $R_A$ is halogen, $C_1$-$C_6$-alkyl, or $C_1$-$C_6$-haloalkyl.

In certain embodiments, $R_2$ is —$C(O)C(R_4)(R_5)(R_6)$ and each of $R_4$, $R_5$, and $R_6$ are $C_1$-$C_6$ alkyl. In certain embodiments, $R_4$ is methyl. In certain embodiments, $R_5$ is methyl. In certain embodiments, $R_6$ is methyl. In certain embodiments, each of $R_4$, $R_5$, and $R_6$ are methyl.

In certain embodiments, $R_2$ is —$C(O)N(R_7)(R_8)$ and one or both of $R_7$ or $R_8$ are $C_1$-$C_6$ alkyl. In certain embodiments, one or both of $R_7$ or $R_8$ are methyl. In certain embodiments, one or both of $R_7$ or $R_8$ are ethyl. In certain embodiments, one or both of $R_7$ or $R_8$ are propyl, such as n-propyl or isopropyl. In certain embodiments, one or both of $R_7$ or $R_8$ are butyl, such as n-butyl, isobutyl, or sec-butyl.

In certain embodiments, $R_2$ is —$C(O)N(R_7)(R_8)$ and each of $R_7$ and $R_8$ are $C_1$-$C_6$ alkyl. In certain embodiments, both of $R_7$ and $R_8$ are methyl. In certain embodiments, both of $R_7$ and $R_8$ are ethyl. In certain embodiments, both of $R_7$ and $R_8$ are propyl, such as n-propyl or isopropyl. In certain embodiments, both of $R_7$ and $R_8$ are butyl, such as n-butyl, isobutyl, or sec-butyl. In certain embodiments, one of $R_7$ or $R_8$ is butyl and the other of $R_7$ or $R_8$ is ethyl.

In certain embodiments, $R_2$ is —$C(O)N(R_7)(R_8)$ and one or both of $R_7$ or $R_8$ are $C_3$-$C_8$-cycloalkyl. In certain embodiments, both of $R_7$ and $R_8$ are $C_3$-$C_8$-cycloalkyl. In certain embodiments, both of $R_7$ and $R_8$ are cyclohexyl.

In certain embodiments, $R_2$ is —$C(O)N(R_7)(R_8)$ and one or both of $R_7$ or $R_8$ are aryl. In certain embodiments, one or both of $R_7$ or $R_8$ are optionally substituted phenyl. In certain embodiments, one or both of $R_7$ or $R_8$ are unsubstituted phenyl.

In certain embodiments, $R_2$ is —$C(O)N(R_7)(R_8)$ and one of $R_7$ or $R_8$ is $C_1$-$C_6$ alkyl and the other of $R_7$ or $R_8$ is aryl. In certain embodiments, one of $R_7$ or $R_8$ is optionally substituted phenyl and the other of $R_7$ or $R_8$ is methyl or ethyl. In certain embodiments, one of $R_7$ or $R_8$ is unsubstituted phenyl and the other of $R_7$ or $R_8$ is methyl.

In certain embodiments, $R_2$ is dialkyl carbamoyl. In certain embodiments, $R_2$ is dimethyl carbamoyl. In certain embodiments, $R_2$ is diethyl carbamoyl. In certain embodiments, $R_2$ is dipropyl carbamoyl. In certain embodiments, $R_2$ is di(propan-2-yl)carbamoyl. In certain embodiments, $R_2$ is dibutyl carbamoyl. In certain embodiments, $R_2$ is bis(2-methylpropyl)carbamoyl. In certain embodiments, $R_2$ is N-butyl-N-ethylcarbamoyl.

In certain embodiments, $R_2$ is N-methyl-N-phenylcarbamoyl.

In certain embodiments, $R_2$ is dicyclohexylcarbamoyl.

In certain embodiments, $R_2$ is —$C(O)N(R_7)(R_8)$ and $R_7$ and $R_8$ together with the nitrogen atom to which they are attached form an optionally substituted saturated or partially saturated heterocyclic ring. In certain embodiments, the heterocyclic ring is a non-aromatic ring. In certain embodiments, the heterocyclic ring is a pyrrolidine. In certain embodiments, the heterocyclic ring is a piperidine. In certain embodiments, the heterocyclic ring is a morpholine. In certain embodiments, the heterocyclic ring is an azepane.

In certain embodiments, $R_2$ is —$CH_2$-$A_1$.

In certain embodiments, $A_1$ is an unsubstituted phenyl. In certain embodiments, $R_2$ is unsubstituted benzyl.

In certain embodiments, $A_1$ is a phenyl substituted with one or more $R_4$. In certain embodiments, $R_4$ is haloalkyl. In certain embodiments, $R_4$ is trifluoromethyl. In certain embodiments, $R_4$ is halogen. In certain embodiments, $R_4$ is fluoro. In certain embodiments, $R_4$ is chloro. In certain embodiments, $R_4$ is an alkoxy, such as methoxy. In certain embodiments, $R_2$ is substituted benzyl. In certain embodiments, $R_2$ is trifluoromethylbenzyl. In certain embodiments, $R_2$ is trifluorobenzyl. In certain embodiments, $R_2$ is fluorobenzyl. In certain embodiments, $R_2$ is difluorobenzyl. In certain embodiments, $R_2$ is chlorobenzyl. In certain embodiments, $R_2$ is 4-methoxybenzyl.

In certain embodiments, $A_1$ is naphthalene. In certain embodiments, $A_1$ is benzothiazole.

In certain embodiments, both a and b are a double bond. In certain embodiments, at least one of a and b are a single bond. In certain embodiments, both a and b are a single bond.

In one aspect, the present methods employ a compound of Formula (VII):

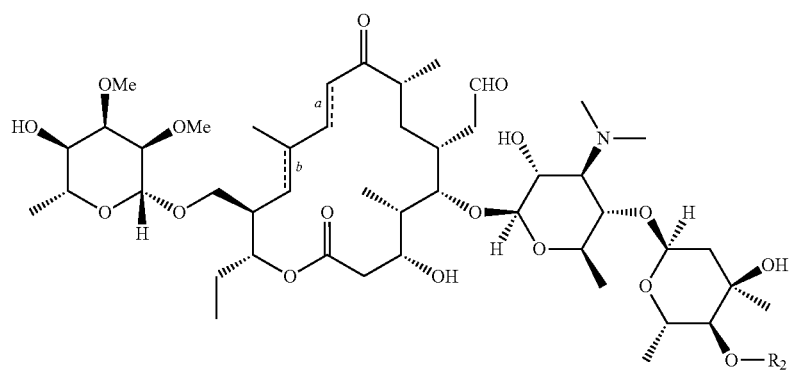

(VII)

and salts thereof, wherein:

$R_2$ represents —C(O)C($R_4$)($R_5$)($R_6$), wherein each of $R_4$, $R_5$, and $R_6$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —$CH_2$-$A_1$, wherein $A_1$ represents a 6- to 10-membered aryl or a 5- to 10-membered heteroaryl and $A_1$ is unsubstituted or substituted with one or more $R_4$, wherein each $R_4$ is independently selected from the group consisting of halogen, $C_1$-$C_6$-alkyl, $C_1$-$C_6$-haloalkyl, and —O—$R_9$, where $R_9$ represents $C_1$-$C_6$-alkyl; and each of a and b independently represents either a single bond or a double bond.

In certain embodiments, $R_2$ is —C(O)C($R_4$)($R_5$)($R_6$). Each of $R_4$, $R_5$, and $R_6$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_5$ is $C_1$-$C_6$ alkyl. In certain embodiments, $R_6$ is $C_1$-$C_6$ alkyl. In certain embodiments, each of $R_4$, $R_5$, and $R_6$ are $C_1$-$C_6$ alkyl.

In certain embodiments, $R_2$ is —C(O)N($R_7$)($R_8$). In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

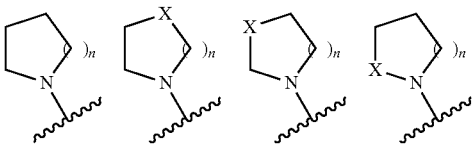

where X is O, S, or N($R_B$). $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_2$ is —$CH_2$-$A_1$ and $A_1$ is a 6- to 10-membered aryl or a 5- to 10-membered heteroaryl. In certain embodiments, $A_1$ is phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

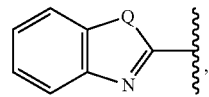

where Q is O, S, or N($R_C$). $R_C$ is selected from hydrogen, $C_1$-$C_6$-alkyl, or $C_1$-$C_6$-haloalkyl.

In certain embodiments, $A_1$ is unsubstituted.

In certain embodiments, $A_1$ is substituted with one or more $R_4$. In certain embodiments, $R_4$ is halogen, $C_1$-$C_6$-alkyl, $C_1$-$C_6$-haloalkyl, or —O—$R_9$. In certain embodiments, $R_4$ is —O—$R_9$ and $R_9$ is $C_1$-$C_6$-alkyl. In certain embodiments, $R_4$ is —O—$R_9$ and $R_9$ is methyl. In certain embodiments, $R_4$ is halogen, $C_1$-$C_6$-alkyl, or $C_1$-$C_6$-haloalkyl.

In certain embodiments, $A_1$ is a phenyl substituted with one or more $R_4$. In certain embodiments, $A_1$ is a halophenyl or a dihalophenyl.

In certain embodiments, $R_2$ is —$CH_2$-$A_1$ and $A_1$ is a phenyl substituted with one or more $R_4$. In certain embodiments, $R_4$ is halogen. In certain embodiments, $R_4$ is fluoro. In certain embodiments, $R_2$ is substituted benzyl. In certain embodiments, $R_2$ is fluorobenzyl. In certain embodiments, $R_2$ is difluorobenzyl.

In certain embodiments, $R_2$ is —$CH_2$-$A_1$ and $A_1$ is a 7- to 10-membered aryl optionally substituted with one or more $R_4$. Each $R_4$ is independently selected from the group consisting of halogen, $C_1$-$C_6$-alkyl, and $C_1$-$C_6$-haloalkyl.

In certain embodiments, $R_2$ is —$CH_2$-$A_1$ and $A_1$ is a 5- to 10-membered heteroaryl optionally substituted with one or more $R_4$. Each $R_4$ is independently selected from the group consisting of halogen, $C_1$-$C_6$-alkyl, and $C_1$-$C_6$-haloalkyl.

In certain embodiments, $R_2$ is —C(O)C($R_4$)($R_5$)($R_6$) and each of $R_4$, $R_5$, and $R_6$ are $C_1$-$C_6$ alkyl. In certain embodiments, $R_4$ is methyl. In certain embodiments, $R_5$ is methyl. In certain embodiments, $R_6$ is methyl. In certain embodiments, each of $R_4$, $R_5$, and $R_6$ are methyl.

In certain embodiments, $R_2$ is —C(O)N($R_7$)($R_8$) and one or both of $R_7$ or $R_8$ are $C_1$-$C_6$ alkyl. In certain embodiments, one or both of $R_7$ or $R_8$ are methyl. In certain embodiments, one or both of $R_7$ or $R_8$ are ethyl. In certain embodiments, one or both of $R_7$ or $R_8$ are propyl, such as n-propyl or isopropyl. In certain embodiments, one or both of $R_7$ or $R_8$ are butyl, such as n-butyl, isobutyl, or sec-butyl.

In certain embodiments, $R_2$ is —C(O)N($R_7$)($R_8$) and each of $R_7$ and $R_8$ are $C_1$-$C_6$ alkyl. In certain embodiments, both of $R_7$ and $R_8$ are ethyl. In certain embodiments, both of $R_7$ and $R_8$ are propyl, such as n-propyl or isopropyl. In certain embodiments, both of $R_7$ and $R_8$ are butyl, such as n-butyl, isobutyl, or sec-butyl.

In certain embodiments, $R_2$ is —C(O)N($R_7$)($R_8$) and one or both of $R_7$ or $R_8$ are $C_3$-$C_8$-cycloalkyl. In certain embodiments, both of $R_7$ and $R_8$ are $C_3$-$C_8$-cycloalkyl. In certain embodiments, both of $R_7$ and $R_8$ are cyclohexyl.

In certain embodiments, $R_2$ is dialkyl carbamoyl. In certain embodiments, $R_2$ is diethyl carbamoyl. In certain embodiments, $R_2$ is dipropyl carbamoyl. In certain embodiments, $R_2$ is di(propan-2-yl)carbamoyl. In certain embodiments, $R_2$ is dibutyl carbamoyl.

In certain embodiments, $R_2$ is dicycloalkyl carbamoyl. In certain embodiments, $R_2$ is dicyclohexylcarbamoyl.

In certain embodiments, $R_2$ is —C(O)N($R_7$)($R_8$) and $R_7$ and $R_8$ together with the nitrogen atom to which they are attached form an optionally substituted saturated or partially saturated heterocyclic ring. In certain embodiments, the heterocyclic ring is a non-aromatic ring. In certain embodiments, the heterocyclic ring is a morpholine.

In certain embodiments, both a and b are a double bond. In certain embodiments, at least one of a and b are a single bond. In certain embodiments, both a and b are a single bond.

In one aspect, the present methods employ a compound of Formula (VIII):

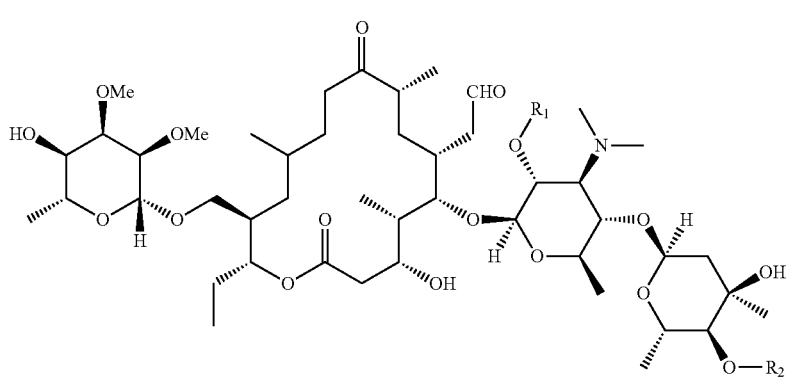

(VIII)

and salts thereof, wherein:

$R_1$ represents hydrogen or —C(O)$R_3$, wherein $R_3$ represents $C_1$-$C_6$-alkyl; and $R_2$ represents —C(O)C($R_4$)($R_5$)($R_6$), wherein each of $R_4$, $R_5$, and $R_6$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —$CH_2$-$A_1$, wherein $A_1$ represents a 6- to 10-membered aryl or a 5- to 10-membered heteroaryl and $A_1$ is unsubstituted or substituted with one or more $R_4$, wherein each $R_4$ is independently selected from the group consisting of halogen, $C_1$-$C_6$-alkyl, $C_1$-$C_6$-haloalkyl, and —O—$R_9$, where $R_9$ represents $C_1$-$C_6$-alkyl.

In certain embodiments, $R_1$ is hydrogen.

In certain embodiments, $R_1$ is —C(O)$R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl.

In certain embodiments, $R_2$ is —C(O)C($R_4$)($R_5$)($R_6$). Each of $R_4$, $R_5$, and $R_6$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_5$ is $C_1$-$C_6$ alkyl. In certain embodiments, $R_6$ is $C_1$-$C_6$ alkyl. In certain embodiments, each of $R_4$, $R_5$, and $R_6$ are $C_1$-$C_6$ alkyl.

In certain embodiments, $R_4$, $R_5$, and $R_6$ are the same. For example, in certain embodiments, each of $R_4$, $R_5$, and $R_6$ are methyl. In certain embodiments, at least two of $R_4$, $R_5$, and $R_6$ are the same. In certain embodiments, $R_4$, $R_5$, and $R_6$ are different.

In certain embodiments, $R_2$ is —C(O)N($R_7$)($R_8$). In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

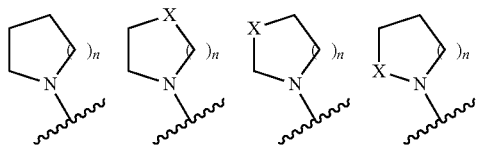

where X is O, S, or N($R_B$). $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_2$ is —CH$_2$-$A_1$ and $A_1$ is a 6- to 10-membered aryl or a 5- to 10-membered heteroaryl. In certain embodiments, $A_1$ is phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

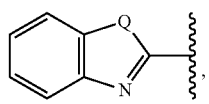

where Q is O, S, or N($R_C$). $R_C$ is selected from hydrogen, $C_1$-$C_6$-alkyl, or $C_1$-$C_6$-haloalkyl.

In certain embodiments, $A_1$ is unsubstituted. In certain embodiments, $A_1$ is substituted with one or more $R_A$. In certain embodiments, $R_A$ is halogen, $C_1$-$C_6$-alkyl, or $C_1$-$C_6$-haloalkyl.

In certain embodiments, $R_1$ is —C(O)$R_3$ and $R_3$ is $C_1$-$C_6$-alkyl. In certain embodiments, $R_3$ is methyl. In certain embodiments, $R_3$ is propyl. In certain embodiments, $R_3$ is n-propyl. In certain embodiments, $R_3$ is isopropyl. In certain embodiments, $R_3$ is butyl. In certain embodiments, $R_3$ is n-butyl. In certain embodiments, $R_3$ is isobutyl. In certain embodiments, $R_3$ is tert-butyl.

In certain embodiments, $R_2$ is —C(O)N($R_7$)($R_8$) and one or both of $R_7$ or $R_8$ are $C_1$-$C_6$ alkyl. In certain embodiments, one or both of $R_7$ or $R_8$ are methyl. In certain embodiments, one or both of $R_7$ or $R_8$ are ethyl. In certain embodiments, one or both of $R_7$ or $R_8$ are propyl, such as n-propyl or isopropyl. In certain embodiments, one or both of $R_7$ or $R_8$ are butyl, such as n-butyl, isobutyl, or sec-butyl.

In certain embodiments, $R_2$ is —C(O)N($R_7$)($R_8$) and each of $R_7$ and $R_8$ are $C_1$-$C_6$ alkyl. In certain embodiments, both of $R_7$ and $R_8$ are methyl. In certain embodiments, both of $R_7$ and $R_8$ are ethyl. In certain embodiments, both of $R_7$ and $R_8$ are propyl, such as n-propyl or isopropyl. In certain embodiments, both of $R_7$ and $R_8$ are butyl, such as n-butyl, isobutyl, or sec-butyl. In certain embodiments, one of $R_7$ or $R_8$ is butyl and the other of $R_7$ or $R_8$ is ethyl.

In certain embodiments, $R_2$ is dialkyl carbamoyl. In certain embodiments, $R_2$ is dimethyl carbamoyl. In certain embodiments, $R_2$ is diethyl carbamoyl. In certain embodiments, $R_2$ is dipropyl carbamoyl. In certain embodiments, $R_2$ is di(propan-2-yl)carbamoyl. In certain embodiments, $R_2$ is dibutyl carbamoyl. In certain embodiments, $R_2$ is bis(2-methylpropyl)carbamoyl. In certain embodiments, $R_2$ is N-butyl-N-ethylcarbamoyl.

In certain embodiments, $R_2$ is —CH$_2$-$A_1$.

In certain embodiments, $A_1$ is a phenyl substituted with one or more $R_A$. In certain embodiments, $R_A$ is haloalkyl. In certain embodiments, $R_A$ is halogen. In certain embodiments, $R_A$ is fluoro.

In certain embodiments, $R_2$ is substituted benzyl. In certain embodiments, $R_2$ is trifluoromethylbenzyl. In certain embodiments, $R_2$ is fluorobenzyl. In certain embodiments, $R_2$ is difluorobenzyl.

In certain embodiments, $R_1$ is hydrogen and $R_2$ is —C(O)N(CH$_2$CH$_3$)$_2$.

In certain embodiments, $R_1$ is —C(O)CH(CH$_3$)$_2$ and $R_2$ is —C(O)N(CH$_2$CH$_3$)$_2$.

In certain embodiments, $R_1$ is hydrogen and $R_2$ is fluorobenzyl.

In certain embodiments, $R_1$ is hydrogen and $R_2$ is

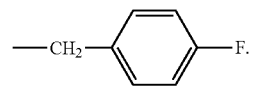

In certain embodiments, $R_1$ is hydrogen and $R_2$ is difluorobenzyl.

In certain embodiments, $R_1$ is hydrogen and $R_2$ is

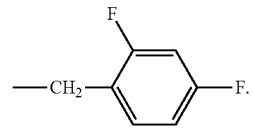

In one aspect, the present invention includes compounds of Formula (IX):

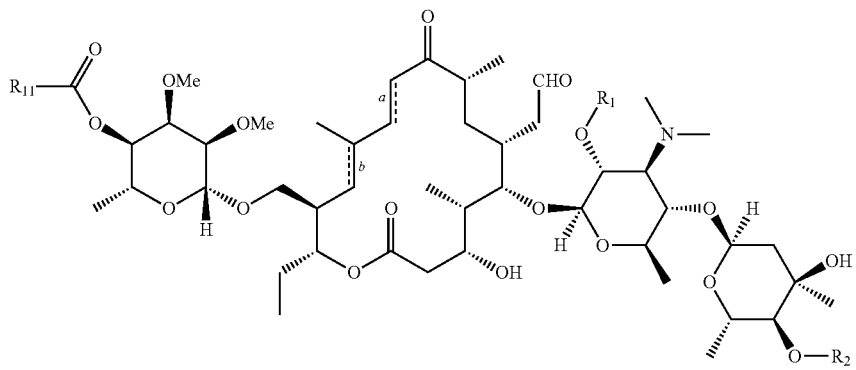

(IX)

and salts thereof, wherein:

$R_1$ represents hydrogen or —C(O)$R_3$, wherein $R_3$ represents an optionally substituted $C_1$-$C_6$-alkyl or $C_1$-$C_6$-haloalkyl;

$R_2$ represents —C(O)C($R_4$)($R_5$)($R_6$), wherein each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —CH$_2$-$A_1$, wherein $A_1$ represents a 6- to 10-membered aryl or a 5- to 10-membered heteroaryl and $A_1$ is unsubstituted or substituted with one or more $R_A$, wherein each $R_A$ is independently selected from the group consisting of halogen, $C_1$-$C_6$-alkyl, $C_1$-$C_6$-alkoxy, and $C_1$-$C_6$-haloalkyl;

$R_{11}$ represents an optionally substituted $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, or $C_3$-$C_8$-cycloalkyl-$C_1$-$C_4$-alkyl; and each of a and b independently represents either a single bond or a double bond.

In certain embodiments, $R_1$ is hydrogen.

In certain embodiments, $R_1$ is —C(O)$R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl. In certain embodiments, $R_3$ is methyl. In certain embodiments, $R_3$ is ethyl. In certain embodiments, $R_3$ is propyl. In certain embodiments, $R_3$ is n-propyl. In certain embodiments, $R_3$ is isopropyl. In certain embodiments, $R_3$ is butyl. In certain embodiments, $R_3$ is n-butyl. In certain embodiments, $R_3$ is isobutyl. In certain embodiments, $R_3$ is tert-butyl. In certain embodiments, $R_3$ is $C_1$-$C_6$-haloalkyl.

In certain embodiments, $R_2$ is —C(O)C($R_4$)($R_5$)($R_6$). Each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_5$ is $C_1$-$C_6$ alkyl. In certain embodiments, $R_6$ is $C_1$-$C_6$ alkyl. In certain embodiments, each of $R_4$, $R_5$, and $R_6$ are $C_1$-$C_6$ alkyl.

In certain embodiments, $R_4$, $R_5$, and $R_6$ are the same. For example, in certain embodiments, each of $R_4$, $R_5$, and $R_6$ are methyl. In certain embodiments, at least two of $R_4$, $R_5$, and $R_6$ are the same. In certain embodiments, $R_4$, $R_5$, and $R_6$ are different.

In certain embodiments, $R_2$ is —C(O)N($R_7$)($R_8$). In certain embodiments, each of $R_7$ and $R_8$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

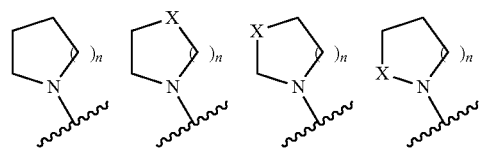

where X is O, S, or N($R_B$). $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_2$ is —C(O)N($R_7$)($R_8$) and one or both of $R_7$ or $R_8$ are $C_1$-$C_6$ alkyl. In certain embodiments, one or both of $R_7$ or $R_8$ are methyl. In certain embodiments, one or both of $R_7$ or $R_8$ are ethyl. In certain embodiments, one or both of $R_7$ or $R_8$ are propyl, such as n-propyl or isopropyl. In certain embodiments, one or both of $R_7$ or $R_8$ are butyl, such as n-butyl, isobutyl, or sec-butyl.

In certain embodiments, $R_2$ is —C(O)N($R_7$)($R_8$) and each of $R_7$ and $R_8$ are $C_1$-$C_6$ alkyl. In certain embodiments, both of $R_7$ and $R_8$ are methyl. In certain embodiments, both of $R_7$ and $R_8$ are ethyl. In certain embodiments, both of $R_7$ and $R_8$ are propyl, such as n-propyl or isopropyl. In certain embodiments, both of $R_7$ and $R_8$ are butyl, such as n-butyl, isobutyl, or sec-butyl. In certain embodiments, one of $R_7$ or $R_8$ is butyl and the other of $R_7$ or $R_8$ is ethyl.

In certain embodiments, $R_2$ is dialkyl carbamoyl. In certain embodiments, $R_2$ is dimethyl carbamoyl. In certain embodiments, $R_2$ is diethyl carbamoyl. In certain embodiments, $R_2$ is dipropyl carbamoyl. In certain embodiments, $R_2$ is di(propan-2-yl)carbamoyl. In certain embodiments, $R_2$ is dibutyl carbamoyl. In certain embodiments, $R_2$ is bis(2-methylpropyl)carbamoyl. In certain embodiments, $R_2$ is N-butyl-N-ethylcarbamoyl.

In certain embodiments, when both a and b are a double bond, $R_1$ is C(O)CH$_3$, $R_{11}$ is CH$_3$, and neither $R_7$ nor $R_8$ are hydrogen.

In certain embodiments, $R_2$ is —CH$_2$-A$_1$ and A$_1$ is a 6- to 10-membered aryl or a 5- to 10-membered heteroaryl. In certain embodiments, A$_1$ is phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, A$_1$ is

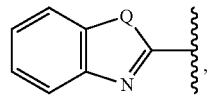

where Q is O, S, or N(R$_C$). R$_C$ is selected from hydrogen; C$_1$-C$_6$-alkyl, or C$_1$-C$_6$-haloalkyl.

In certain embodiments, A$_1$ is unsubstituted. In certain embodiments, A$_1$ is substituted with one or more R$_4$. In certain embodiments, R$_4$ is halogen, C$_1$-C$_6$-alkyl, C$_1$-C$_6$-alkoxy, or C$_1$-C$_6$-haloalkyl.

In certain embodiments, A$_1$ is a phenyl substituted with one or more R$_4$. In certain embodiments, R$_4$ is haloalkyl. In certain embodiments, R$_4$ is halogen. In certain embodiments, R$_4$ is fluoro.

In certain embodiments, R$_2$ is substituted benzyl. In certain embodiments, R$_2$ is trifluoromethylbenzyl. In certain embodiments, R$_2$ is fluorobenzyl. In certain embodiments, R$_2$ is difluorobenzyl.

In certain embodiments, $R_{11}$ is C$_1$-C$_6$-alkyl, such as methyl; ethyl; propyl, such as n-propyl or isopropyl; or butyl, such as n-butyl, isobutyl, or tert-butyl. In certain embodiments, $R_{11}$ is methyl. In certain embodiments, $R_{11}$ is ethyl. In certain embodiments, $R_{11}$ is propyl. In certain embodiments, $R_{11}$ is n-propyl. In certain embodiments, $R_{11}$ is isopropyl. In certain embodiments, $R_{11}$ is butyl. In certain embodiments, $R_{11}$ is n-butyl. In certain embodiments, $R_{11}$ is tert-butyl. In certain embodiments, $R_{11}$ is C$_1$-C$_6$-haloalkyl.

In certain embodiments, $R_1$ is —C(O)CH$_3$; $R_2$ is —C(O)N(CH$_2$CH$_3$)$_2$; and $R_{11}$ is —CH$_2$CH$_3$.

In certain embodiments, $R_1$ is hydrogen; $R_2$ is —C(O)N(CH$_2$CH$_3$)$_2$; and $R_{11}$ is —CH$_2$CH$_3$.

In certain embodiments, $R_1$ is —C(O)CH$_2$CH$_3$; $R_2$ is —C(O)N(CH$_2$CH$_3$)$_2$; and $R_{11}$ is —CH$_2$CH$_3$.

In certain embodiments, $R_1$ is —C(O)CH$_3$; $R_2$ is

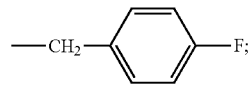

and $R_{11}$ is —CH$_2$CH$_3$.

In certain embodiments, $R_1$ is hydrogen; $R_2$ is

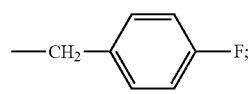

and $R_{11}$ is —CH$_2$CH$_3$.

In certain embodiments, $R_1$ is —C(O)CH$_3$; $R_2$ is —C(O)N(CH$_2$CH$_3$)$_2$; and $R_{11}$ is —CH$_3$.

In certain embodiments, $R_1$ is hydrogen; $R_2$ is —C(O)N(CH$_2$CH$_3$)$_2$; and $R_{11}$ is —CH$_3$.

In certain embodiments, $R_1$ is hydrogen; $R_2$ is —C(O)N(CH$_2$CH$_3$)$_2$; and $R_{11}$ is —CH(CH$_3$)$_2$.

In certain embodiments, $R_1$ is —C(O)CH$_3$; $R_2$ is

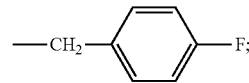

and $R_{11}$ is —CH$_3$.

In certain embodiments, $R_1$ is hydrogen; $R_2$ is

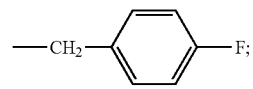

and $R_{11}$ is —CH$_3$.

In certain embodiments, $R_1$—C(O)CH$_3$; $R_2$ is

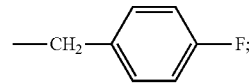

and $R_{11}$ is —CH(CH$_3$)$_2$.

In certain embodiments, $R_1$ is hydrogen; $R_2$ is

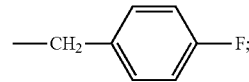

and $R_{11}$ is —CH(CH$_3$)$_2$. Anti-*Wolbachia* activity of a compound can be determined using various methods known to those of skill in the art, including in vitro and in vivo assays. For example, in certain embodiments, a whole organism *Wolbachia* cell-based assay is used to screen compounds. Such an assay is described in Turner et al., (2006) J. Immunol. 7:1240-1249 and Johnston et al., (2010) Parasit Vectors. 3:99. In certain embodiments, in vitro nematode screening is employed, using, for example, adult male *Onchocerca gutturosa* or *B. malayi*. Townson S, et al., (2006) Filaria J. 5:4. For in vivo nematode screening, established animal models of filarial infection may be utilized and include *Litomosoides sigmodontis* in mice (Hoerauf A, et al. (1999) Journal of Clinical Investigation 103(1): 11-18) and *B. malayi* in gerbils (Ash and Riley, (1970) J Parasitol. 56(5):969-73). For in vivo models, the reduction of *Wolbachia* load following treatment can be measured by qPCR. (McGarry H, et al Mol Biochem Parasitol. (2004) 135(1):57-67, Halliday, A et al. (2014) Parasit Vectors 7, 472).

It is to be understood that compounds disclosed herein may exhibit the stereoisomerism, including geometric isomerism, and/or tautomerism.

For example, the present compounds may exist as stereoisomers where asymmetric or chiral centers are present. These stereoisomers are "R" or "S" depending on the configuration of substituents around the chiral carbon atom.

The terms "R" and "S" used herein are configurations as defined in IUPAC 1974 Recommendations for Section E, Fundamental Stereochemistry, Pure Appl. Chem., 1976, 45: 13-30.

The present disclosure contemplates various stereoisomers and mixtures thereof and these are specifically included within the scope of the invention. Stereoisomers include enantiomers and diastereomers, and mixtures of enantiomers or diastereomers. Individual stereoisomers of the present compounds may be prepared synthetically from commercially available starting materials which contain asymmetric or chiral centers or by preparation of racemic mixtures followed by resolution.

The present disclosure also contemplates various geometric isomers and mixtures thereof resulting from the disposition of substituents around a carbon-carbon double bond, a carbon-nitrogen double bond, a cycloalkyl group, or a heterocycle group.

The present disclosure also contemplates various tautomers and mixtures thereof resulting from, for example, interconversion between keto and enol forms.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

The present disclosure also contemplates isotopically-labeled compounds, which are identical to those recited in Formula (I), Formula (I-1), Formula (II), Formula (III), Formula (IV), Formula (V), Formula (VI), Formula (VII), Formula (VIII), or Formula (IX) but for the fact that one or more atoms are replaced by an atom having an atomic mass or mass number different from the atomic mass or mass number usually found in nature. Examples of isotopes suitable for inclusion in such isotopically-labeled compounds are hydrogen, carbon, nitrogen, oxygen, phosphorus, fluorine, and chlorine, such as, but not limited to $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of Formula (I), Formula (I-1), Formula (II), Formula (III), Formula (IV), Formula (V), Formula (VI), Formula (VII), Formula (VIII), or Formula (IX) are $^{11}$C, $^{13}$N, $^{15}$O, and $^{18}$F. Isotopically-labeled compounds of Formula (I), Formula (I-1), Formula (II), Formula (III), Formula (IV), Formula (V), Formula (VI), Formula (VII), Formula (VIII), or Formula (IX) can generally be prepared by conventional techniques known to those skilled in the art or by processes analogous to those described in the accompanying Schemes and Examples using appropriate isotopically-labeled reagent in place of non-isotopically-labeled reagent.

D. Methods for Preparing Compounds

The compounds described herein can be better understood in connection with the following synthetic schemes and methods which illustrate a means by which the compounds can be prepared.

Certain compounds that may be used in carrying out the present methods may be prepared from Tylosin A as described below.

As indicated in Scheme 1, Tylosin A (or a salt thereof) is selectively acylated at the 2'-hydroxyl using an acylating agent such as an acid anhydride or the like, in a solvent such as acetone or chloroform or ethanol or the like. Alternatively, the acylating agent may be generated in situ, using a carboxylic acid and an activating agent such as isobutyl chloformate or the like, optionally in the presence of a base such as N-methylmorpholine or the like.

SCHEME 1

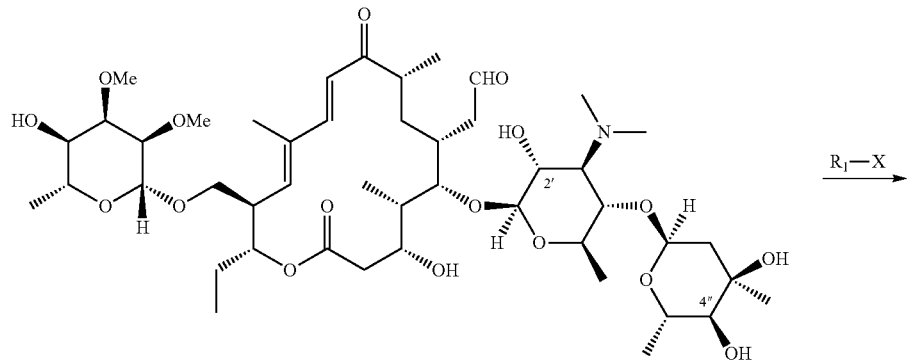

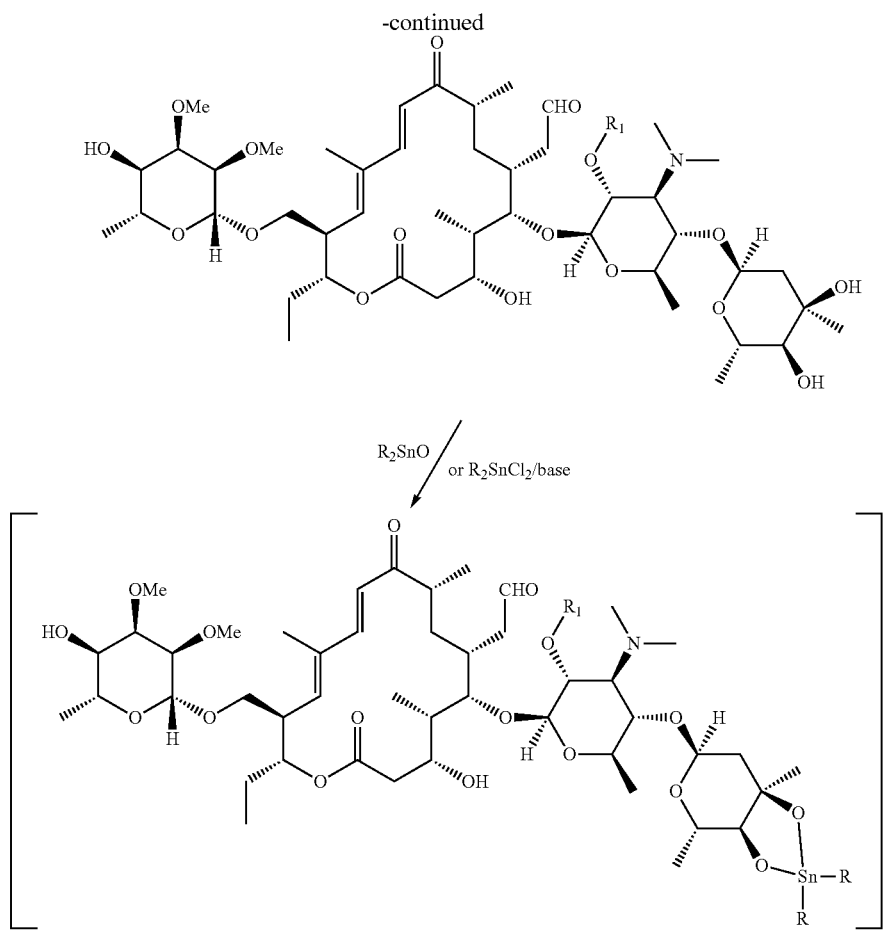

The resultant 2'-ester may be converted to the corresponding 3"/4"-cyclic tin reagent through reaction with dibutyltin oxide, or dibutyltin dichloride, or the like, optionally in the presence of a base such as 1,2,2,6,6,-pentamethylpiperidine or the like, in a solvent such as toluene or THF or the like. As indicated in Scheme 2, the resultant tin reagent is not generally isolated, but is reacted directly a) with an acylating agent, such as an acid chloride or the like, to give the corresponding 4"-acylated analog;

b) with a carbamylating agent, such diethylcarbamyl chloride or the like, to give the corresponding 4"-carbamate analog; or c) with a benzylating agent, for example 4-fluorobenzyl brominde or the like, optionally in the presence of an iodide source such as tetra-n-butylammonium iodide or the like, to give the corresponding 4"-benzylated analog.

SCHEME 2
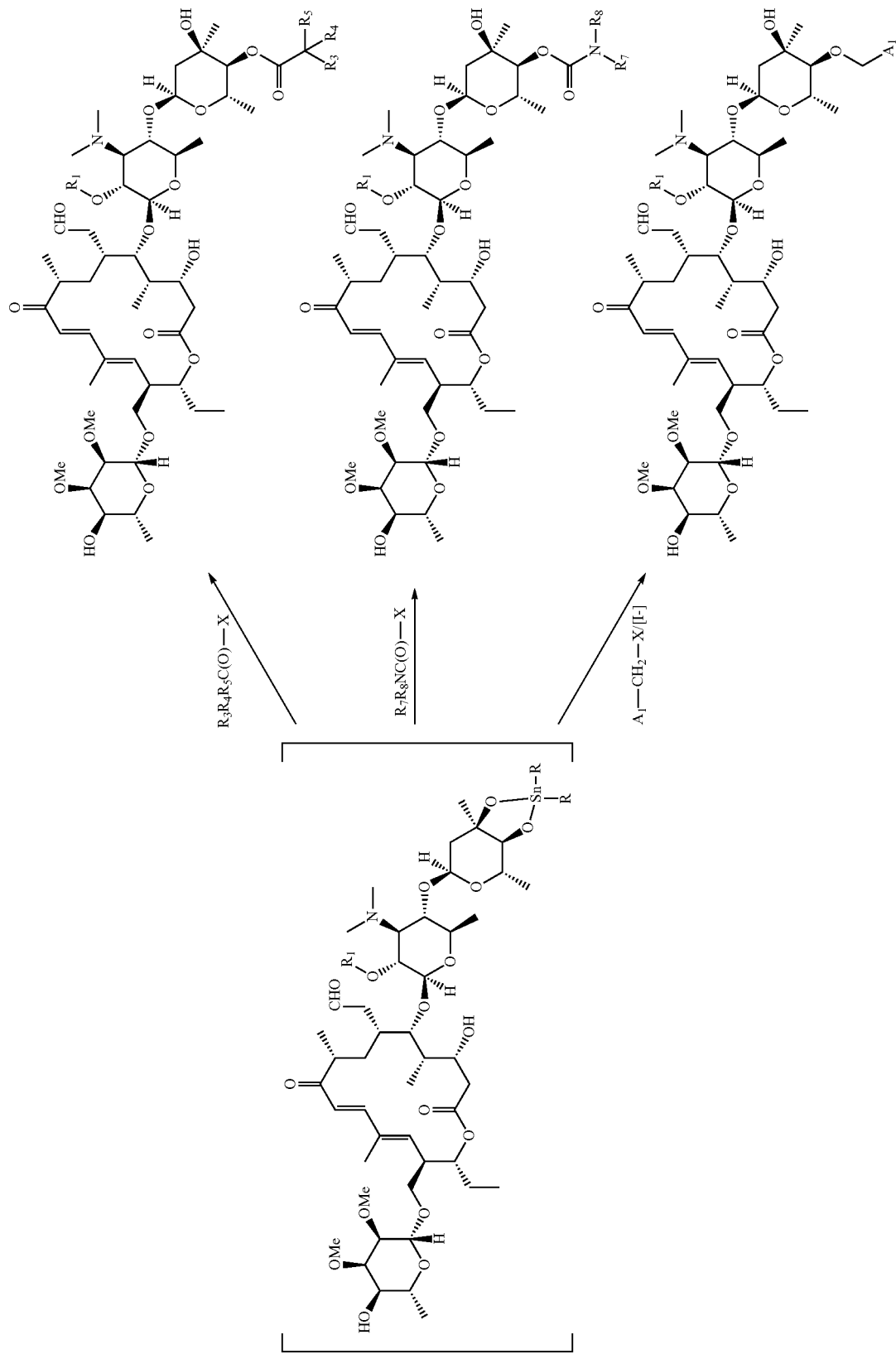

In the specific case where the 2'-substituent is acetyl, the resultant 2'-OAc/4"-substituted analog may (as in Scheme 3) be warmed in an alcohol like methanol or the like, optionally in the presence of a catalyst like solid sodium bicarbonate or the like, to hydrolyze the 2'-ester, resulting in the production of a 2'-unsubstituted, 4"-substituted analog.

SCHEME 3

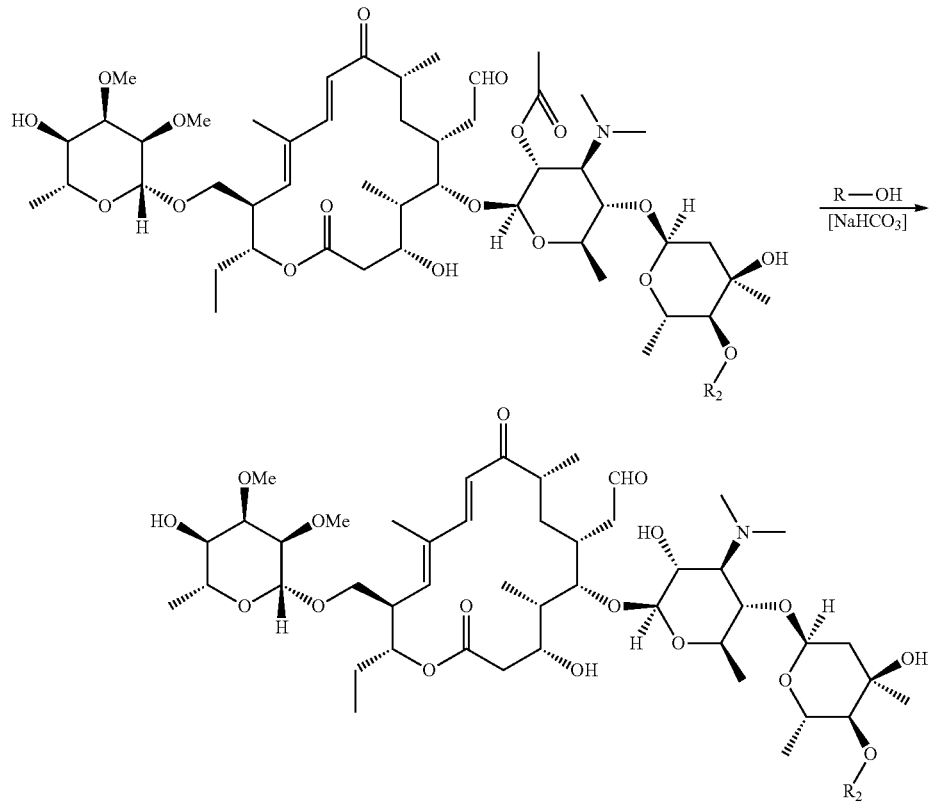

To prepare compounds that are simultaneously modified at the 2', 4", and 4'" positions, a 2'/4"-derivatized intermediate (prepared as described in Scheme 2) is treated with an acylating agent like acetic anhydride, or propionic anhydride, or the like, in a basic solvent like pyridine or lutidine or the like, as shown in Scheme 4. In the specific case where the 2'-substituent is acetyl, the resultant 2'-OAc/4"/4'"-substituted analog may be warmed in an alcohol like methanol or the like, optionally in the presence of a catalyst like solid sodium bicarbonate or the like, to hydrolyze the 2'-ester, resulting in the production of a 2'-unsubstituted, 4"/4'"-disubstituted analog.

SCHEME 4

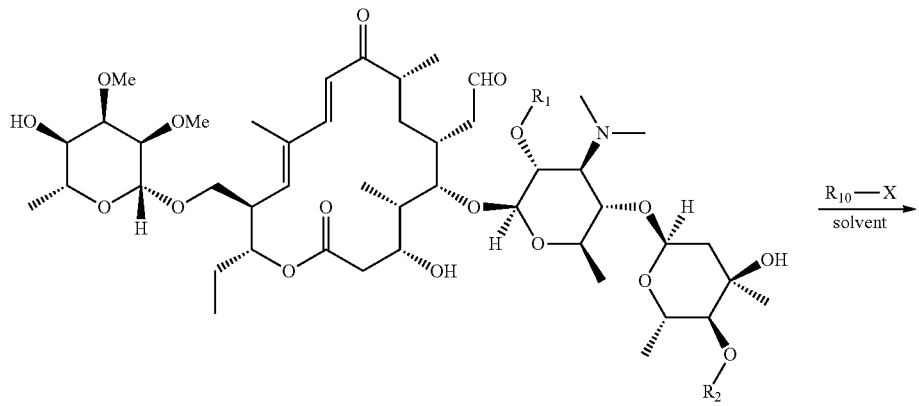

-continued

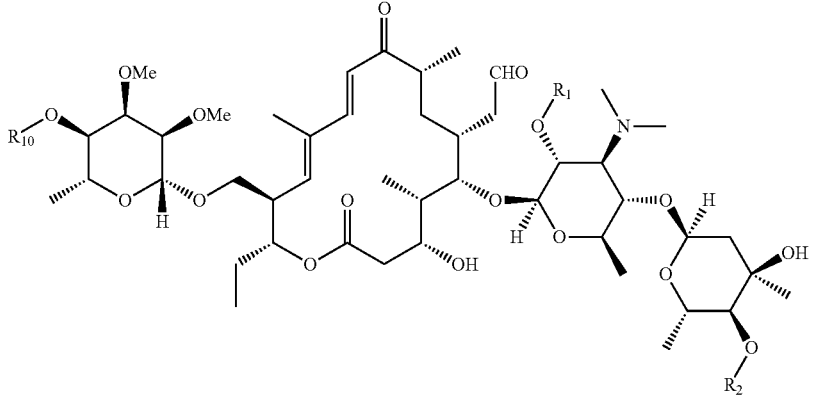

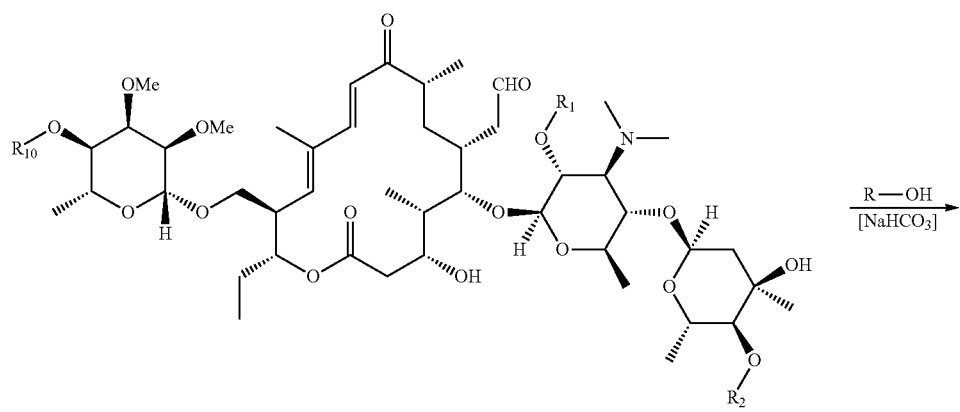

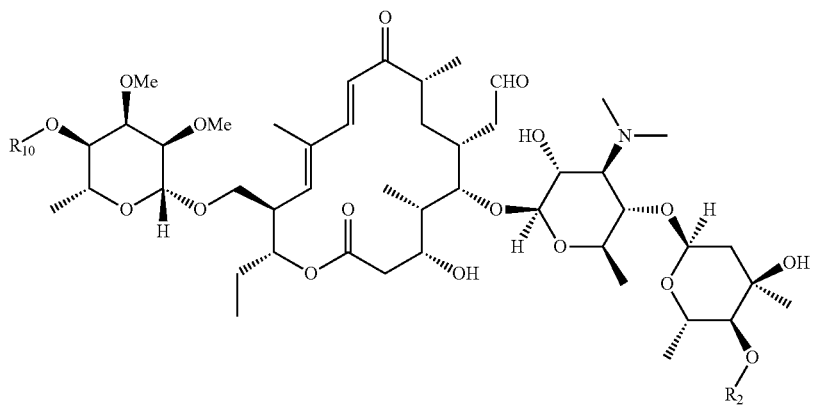

To prepare compounds that are reduced at the 10/11 and/or 12/13 positions, the corresponding unsaturated compound may be treated with hydrogen gas, or a hydrogen source like ammonium formate or the like, in the presence of a hydrogenation catalyst like palladium-on-carbon or platinum-on-carbon or Raney nickel or the like, in a solvent like ethanol or ethyl acetate or the like. By controlling the time, temperature, solvent and concentration of the reaction, one or both of the 10/11 and 12/13 double bonds may be reduced to single bonds.

SCHEME 5

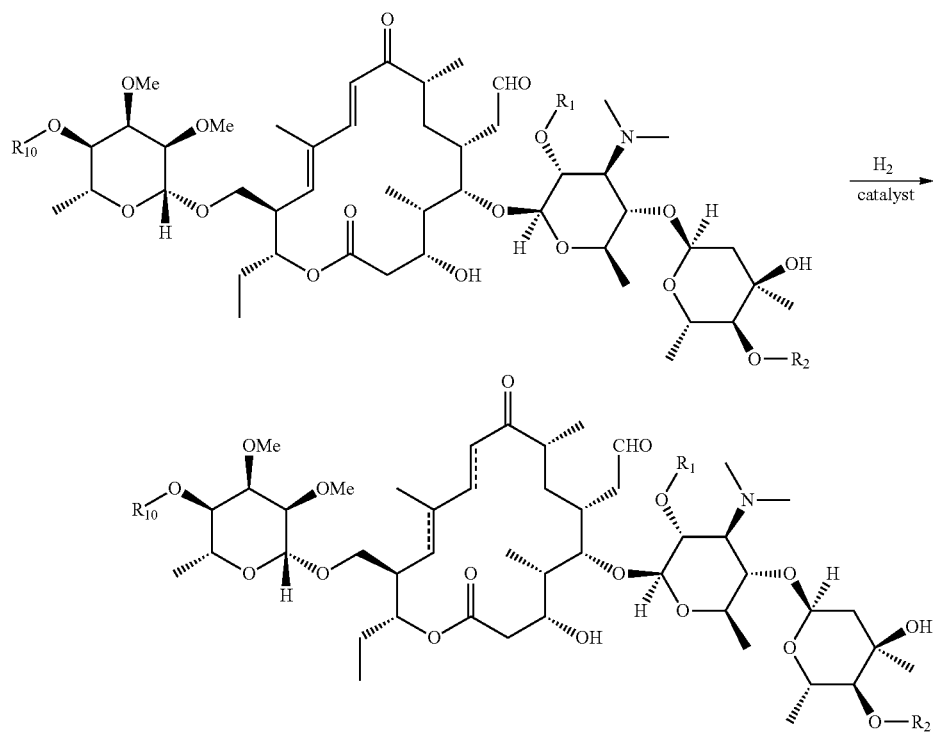

The compounds and intermediates that can be used in the methods described herein may be isolated and purified by conventional methods in the field of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Certain compounds that can be used in the methods described herein have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like. In certain embodiments, a compound may be reacted with a weak acid to provide the desired salt. Examples of suitable weak acids, but are not limited to, tartaric acid, lactic acid, acetic acid, propionic acid, citric acid, malic acid, and the like. In certain embodiments, the acid is tartaric acid.

Optimum reaction conditions and reaction times for each individual step can vary depending on the particular reactants employed and substituents present in the reactants used. Unless otherwise specified, solvents, temperatures and other reaction conditions can be readily selected. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that is not compatible with the reaction conditions, and deprotection at a suitable point in the reaction sequence of the method are included in the scope of the invention. Suitable protecting groups and the methods for protecting and deprotecting different substituents using such suitable protecting groups are well known; examples of which can be found in P G M Wuts and T W Greene, Greene's Protective Groups in Organic Synthesis (4th ed.), John Wiley & Sons, NY (2006), which is incorporated herein by reference in its entirety. Synthesis of the compounds mentioned herein can be accomplished by methods analogous to those described in the synthetic schemes described hereinabove.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

E. Compositions for Prevention or Treatment of Filariasis

In at least one aspect, the present invention includes a composition for preventing or treating filariasis. The composition for preventing or treating filariasis includes a compound described herein or a salt thereof. In certain embodiments, the composition for preventing or treating filariasis comprises a compound of Formula (I) or a salt thereof. In certain embodiments, the composition for preventing or treating filariasis comprises a compound of Formula (I-1) or a salt thereof. In certain embodiments, the composition for preventing or treating filariasis comprises a compound of Formula (II) or a salt thereof. In certain embodiments, the composition for preventing or treating filariasis comprises a compound of Formula (III) or a salt thereof. In certain embodiments, the composition for preventing or treating filariasis comprises a compound of Formula (IV) or a salt thereof. In certain embodiments, the composition for preventing or treating filariasis comprises a compound of Formula (V) or a salt thereof. In certain embodiments, the composition for preventing or treating filariasis comprises a compound of Formula (VI) or a salt thereof. In certain embodiments, the composition for preventing or treating filariasis comprises a compound of Formula (VII) or a salt thereof. In certain embodiments, the composition for preventing or treating filariasis comprises a compound of Formula (VIII) or a salt thereof. In certain embodiments, the composition for preventing or treating filariasis comprises a compound of Formula (IX) or a salt thereof.

In certain embodiments, the composition for preventing or treating filariasis comprises one or more conventional pharmaceutically acceptable carriers. Pharmaceutically acceptable carriers include, without limitation, a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition for preventing or treating filariasis, according to the judgment of one skilled in the art of formulations. Formulation of drugs is generally discussed in, for example, Hoover, J., Remington's Pharmaceutical Sciences (Mack Publishing Co., 1975) and Ansel's Pharmaceutical Dosage Forms and Drug Delivery Systems (Lippincott Williams & Wilkins, 2005).

In at least one aspect, the present invention includes pharmaceutical compositions for preventing or treating filariasis comprising a therapeutically effective amount of a compound described herein in combination with one or more pharmaceutically acceptable carriers. In certain embodiments, the pharmaceutical compositions for preventing or treating filariasis comprise a compound of formula (I) or a salt thereof formulated together with one or more pharmaceutically acceptable carriers. In certain embodiments, the pharmaceutical compositions for preventing or treating filariasis comprise a compound of formula (I-1) or a salt thereof formulated together with one or more pharmaceutically acceptable carriers. In certain embodiments, the pharmaceutical compositions for preventing or treating filariasis comprise a compound of formula (II) or a salt thereof formulated together with one or more pharmaceutically acceptable carriers. In certain embodiments, the pharmaceutical compositions for preventing or treating filariasis comprise a compound of formula (III) or a salt thereof formulated together with one or more pharmaceutically acceptable carriers. In certain embodiments, the pharmaceutical compositions for preventing or treating filariasis comprise a compound of formula (IV) or a salt thereof formulated together with one or more pharmaceutically acceptable carriers. In certain embodiments, the pharmaceutical compositions for preventing or treating filariasis comprise a compound of formula (V) or a salt thereof formulated together with one or more pharmaceutically acceptable carriers. In certain embodiments, the pharmaceutical compositions for preventing or treating filariasis comprise a compound of formula (VI) or a salt thereof formulated together with one or more pharmaceutically acceptable carriers. In certain embodiments, the pharmaceutical compositions for preventing or treating filariasis comprise a compound of formula (VII) or a salt thereof formulated together with one or more pharmaceutically acceptable carriers. In certain embodiments, the pharmaceutical compositions for preventing or treating filariasis comprise a compound of formula (VIII) or a salt thereof formulated together with one or more pharmaceutically acceptable carriers. In certain embodiments, the pharmaceutical compositions for preventing or treating filariasis comprise a compound of formula (IX) or a salt thereof formulated together with one or more pharmaceutically acceptable carriers.

Pharmaceutical compositions may be formulated for any route of administration. The pharmaceutical compositions can be administered to humans and other animals orally, nasally, rectally, parenterally, intracisternally, intravaginally, intraperitoneally, topically (as by powders, ointments or drops), or bucally. The term "parenterally", as used herein, refers to modes of administration which include intravenous, intramuscular, intraperitoneal, intrasternal, subcutaneous, intraarticular injection and infusion.

In certain embodiments, the pharmaceutical compositions are formulated for oral administration in solid or liquid form.

In certain embodiments, the pharmaceutical composition is a solid dosage form for oral administration. Solid dosage forms for oral administration include capsules, tablets, pills, powders, and granules. In certain embodiments, the pharmaceutical composition includes, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol. In certain embodiments, the pharmaceutical composition is tableted or encapsulated for convenient administration. In certain embodiments, such capsules or tablets contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

In certain embodiments, the pharmaceutical composition is a liquid dosage form for oral administration. Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs. In certain embodiments, the liquid dosage forms contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. In addition, in certain embodiments, oral compositions, also include wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

In certain embodiments, the pharmaceutical composition is for parenteral administration. In certain embodiments, formulations for parenteral administration are prepared from sterile powders or granules having one or more of the carriers or excipients mentioned for use in the formulations for oral administration. In certain embodiments, a compound or salt thereof is dissolved in water, polyethylene glycol, propylene glycol, ethanol, corn oil, cottonseed oil, peanut oil, sesame oil, benzyl alcohol, sodium chloride, and/or various buffers. In certain embodiments, the pH is adjusted, if necessary, with a suitable acid, base, or buffer.

In certain embodiments, the pharmaceutical composition is for rectal or vaginal administration. Compositions for rectal or vaginal administration are preferably suppositories that can be prepared by, for example, mixing a compound or salt thereof with a suitable nonirritating carrier or excipient that is solid at ordinary room temperatures, but liquid at body temperature. Suitable carriers or excipients include, for example, cocoa butter; synthetic mono-, di-, or triglycerides, fatty acids, and/or polyethylene glycols.

Topical administration includes the use of transdermal administration, such as transdermal patches or iontophoresis devices.

Other carriers and modes of administration known in the pharmaceutical art also may be used.

In at least one aspect, compounds described herein are used in the form of pharmaceutically acceptable salts or esters, or amides derived from inorganic or organic acids. In certain embodiments, pharmaceutically acceptable salts are those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds or separately by, for example, reacting a free base function with a suitable organic acid.

Representative pharmaceutically acceptable salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

In certain embodiments, pharmaceutically acceptable acid addition salts of the compounds of Formula (I), (I-1), (II), (III), (IV), (V), (VI), (VII), (VIII), or (IX) are prepared from an inorganic or organic acid. Examples of acids which can be employed to form pharmaceutically acceptable acid addition salts include inorganic acids such as hydrochloric acid, hydrobromic acid, sulphuric acid and phosphoric acid and organic acids such as acetic acid, oxalic acid, maleic acid, succinic acid, tartaric acid, and citric acid. In certain embodiments, a weak acid, including, but not limited to, tartaric acid, lactic acid, acetic acid, propionic acid, citric acid, malic acid, and the like, can be employed to form pharmaceutically acceptable acid addition salt.

In certain embodiments, pharmaceutically acceptable base addition salts of the compounds of Formula (I), (I-1), (II), (III), (IV), (V), (VI), (VII), (VIII), or (IX) include, for example, metallic salts and organic salts. In certain embodiments, pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

In at least one aspect, the present invention includes a composition comprising one or more macrolide compounds or a salt thereof. In certain embodiments, at least 50% of the macrolide compounds in the composition are a compound of Formula (I), (I-1), (II), (III), (IV), (V), (VI), (VII), (VIII), (IX), or a salt thereof. In certain embodiments, at least 60% of the macrolide compounds in the composition are a compound of Formula (I), (I-1), (II), (III), (IV), (V), (VI), (VII), (VIII), (IX), or a salt thereof. In certain embodiments, at least 80% of the macrolide compounds in the composition are a compound of Formula (I), (I-1), (II), (III), (IV), (V), (VI), (VII), (VIII), (IX), or a salt thereof. In certain embodiments, at least 80% of the macrolide compounds in the composition are a compound of Formula (I), (I-1), (II), (III), (IV), (V), (VI), (VII), (VIII), (IX), or a salt thereof. In certain embodiments, at least 90% of the macrolide compounds in the composition are a compound of Formula (I), (I-1), (II), (III), (IV), (V), (VI), (VII), (VIII), (IX), or a salt thereof. In certain embodiments, at least 95% of the macrolide compounds in the composition are a compound of Formula (I), (I-1), (II), (III), (IV), (V), (VI), (VII), (VIII), (IX), or a salt thereof.

In certain embodiments, a compound, such as a compound of Formula (I), (I-1), (II), (III), (IV), (V), (VI), (VII), (VIII), (IX), or a salt thereof is included as an additive to animal feed or drinking water for animals. In certain embodiments, the compound is formulated into premixes in various potencies from 1 to 10% by weight.

The compositions for use either as feed additives or as directly administered preparations may contain any convenient proportion of the compound, for example from 1% or less to 90% or more, by weight. Liquid formulations typically contain 50 to 90% by weight, whereas solid formulations typically contain 1 to 25% by weight.

In one aspect, the methods described herein include providing a compound of Formula (I), (I-1), (II), (III), (IV), (V), (VI), (VII), (VIII), or (IX) to a subject via a prodrug. Thus, in certain embodiments, a prodrug is administered to a subject to provide a metabolite that inhibits growth of a filarial worm, sterilizes an adult filarial worm, reduces microfilariae load, kills a filarial worm, inhibits growth of bacteria associated with a filarial worm, and/or kills bacteria associated with a filarial worm. In this way, filarial worms and/or bacteria harbored within worms are contacted with the metabolite. Contemplated metabolites include one or more compounds of Formula (I), (I-1), (II), (III), (IV), (V), (VI), (VII), (VIII), or (IX). Exemplary prodrug forms of the compounds described herein include 4'-modified prodrugs, such as compounds having a 4'''-O-acyl moiety (e.g., a 4'''-O-acetyl, 4'''-O-propionyl, or 4'''-O-methylpropionyl moiety.

The compounds, compositions, and methods described herein will be better understood by reference to the following examples, which are included as an illustration of and not a limitation upon the scope of the invention.

F. Exemplary Embodiments

In one aspect, the present invention includes embodiments enumerated in the following subparagraphs:

A1. A method of preventing or treating filariasis in a subject in need thereof, comprising administering to the subject a therapeutically effective amount of a macrolide antibiotic.

A2. The method of embodiment A1, wherein the macrolide antibiotic is tylosin A or a salt thereof.

A3. The method of embodiment A1, wherein the macrolide antibiotic is tylosin tartrate.

A4. The method of embodiment A1, wherein the macrolide antibiotic is a derivative or analog of tylosin A or a salt thereof.

A5. The method of any one of the preceding embodiments, wherein the filariasis is lymphatic filariasis or subcutaneous filariasis.

A6. The method of any one of the preceding embodiments, wherein the filariasis is caused by *Onchocerca volvulus, Wuchereria bancrofti, Brugia malayi, Brugia timori,* or *Dirofilaria immitis*.

A7. The method of any one of the preceding embodiments, wherein the subject is a human.

In one aspect, the present invention includes embodiments enumerated in the following subparagraphs:

B8. A method of preventing or treating filariasis in a subject in need thereof, comprising providing to the subject a therapeutically effective amount of a compound of Formula (I-1):

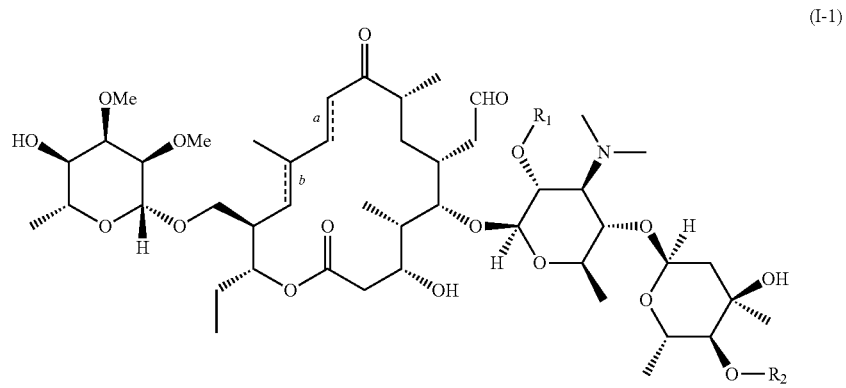

or a salt thereof, wherein:

$R_1$ represents hydrogen or —C(O)$R_3$, wherein $R_3$ represents $C_1$-$C_6$-alkyl; and $R_2$ represents —C(O)C($R_4$)($R_5$)($R_6$), wherein each of $R_4$, $R_5$, and $R_6$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —$CH_2$-$A_1$, wherein $A_1$ represents a 6- to 10-membered aryl or a 5- to 10-membered heteroaryl and $A_1$ is unsubstituted or substituted with one or more $R_A$, wherein each $R_A$ is independently selected from the group consisting of halogen, $C_1$-$C_6$-alkyl, $C_1$-$C_6$-haloalkyl, and —O—$R_9$, where $R_9$ represents $C_1$-$C_6$-alkyl; and each of a and b independently represents either a single bond or a double bond.

B9. The method of embodiment B8, wherein $R_1$ is hydrogen.

B10. The method of embodiment B8, wherein $R_1$ is —C(O)$R_3$.

B11. The method of embodiment B10, wherein $R_3$ is methyl, isopropyl, or n-butyl.

B12. The method of any one of the preceding embodiments, wherein $R_2$ is —C(O)C($R_4$)($R_5$)($R_6$) and $R_4$ is $C_1$-$C_6$-alkyl.

B13. The method of any one of the preceding embodiments, wherein $R_2$ is —C(O)C($R_4$)($R_5$)($R_6$) and each of $R_4$, $R_5$, and $R_6$ are $C_1$-$C_6$-alkyl.

B14. The method of any one of embodiments B8-B11, wherein $R_2$ is —C(O)N($R_7$)($R_8$) and each of $R_7$ and $R_8$ are $C_1$-$C_6$-alkyl, aryl, or $C_3$-$C_8$-cycloalkyl.

B15. The method of any one of embodiments B8-B11, wherein $R_2$ is —C(O)N($R_7$)($R_8$) and $R_7$ and $R_8$ together with the nitrogen atom to which they are attached form an optionally substituted saturated or partially saturated heterocyclic ring.

B16. The method of embodiment B15, wherein the heterocyclic ring is a pyrrolidine, a piperidine, an azepane, or a morpholine.

B17. The method of any one of embodiments B8-B11, wherein $R_2$ is —$CH_2$-$A_1$ and $A_1$ is an unsubstituted phenyl or a phenyl substituted with one or more $R_A$.

B18. The method of embodiment B17, wherein $R_A$ is halogen.

B19. The method of embodiment B17, wherein $R_A$ is —O—$R_9$.

B20. The method of any one of embodiments B8-B19, wherein at least one of a and b represents a single bond and the other of a and b independently represents either a single bond or a double bond.

B21. The method of any one of embodiments B8-B19, wherein both a and b represent a single bond.

B22. The method of any one of embodiments B8-B19, wherein both a and b represent a double bond.

B23. The method of embodiment B8, wherein at least one of a and b represents a single bond and the other of a and b independently represents either a single bond or a double bond.

B24. The method of embodiment B8, wherein both a and b represent a single bond.

B25. The method of embodiment B8, wherein both a and b represent a double bond.

B26. The method of any one of embodiments B23-B25, wherein $R_1$ is —C(O)$CH_3$ and $R_2$ is

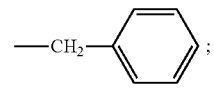

$R_1$ is —C(O)$CH_3$ and $R_2$ is

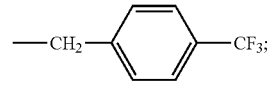

$R_1$ is —C(O)$CH_3$ and $R_2$ is

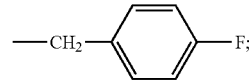

$R_1$ is —C(O)$CH_3$ and $R_2$ is

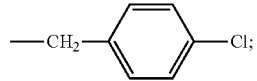

$R_1$ is —C(O)CH($CH_3$)$_2$ and $R_2$ is

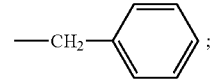

$R_1$ is —C(O)CH($CH_3$)$_2$ and $R_2$ is

$R_1$ is —C(O)CH($CH_3$)$_2$ and $R_2$ is

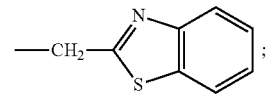

$R_1$ is —C(O)CH($CH_3$)$_2$ and $R_2$ is

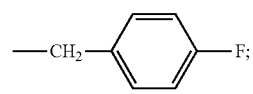

$R_1$ is —C(O)CH($CH_3$)$_2$ and $R_2$ is

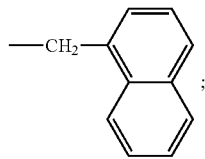

$R_1$ is hydrogen and $R_2$ is

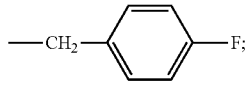

$R_1$ is —C(O)($CH_2$)$_3$$CH_3$ and $R_2$ is

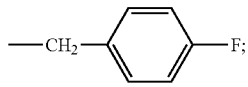

$R_1$ is —C(O)$CH_3$ and $R_2$ is —C(O)C($CH_3$)$_3$;
$R_1$ is —C(O)CH($CH_3$)$_2$ and $R_2$ is —C(O)C($CH_3$)$_3$;
$R_1$ is hydrogen and $R_2$ is —C(O)C($CH_3$)$_3$;
$R_1$ is —C(O)$CH_3$ and $R_2$ is —C(O)N($CH_2CH_3$)$_2$;
$R_1$ is —C(O)$CH_3$ and $R_2$ is —C(O)N($CH_3$)($C_6H_5$);
$R_1$ is —C(O)$CH_3$ and $R_2$ is

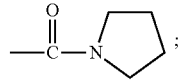

$R_1$ is —C(O)CH($CH_3$)$_2$ and $R_2$ is —C(O)N($CH_2CH_3$)$_2$;
$R_1$ is hydrogen and $R_2$ is —C(O)N($CH_2CH_3$)$_2$;
$R_1$ is —C(O)$CH_3$ and $R_2$ is

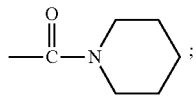

$R_1$ is —C(O)$CH_3$ and $R_2$ is

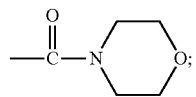

$R_1$ is —C(O)$CH_3$ and $R_2$ is —C(O)N(CH($CH_3$)$_2$)$_2$;
$R_1$ is —C(O)$CH_3$ and $R_2$ is —C(O)N(($CH_2$)$_3$$CH_3$)$_2$;
$R_1$ is —C(O)$CH_3$ and $R_2$ is —C(O)N(($CH_2$CH$CH_3$)$_2$)$_2$;
$R_1$ is —C(O)$CH_3$ and $R_2$ is

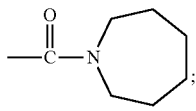

$R_1$ is —C(O)$CH_3$ and $R_2$ is

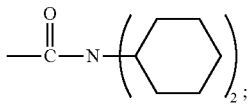

$R_1$ is —C(O)CH($CH_3$)$_2$ and $R_2$ is —C(O)N($CH_3$)$_2$;
$R_1$ is —C(O)CH($CH_3$)$_2$ and $R_2$ is —C(O)N($CH_2CH_3$)(($CH_2$)$_3$$CH_3$);
$R_1$ is hydrogen and $R_2$ is —C(O)N(CH($CH_3$)$_2$)$_2$;
$R_1$ is hydrogen and $R_2$ is —C(O)N(($CH_2$)$_3$$CH_3$)$_2$;
$R_1$ is H and $R_2$ is

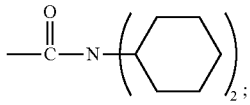

$R_1$ is —C(O)CH($CH_3$)$_2$ and $R_2$ is

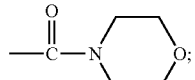

$R_1$ is —C(O)$CH_3$ and $R_2$ is

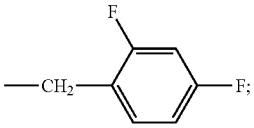

$R_1$ is —C(O)($CH_2$)$_3$($CH_3$) and $R_2$ is

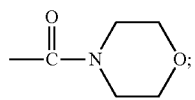

$R_1$ is —C(O)($CH_2$)$_3$($CH_3$) and $R_2$ is

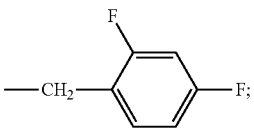

$R_1$ is hydrogen and $R_2$ is

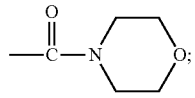

R₁ is hydrogen and R₂ is

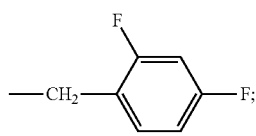

R₁ is hydrogen and R₂ is

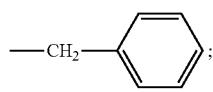

or
R₁ is hydrogen and R₂ is

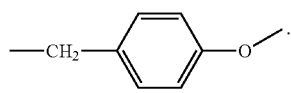

B27. The method of any one of embodiments B8-B26, wherein a compound of Formula (I-1) is administered to the subject.

B28. The method of any one of embodiments B8-B26, wherein a prodrug of a compound of Formula (I-1) is administered to the subject.

G. Examples

Example 1

In Vitro Assay

A C6/36 *Aedes albopictus* cell line infected with *Wolbachia pipientis* (*Wolbachia* strain wAlbB) derived from Aa23 *A. albopictus* cell line (O'Neill et al., 1997; Insect Mol Biol; Turner et al., (2006) J. Immunol. 7:1240-1249) was used to screen compounds. Cells were cultured in Leibovitz's L15 +L-glutamine supplemented with heat-inactivated Foetal Calf Serum (HI-FCS), non-essential amino acids and tryptose phosphate broth. Culture medium was filter-sterilized through a 0.2 μm filter and stored at 4° C. Compounds were provided as 10 mM stocks in DMSO, diluted to 50 μM working stock to give final concentration of 5 μM on the test plate. Concentrated stocks were frozen at −20° C.

Prior to use in the screening assay, cell cultures were sub-passaged (6 days prior) to provide ~90% confluent cells on Day 0 of screening assay. On Day 0 (assay set-up), the medium was removed from the stock culture flask and replaced with fresh medium. The cells were detached by scraping and cell density was calculated using an automated cell counter. The cells were then diluted at working density and aliquoted at 90 μl to each well of a Cell Carrier 384 well plate (Perkin Elmer). Cell plates were incubated at 26° C.

Control solution (DMSO-medium) was dispensed at 10 μl per well for "untreated" wells. Test solution (Drug-DMSO) was also dispensed at 10 μl (from working plate) per well for "treated" wells. The plates were incubated at 26° C., inside plastic wallet in incubator, for 7 days.

On Day 7, 25 μl of staining medium/dye (SYTO 11, Life Technologies) was added to each sample well and allowed to stain for 15 minutes in the dark. All the medium was removed from each sample well without disturbing the cells and replaced with 100 μl of fresh medium. Plates were imaged on the Operetta High Content Imaging system (Perkin Elmer) and analyzed using texture analysis through Harmony software (Perkin Elmer). The cell-based screen and analysis are described in detail in Clare et al. (2014) J Biomol Screen.

Tylosin A, Tylosin B, and Compounds 1-39 having structures as shown in Table 1A were tested for anti-*Wolbachia* activity:

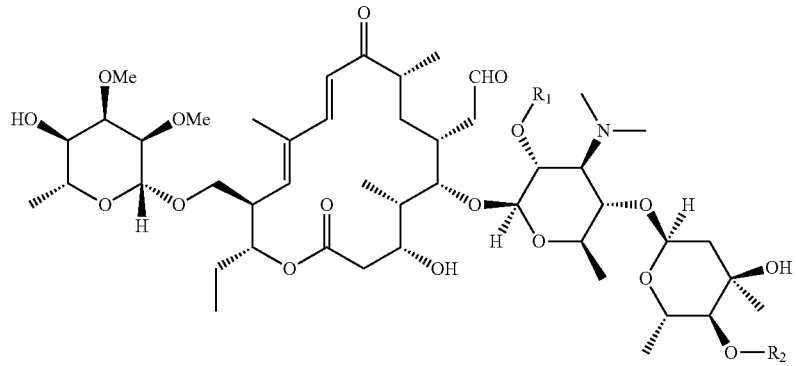

TABLE 1A

| Compound | R₁ | R₂ | EC₅₀ (nM) |
|---|---|---|---|
| Tylosin A | | | 36/24/26 |
| Tylosin B | | | 88 |
| 1 | C(O)CH₃ | —CH₂—⌬ | 0.6 |
| 2 | C(O)CH₃ | —CH₂—⌬—CF₃ | 6.2 |
| 3 | C(O)CH₃ | —CH₂—⌬—F | 1.1 |

TABLE 1A-continued

| Compound | R₁ | R₂ | EC₅₀ (nM) |
|---|---|---|---|
| 4 | C(O)CH₃ | —CH₂—(4-Cl-C₆H₄) | 6.5 |
| 5 | C(O)CH(CH₃)₂ | —CH₂—C₆H₅ | 13 |
| 6 | C(O)CH(CH₃)₂ | —CH₂—(2,4-diF-C₆H₃) | 25 |
| 7 | C(O)CH(CH₃)₂ | —CH₂—(benzothiazol-2-yl) | 29 |
| 8 | C(O)CH(CH₃)₂ | —CH₂—(4-F-C₆H₄) | 29 |
| 9 | C(O)CH(CH₃)₂ | —CH₂—(naphth-1-yl) | 181 |
| 10 | H | —CH₂—(4-F-C₆H₄) | <0.1 |
| 11 | C(O)(CH₂)₃CH₃ | —CH₂—(4-F-C₆H₄) | 44 |
| 12 | C(O)CH₃ | C(O)C(CH₃)₃ | 7.5 |
| 13 | C(O)CH(CH₃)₂ | C(O)C(CH₃)₃ | 33 |
| 14 | H | C(O)C(CH₃)₃ | 0.85 |
| 15 | C(O)CH₃ | C(O)N(CH₂CH₃)₂ | <1 |
| 16 | C(O)CH₃ | C(O)N(CH₃)(C₆H₅) | 15 |
| 17 | C(O)CH₃ | C(O)-pyrrolidinyl | 27 |
| 18 | C(O)CH(CH₃)₂ | C(O)N(CH₂CH₃)₂ | 25 |
| 19 | H | C(O)N(CH₂CH₃)₂ | 1.6 |
| 20 | C(O)CH₃ | C(O)-piperidinyl | 46 |
| 21 | C(O)CH₃ | C(O)-morpholinyl | 2.4 |
| 22 | C(O)CH₃ | C(O)N(CH(CH₃)₂)₂ | 269 |
| 23 | C(O)CH₃ | C(O)N((CH₂)₃CH₃)₂ | 331 |
| 24 | C(O)CH₃ | C(O)N(CH₂CH(CH₃)₂)₂ | 358 |
| 25 | C(O)CH₃ | C(O)-azepanyl | 15 |
| 26 | C(O)CH₃ | C(O)N(cyclohexyl)₂ | 1,700 |
| 27 | C(O)CH(CH₃)₂ | C(O)N(CH₃)₂ | 33 |
| 28 | C(O)CH(CH₃)₂ | C(O)N(CH₂CH₃)((CH₂)₃CH₃) | 282 |
| 29 | H | C(O)N(CH(CH₃)₂)₂ | 18 |
| 30 | H | C(O)N((CH₂)₃CH₃)₂ | 13 |
| 31 | H | C(O)N(cyclohexyl)₂ | 1,140 |
| 32 | C(O)CH(CH₃)₂ | C(O)-morpholinyl | 11 |
| 33 | C(O)CH₃ | —CH₂—(2,4-diF-C₆H₃) | 4.42 |
| 34 | C(O)(CH₂)₃(CH₃) | C(O)-morpholinyl | <10 |
| 35 | C(O)(CH₂)₃(CH₃) | —CH₂—(2,4-diF-C₆H₃) | 98 |
| 36 | H | C(O)-morpholinyl | 3 |
| 37 | H | —CH₂—(2,4-diF-C₆H₃) | <3 |
| 38 | H | —CH₂—C₆H₅ | <0.1 |
| 39 | H | —CH₂—(4-OCH₃-C₆H₄) | <0.1 |

Compounds 40-43 having structures as shown in Table 1B were tested for anti-*Wolbachia* activity:

TABLE 1B

| Compound | $R_1$ | $R_2$ | $EC_{50}$ (nM) |
| --- | --- | --- | --- |
| 40 | H | C(O)N(CH$_2$CH$_3$)$_2$ | 25 |
| 41 | C(O)CH(CH$_3$)$_2$ | C(O)N(CH$_2$CH$_3$)$_2$ | 81 |
| 42 | H | —CH$_2$—C$_6$H$_4$—F (4-F) | 10 |

TABLE 1B-continued

| Compound | $R_1$ | $R_2$ | $EC_{50}$ (nM) |
| --- | --- | --- | --- |
| 43 | H | —CH$_2$—C$_6$H$_3$—2,4-F$_2$ | 565 |

Compounds 44-55 having structures as shown in Table 1C were tested for anti-*Wolbachia* activity:

TABLE 1C

| Compound | $R_1$ | $R_2$ | $R_{10}$ | $EC_{50}$ (nM) |
| --- | --- | --- | --- | --- |
| 44 | C(O)CH$_3$ | C(O)N(CH$_2$CH$_3$)$_2$ | C(O)CH$_2$CH$_3$ | 3.50 |
| 45 | H | C(O)N(CH$_2$CH$_3$)$_2$ | C(O)CH$_2$CH$_3$ | 0.13 |
| 46 | C(O)CH$_2$CH$_3$ | C(O)N(CH$_2$CH$_3$)$_2$ | C(O)CH$_2$CH$_3$ | 2.93 |
| 47 | C(O)CH$_3$ | —CH$_2$—C$_6$H$_4$—F (4-F) | C(O)CH$_2$CH$_3$ | 1.79 |
| 48 | H | —CH$_2$—C$_6$H$_4$—F (4-F) | C(O)CH$_2$CH$_3$ | 0.41 |
| 49 | C(O)CH$_3$ | C(O)N(CH$_2$CH$_3$)$_2$ | C(O)CH$_3$ | 0.42 |
| 50 | H | C(O)N(CH$_2$CH$_3$)$_2$ | C(O)CH$_3$ | 0.25 |
| 51 | H | C(O)N(CH$_2$CH$_3$)$_2$ | C(O)CH(CH$_3$)$_2$ | 3.03 |

TABLE 1C-continued

| Compound | R$_1$ | R$_2$ | R$_{10}$ | EC$_{50}$ (nM) |
|---|---|---|---|---|
| 52 | C(O)CH$_3$ | —CH$_2$—C$_6$H$_4$—F 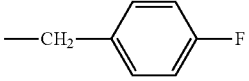 | C(O)CH$_3$ | 0.13 |
| 53 | H | —CH$_2$—C$_6$H$_4$—F 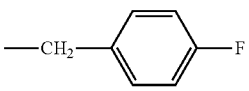 | C(O)CH$_3$ | 0.22 |
| 54 | C(O)CH$_3$ | —CH$_2$—C$_6$H$_4$—F 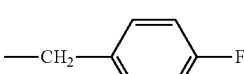 | C(O)CH(CH$_3$)$_2$ | 3.03 |
| 55 | H | —CH$_2$—C$_6$H$_4$—F 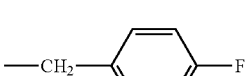 | C(O)CH(CH$_3$)$_2$ | 0.13 |

Example 2

Larval *Litomosoides sigmodontis* mouse model

In this mouse model of filariasis (Hoeraufa A, et al. (1999) Journal of Clinical Investigation 103(1):11-18), BALB/c mice (6-8 week old) were infected via natural larvae transmission, through the bite of infected tropical mites (*Ornithonyssus bacoti*), and treatment started on the day following infection. Anti-*Wolbachia* efficacy was measured by quantitative PCR analysis, using genomic DNA extracted from larvae, of the *Wolbachia* ftsZ gene, and expressed as a reduction in *Wolbachia* load in comparison to the vehicle control group. In the *Litomosoides sigmodontis* larval model, 7 days treatment with Tylosin A lead to *Wolbachia* reductions of 91.7% and 21.9%, with parenteral and oral dosing, respectively. Doxycycline treatment (50 mg/kg/day for 14 days) lead to a 99.9% *Wolbachia* reduction. Thus, tylosin A effectively cleared *Wolbachia* from filarial larvae (*Litomosoides sigmodontis*) in a mouse model of filariasis when delivered parenterally (intraperitoneally), to a similar extent to doxycycline, with a shorter dosing regimen.

Example 3

Larval *Brugia malayi* Mouse Model

In a larval *Brugia malayi* mouse model treatment groups (BALB/c IL4Rα-/- mice, 6-8 week old) received compounds by oral delivery for 7 to 14 days commencing on the day of intraperitoneal infection with *Brugia malayi* third-stage larvae. At 14 days post-infection, larvae were recovered from the peritoneal cavity, counted, and length measured. Genomic DNA was extracted from individual worms (10/group) and quantification of the *Wolbachia* surface protein (wBm-wsp) gene copy numbers performed by quantitative PCR.

Table 2 shows *Wolbachia* reductions in *Brugia malayi* larval infection mouse model (% compared to median vehicle control) following treatment with tylosin A ("TYL A"), Compound 18, or Compound 19. Treatment dose (mg/kg) shown in parentheses and duration stated in days (d). Abbreviations: DOX (doxycycline), bid (twice daily), qd (once daily), PO (oral), IP (parenteral). Data in Table 2 are expressed as a reduction in *Wolbachia* load in comparison to the vehicle control group.

TABLE 2

| Treatment (mg/kg) | % *Wolbachia* reduction |
|---|---|
| DOX (50 qd) PO 7 d | 88.7% |
| DOX (50 qd) PO 14 d | 98.3% |
| TYL A (50 qd) IP 14 d | 99.9% |
| TYL A (50 qd) PO 14 d | 50.4% |
| Compound 19 (50 qd) PO 7 d | 99.8% |
| Compound 19 (50 qd) PO 14 d | 99.9% |
| Compound 19 (25 qd) PO 14 d | 99.8% |
| Compound 18 (50 qd) PO 7 d | 98.0% |
| Compound 18 (50 qd) PO 14 d | 99.6% |
| Compound 18 (25 qd) PO 14 d | 81.8% |

In this larval model, Compound 19 reduced the *Wolbachia* load by 99.9% at two weeks post-infection, when dosed once daily (qd) at 50 mg/kg/day orally for 14 days. At a lower dose of 25 mg/kg/day, the *Wolbachia* load was also reduced by 99.8%. Both results are superior to doxycycline given at 50 mg/kg/day for 14 days (98.3% reduction). When Compound 19 was given at 50 mg/kg/day for 7 days, *Wolbachia* load was still reduced by 99.8% (Table 2). Tylosin A (50 mg/kg/day) showed comparable anti-*Wolbachia* efficacy when dosed intraperitoneally for 14 days (99.9%) but was not sufficiently effective when dosed orally (50.4%) (Table 2).

Additional compounds were tested in the larval mouse model of filarial disease at both 25 and 50 mg/kg/day for 7 days (Table 3). Table 3 shows *Wolbachia* reductions in *Brugia malayi* larval infection mouse model (% compared to median vehicle control) following oral treatment with compounds disclosed herein. Treatment dose (mg/kg) shown in parentheses and duration stated in days (d). Abbreviations: DOX (doxycycline), qd (once daily).

TABLE 3

| Treatment (mg/kg) | Weighted exposure ng-hr/mL/nM | % *Wolbachia* reduction |
|---|---|---|
| DOX (50 qd) 7 d | ND | 77.4% |
| DOX (50 qd) 14 d | ND | 99.3% |
| Compound 19 (25 qd) 7 d | 5,400 | 99.4% |
| Compound 19 (50 qd) 7 d | 15,000 | 99.6% |
| Compound 10 (25 qd) 7 d | 900 | 97.9% |
| Compound 10 (50 qd) 7 d | 13,500 | 99.5% |
| Compound 37 (25 qd) 7 d | 1,200 | 73.6% |
| Compound 37 (50 qd) 7 d | 4,000 | 91.3% |
| Compound 18 (25 qd) 7 d | 240 | 54.3% |

TABLE 3-continued

| Treatment (mg/kg) | Weighted exposure ng-hr/mL/nM | % Wolbachia reduction |
|---|---|---|
| Compound 18 (50 qd) 7 d | 700 | 98.2% |
| Compound 8 (25 qd) 7 d | 27 | 0% |
| Compound 8 (50 qd) 7 d | 97 | 0% |
| Compound 34 (25 qd) 7 d | 1,220 | 43.5% |
| Compound 34 (50 qd) 7 d | 5,700 | 93.9% |

Compound 10 reduced the *Wolbachia* load by 99.5% at two weeks post-infection, when dosed at 50 mg/kg/day orally for 7 days. At a lower dose of 25 mg/kg/day, the *Wolbachia* load was reduced by 97.9%. These reductions compare with the corresponding values for Compound 19 (99.6% and 99.4%, respectively) in this study. All results are superior to doxycycline given at 50 mg/kg/day for 7 days (77.4% reduction); all but the lower dose of Compound 10 are comparable or superior to doxycycline 50 mg/kg/day for 14 days (99.3% reduction). Thus, compounds disclosed herein appear to offer both improved efficacy and the potential for a shorter course of treatment over both tetracycline and doxycycline.

Example 4

Adult *Brugia malayi* Mouse Model

In an adult *Brugia malayi* mouse model treatment groups (BALB/c CCR3−/−mice, 6-8 week old) received compounds by oral delivery for 7-28 days beginning at 6-10 weeks post-infection intraperitoneal with *Brugia malayi* third-stage larvae. Following treatment, at 12 weeks post-infection, adult worms and released microfilariae were recovered from the peritoneal cavity, counted and staged for sex. Genomic DNA was extracted from individual adult worms (10/group) and quantification of the *Wolbachia* surface protein (wBm-wsp) performed by quantitative PCR.

Table 4 shows *Wolbachia* reductions in *Brugia malayi* adult infection model (% reduction compared to median vehicle control) following oral treatment with tylosin A ("TYL A") and Compound 19. Treatment dose (mg/kg/day) shown in parentheses and duration stated in days (d). MIN (minocycline), bid (twice daily), qd (once daily). Data in Table 4 are expressed as a reduction in *Wolbachia* load in comparison to the vehicle control group.

TABLE 4

| Treatment (mg/kg) | % Wolbachia reduction |
|---|---|
| MIN (25 bid) 28 d | 83.8% |
| TYL A (50 qd) 14 d | 0% |
| Compound 19 (50 qd) 7 d | 43.1% |
| Compound 19 (50 qd) 14 d | 73.4% |

Compound 19 was tested in the adult *Brugia malayi* mouse model and was effective against *Wolbachia* (Table 4). Compound 19 given for 14 days at 50 mg/kg/day orally decreased *Wolbachia* load by 73.4% in this model, and thus is comparable to the tetracycline, minocycline, given at the same dose (25 mg/kg twice a day) for a duration of 28 days (83.8%). In a separate study using this adult *Brugia malayi* mouse model, it has been determined that minocycline is superior to doxycycline, dose-for-dose. Adult worm recoveries did not vary significantly between Compound 19 treatment and control groups. Again, this result suggests that compounds disclosed herein may provide clinical benefit with a shorter dosing regimen. PK samples were taken at selected time points during day 1 and day 7 following dosing with Compound 19 (50 mg/kg/day) and the PK profiles showed an increase in the circulating concentrations of Compound 19 after multiple dosing.

A dose escalation study of Compound 19 showed that both 150 and 250 mg/kg daily oral treatment resulted in a >90% *Wolbachia* reduction (Table 5), and that the higher dose treatment (250 mg/kg/day) can reduce the treatment time to 7 days in order to achieve >90% *Wolbachia* reduction in adult female worms (98.3% reduction) (Table 5). This demonstrates comparable anti-*Wolbachia* efficacy of Compound 19 to a minocycline treatment regimen of 25 mg/kg bid for 28 days. Thus, compounds disclosed herein may allow for a reduced treatment duration and, in particular, may be suitable for a treatment period of 7 days or less.

Table 5 shows *Wolbachia* reductions in *Brugia malayi* adult infection mouse model (% reduction compared to median vehicle control) following oral treatment with Compound 19 in a dose escalation study. Treatment dose (mg/kg/day) shown in parentheses and duration stated in days (d). MIN (minocycline), bid (twice daily), qd (once daily).

TABLE 5

| Treatment (mg/kg) | % Wolbachia reduction |
|---|---|
| MIN (25 bid) 28 d | 95.5% |
| Compound 19 (150 qd) 14 d | 90.0% |
| Compound 19 (250 qd) 14 d | 96.8% |
| Compound 19 (250 qd) 7 d | 98.3% |

Example 5

Adult *Brugia malayi* Jird Model

In this model of adult filarial (macrofilariae) infection, Mongolian jirds (*Meriones unguiculatus*) were infected intraperitoneally with *Brugia malayi* third-stage larvae (Ash and Riley, (1970) J Parasitol. 56(5):969-73). Infected jirds were treated at +12-20 weeks post-infection for periods up to 6 weeks. Jirds were necropsied for worm recoveries. Adult worms were staged for sex and motile released microfilariae were counted. Genomic DNA was extracted from individual worms (10/group) and quantification of the *Wolbachia* surface protein (wBm-wsp) and *Brugia malayi* glutathione S-transferase (Bm-gst) gene copy numbers performed by quantitative PCR, and expressed as a reduction in *Wolbachia* load in comparison to the vehicle control group.

Treatment with Compound 10 in the adult *Brugia malayi* jird model showed that treatment with both 10 and 50 mg/kg daily oral treatment for 14 days resulted in a >90% *Wolbachia* reduction (Table 6).

Table 6 shows *Wolbachia* reductions in *Brugia malayi* adult infection jird model (% reduction compared to median vehicle control) following oral treatment with Compound 10. Treatment dose (mg/kg/day) shown in parentheses and duration stated in days (d). DOX (doxycycline), qd (once daily).

TABLE 6

| Treatment (mg/kg) | % Wolbachia reduction |
|---|---|
| DOX (200 qd) 21 d | 99.1% |
| Compound 10 (10 qd) 14 d | 99.4% |
| Compound 10 (50 qd) 14 d | 99.8% |

These results demonstrate that compounds disclosed herein, administered for a reduced treatment duration, have comparable anti-*Wolbachia* efficacy to doxycycline treatment of 200 mg/kg/day for 21 days.

Table 7 shows reductions in motile peritoneal microfilariae load in *Brugia malayi* adult infection jird model (% reduction compared to median vehicle control) following oral treatment with Compound 10. Treatment dose (mg/kg/day) shown in parentheses and duration stated in days (d). DOX (doxycycline), qd (once daily).

TABLE 7

| Treatment (mg/kg) | % reduction in microfilariae |
| --- | --- |
| DOX (200 qd) 21 d | 90.5% |
| Compound 10 (10 qd) 14 d | 70.1% |
| Compound 10 (50 qd) 14 d | 99.6% |

In addition to its anti-*Wolbachia* efficacy, treatment with Compound 10 in the adult *Brugia malayi* jird model lead to a reduction in motile peritoneal microfilariae load (Table 7). Compound 10 showed a dose-dependent reduction in motile microfilariae recovered from the peritoneum, 70.1% and 99.6% reduction with 10 and 50 mg/kg daily oral treatment, respectively.

Thus, compounds disclosed herein are effective against *Wolbachia* in preclinical models of filarial brugian lymphatic filariasis worm infection. Moreover, compounds disclosed herein offer the potential for a shorter course of treatment over the standard of care with tetracycline or doxycycline.

Example 6

Adult *Onchocerca ochengi* Mouse Model

In this model, adult male *Onchocerca ochengi* (closest relative species to the human parasite causing river blindness, *Onchocerca volvulus*) are derived from cattle natural hosts and surgically implanted into the peritoneal cavity of CB.17 SCID (BALB/c congenic) mice under anaesthesia (Halliday et al Parasit. Vectors 2014 7:472). After 3 days following surgery, mice were treated by oral gavage for periods up to 4 weeks. Mice were necropsied for worm recoveries 6 weeks after start of treatment. Genomic DNA was extracted from individual worms (n=10/group) and quantification of the *Wolbachia* surface protein (wBm-wsp) and *Onchocerca* glutathione S-transferase (Ov-gst) gene copy numbers performed by quantitative PCR. Data is expressed as a reduction in *Wolbachia*:gst ratios in comparison to the vehicle control group.

Table 8 shows reductions in *Wolbachia* load in *Onchocerca ochengi* adult male mouse model (% reduction compared to median vehicle control) following oral treatment with Compound 10 and Compound 19. Treatment dose (mg/kg/day) shown in parentheses and duration stated in days (d). DOX (doxycycline), qd (once daily) bid (twice daily).

TABLE 8

| Treatment (mg/kg) | % *Wolbachia* reduction |
| --- | --- |
| DOX (25 bid) 28 d | 99.8% |
| MIN (25 bid) 28 d | 99.7% |
| Compound 19 (250 qd) 14 d | 99.7% |
| Compound 10 (75 qd) 07 d | 97.2% |

Both Compound 10 and Compound 19 mediated a superior effect to the tetracyclines, DOX and MIN, by reducing *Wolbachia* loads in adult male *Onchocerca* beyond 90% in a shortened dose timeframe. Compound 19 reduced *Wolbachia* by 99.7% following 14 days dosing at 250 mg/kg (qd). Compound 10 reduced *Wolbachia* by 97.2% following 07 days dosing at 75 mg/kg (qd).

Thus, compounds disclosed herein are effective against *Wolbachia* in a preclinical model of onchocerciasis worm infection. Moreover, compounds disclosed herein offer the potential for a shorter course of treatment over the standard of care with doxycycline or minocycline.

Example 7

*Loa loa* Microfilariae Ex Vivo Counter-Screen

This ex vivo assay is used to assess direct *Loa loa* microfilaricidal effects of drug compounds. Bloodborne *Loa loa* microfilariae are generated from experimental infections of splenectomised baboons with the human stain of *L. loa* (Orihel et al, Trop Med Parasitol, 1985. 36: p.215). *L. loa* microfilariae were purified from venous blood samples by Percoll gradient centrifugation. *Loa loa* microfilariae were adjusted to a density of $0.5 \times 10^4$/ml and plated into 96-well plates in Dulbecco's Modified Eagle Medium (DMEM) containing 10% Foetal Calf Serum (FCS). Triplicate wells of *Loa loa* microfilariae were exposed to either ivermectin (64 µg/ml: positive control), compound 10 (0.018 and 0.18 µg/ml), compound 19 (0.11 and 1.11 µg/ml) or 0.1% DMSO vehicle control. Dose levels of compound 10 and compound 19 were matched to predictive $C_{max}$ and $10\times C_{max}$ human plasma concentrations based on PK-PD modeling. *L. loa* were cultured at 37° C./5% $CO_2$ for +7 days and monitored daily with a semi-quantitative score applied to individual mf motility.

Table 9 shows changes in *L. loa* microfilariae motility at indiciated time-points (days) compared with baseline in cultures treated with vehicle solvent only (VC), ivermectin (IVM), compound 10 or compound 19.

TABLE 9

| Treatment (µg/ml) | Exposure time (days) | Motility (mean % vs baseline) | Survival (%) |
| --- | --- | --- | --- |
| VC (—) | 2 | 98.27 | 100 |
|  | 7 | 80.91 | 100 |
| IVM (64) | 2 | 5.71 | 100 |
|  | 7 | 0 | 0 |
| Cmpd 10 (0.018/0.18) | 2 | 98.01/98.06 | 100 |
|  | 7 | 84.31/84.71 | 100 |
| Cmpd 19 (0.11/1.1) | 2 | 97.54/99.24 | 100 |
|  | 7 | 86.56/84.77 | 100 |

Both compound 10 and compound 19 showed no effect in cessating microfilariae motility compared with IVM, which rendered microfilariae completely immotile after a period of 7 days. Further, both compound 10 and compound 19 did not alter degree of motility compared with VC at +2 or +7 days in contrast to IVM which induced >90% reduction in motility in +2 days.

Thus, compounds disclosed herein are ineffective against *Loa loa* microfilariae in an ex vivo assay of microfilaricidal assessment. This indicates the compounds disclosed herein offer the potential for safe treatment of patients co-infected with loaisis and onchocerciasis or lymphatic filariasis.

Example 8

Compounds Having Structures as Shown in Tables 1A, 1B, and 1C were Prepared as Described Below

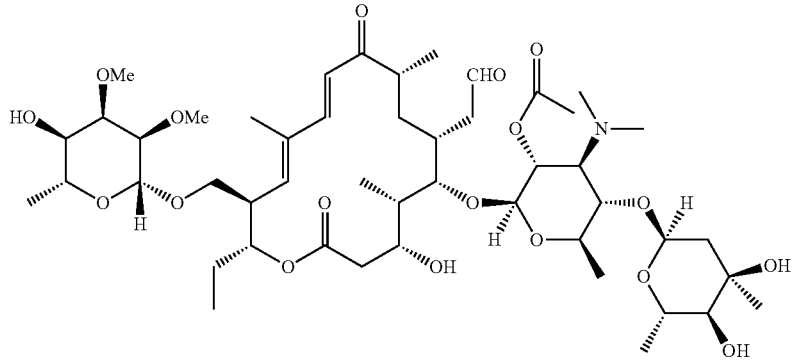 [SMILES: CC[C@H]1OC(=O)C[C@@H](O)[C@H](C)[C@@H](O[C@@H]2O[C@H](C)[C@@H](O[C@H]3C[C@@](C)(O)[C@@H](O)[C@H](C)O3)[C@H](N(C)C)[C@H]2OC(C)=O)[C@@H](CC=O)C[C@@H](C)C(=O)/C=C/C(C)=C/[C@@H]1CO[C@@H]1O[C@H](C)[C@@H](O)[C@@H](OC)[C@H]1OC]

Compound A. Tylosin A 2'-OAc

Using a modification of the procedures described in Tsuchiya et al, J Antibiotics 1982, (35), 661, tylosin A tartrate (5 mmol) was dissolved in 20 mL of ethanol; acetic anhydride (0.66 mL, 1.5 equivalents) was added and the resultant solution was stirred at 40° C. for four hours. Reaction was quenched by addition of 20 mL of aqueous sodium bicarbonate; the mixture was stirred for 30 minutes, then poured into a separatory funnel and the organic layer was removed. The aqueous layer was extracted twice with 10 mL of chloroform. The combined organic layers were washed with brine and dried over $Na_2SO_4$. The crude product was carried forward without further purification.

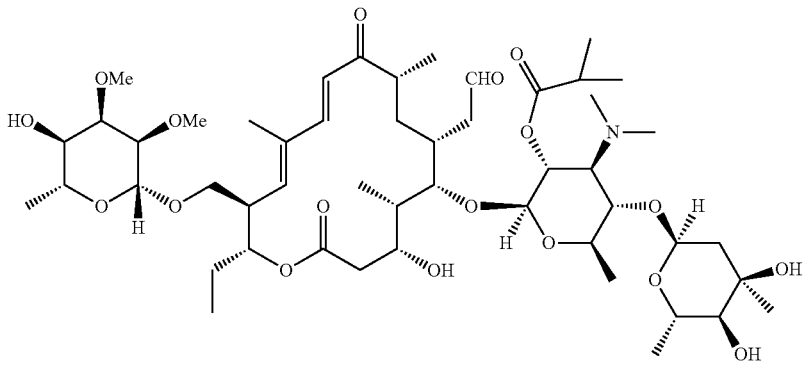 [SMILES: CC[C@H]1OC(=O)C[C@@H](O)[C@H](C)[C@@H](O[C@@H]2O[C@H](C)[C@@H](O[C@H]3C[C@@](C)(O)[C@@H](O)[C@H](C)O3)[C@H](N(C)C)[C@H]2OC(=O)C(C)C)[C@@H](CC=O)C[C@@H](C)C(=O)/C=C/C(C)=C/[C@@H]1CO[C@@H]1O[C@H](C)[C@@H](O)[C@@H](OC)[C@H]1OC]

Compound B Tylosin A 2'-OiBu

Compound B was prepared using procedure for the preparation of Compound A, except for substituting isobutyric anhydride (3.0 equivalents) for acetic anhydride, and using chloroform as solvent.

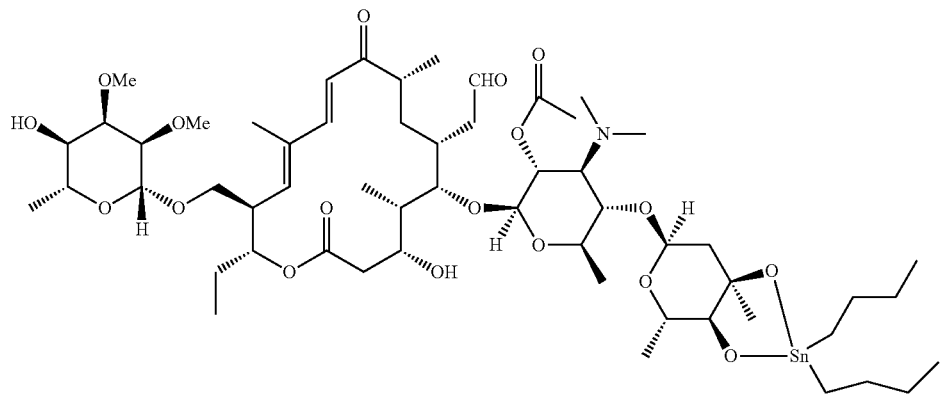

Compound C Tylosin A 2'-OAc, 3"/4" Dibutyl Tin Reagent

Using a modification of the procedures described in Kiyoshima et al., Chem. Pharm. Bull. 1989, 37(4), 861, Compound A (10 mmol) was dissolved in 150 mL of toluene; followed by the addition of 7.5 g (3.0 equivalents) of dibutyltin oxide. The resultant mixture was stirred at reflux (bath temperature 115° C.) for 30 minutes. A still head was added and the bath temperature was raised to 130° C., distilling off solvents to a final volume of about 60 mL. The resultant solution was used for further reactions without additional purification.

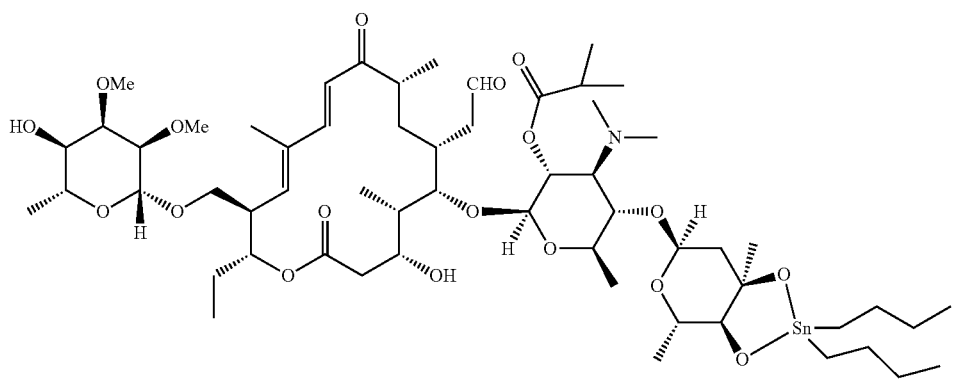 [SMILES: CCC[CH2][Sn]1([CH2]CCC)[O][C@H]2[C@H](C)O[C@@H](O[C@H]3[C@H](N(C)C)[C@@H](OC(=O)C(C)C)[C@H](O[C@H]4[C@@H](CC=O)C[C@@H](C)C(=O)/C=C/C(C)=C/[C@H](CO[C@@H]5O[C@H](C)[C@@H](O)[C@@H](OC)[C@H]5OC)[C@@H](CC)OC(=O)C[C@@H](O)[C@@H]4C)O[C@@H]3C)C[C@@]2(C)[O]1]

Compound D Tylosin A 2'-OiBu, 3"/4" Dibutyl Tin Reagent

Using a modification of the procedures described in Kiyoshima et al., Chem. Pharm. Bull. 1989, 37(4), 861, Compound B (10 mmol) was dissolved in 150 mL of toluene; followed by the addition of 7.5 g (3.0 equivalents) of dibutyltin oxide. The resultant mixture was stirred at reflux (bath temperature 115° C.) for 30 minutes. A still head was added and the bath temperature was raised to 130° C., distilling off solvents to a final volume of about 60 mL. The resultant solution was used for further reactions without additional purification.

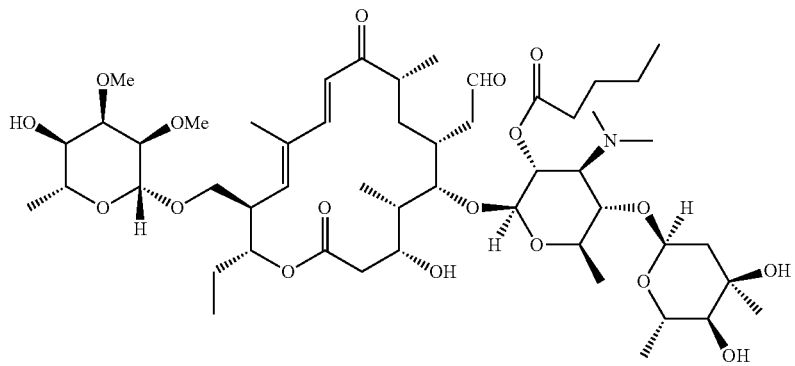 [SMILES: CCCCC(=O)O[C@H]1[C@H](O[C@H]2[C@@H](CC=O)C[C@@H](C)C(=O)/C=C/C(C)=C/[C@H](CO[C@@H]3O[C@H](C)[C@@H](O)[C@@H](OC)[C@H]3OC)[C@@H](CC)OC(=O)C[C@@H](O)[C@@H]2C)O[C@H](C)[C@@H](O[C@H]2C[C@@](C)(O)[C@@H](O)[C@H](C)O2)[C@@H]1N(C)C]

Compound E. Tylosin A 2'-OVal

Using a modification of the procedures described in Tsuchiya et al, J Antibiotics 1982, (35), 661, tylosin A tartrate (3 mmol) was dissolved in 15 mL of chloroform; valeric anhydride (0.89 mL, 1.5 equivalents) was added and the resultant solution was stirred at ambient temperature for 41 hours. Reaction was quenched by addition of 5 mL of aqueous sodium bicarbonate; the mixture was stirred for 30 minutes, then poured into a separatory funnel and the organic layer was removed. The aqueous layer was extracted with 5 mL of chloroform. The combined organic layers were washed with brine and dried over $Na_2SO_4$. The crude product was carried forward without further purification.

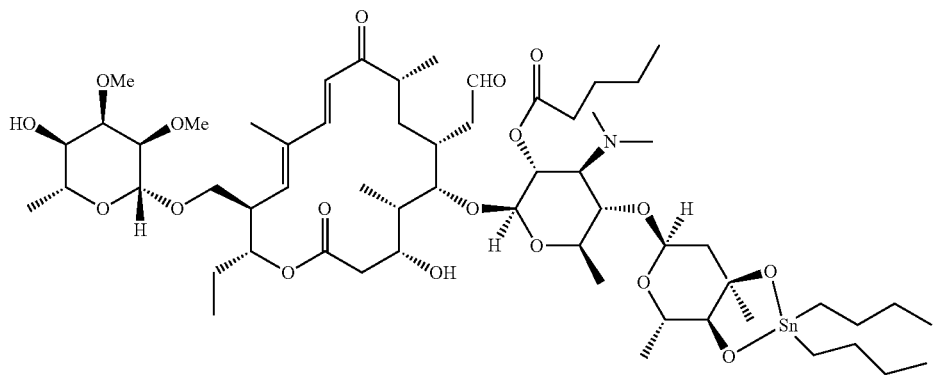

Compound F Tylosin A 2'-OVal, 3"/4" Dibutyl Tin Reagent

Using a modification of the procedures described in Kiyoshima et al., Chem. Pharm. Bull. 1989, 37(4), 861, Compound E (3 mmol) was dissolved in 50 mL of toluene; followed by the addition of 2.24 g (3.0 equivalents) of dibutyltin oxide. The resultant mixture was stirred at reflux (bath temperature 115° C.) for 30 minutes. A still head was added and the bath temperature was raised to 130° C., distilling off solvents to a final volume of about 20 mL. The resultant solution was used for further reactions without additional purification.

Compound H 2'-OAc, 10,11,12,13-tetrahydro-Tylosin A

Compound G (1.53 g) was dissolved in 10 mL of ethanol; 0.25 mL of acetic anhydride was added, and the resultant solution was stirred at 40° C. for 2 hours. The solution was concentrated in vacuo; the residue was taken up in chloroform and stirred with aqueous sodium bicarbonate solution for ten minutes. The mixture was poured into a separatory funnel; the organic layer was removed and the aqueous layer was extracted with chloroform. The combined organic layers were dried over solid sodium sulfate, filtered and concentrated in vacuo to give the title compound.

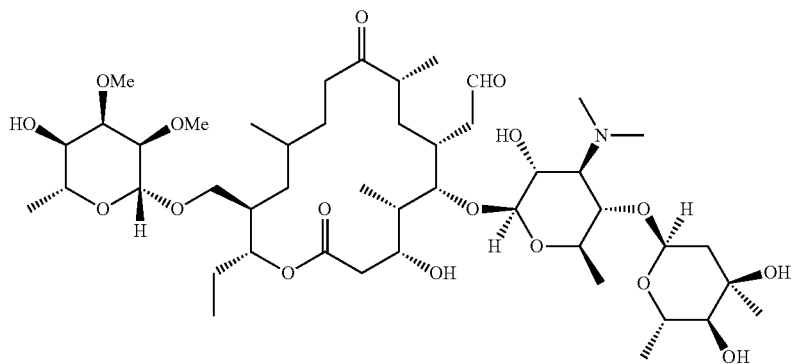 [SMILES: CC[C@H]1OC(=O)C[C@@H](O)[C@H](C)[C@@H](O[C@@H]2O[C@H](C)[C@@H](O[C@H]3C[C@@](C)(O)[C@@H](O)[C@H](C)O3)[C@H](N(C)C)[C@H]2O)[C@@H](CC=O)C[C@@H](C)C(=O)CCC(C)C[C@@H]1CO[C@@H]1O[C@H](C)[C@@H](O)[C@@H](OC)[C@H]1OC]

Compound G 10,11,12,13-tetrahydro-Tylosin A

The title compound was prepared according to the procedure of Narandja et al., J. Antibiotics 1995, 48930, 248.

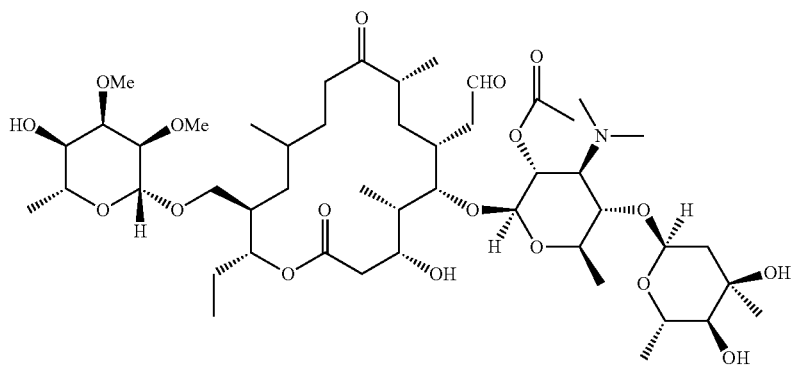 [SMILES: CC[C@H]1OC(=O)C[C@@H](O)[C@H](C)[C@@H](O[C@@H]2O[C@H](C)[C@@H](O[C@H]3C[C@@](C)(O)[C@@H](O)[C@H](C)O3)[C@H](N(C)C)[C@H]2OC(C)=O)[C@@H](CC=O)C[C@@H](C)C(=O)CCC(C)C[C@@H]1CO[C@@H]1O[C@H](C)[C@@H](O)[C@@H](OC)[C@H]1OC]

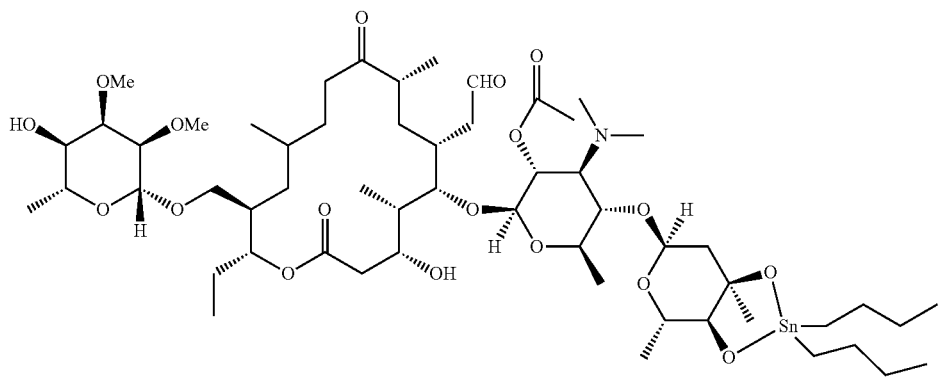

Compound J 2'-OAc, 10,11,12,13-tetrahydro-Tylosin A, Tin Reagent

Using a modification of the procedures described in Kiyoshima et al., Chem. Pharm. Bull. 1989, 37(4), 861, Compound J (1.60 g) was dissolved in 25 mL of toluene; followed by the addition of 0.62 g (1.5 equivalents) of dibutyltin oxide. The resultant mixture was stirred at reflux (bath temperature 115° C.) for 30 minutes. A still head was added and the bath temperature was raised to 140° C., distilling off solvents to a final volume of about 10 mL. The resultant solution was used for further reactions without additional purification.

Compound 1

Compound C (1 mmol) in 6 mL toluene solution, was combined with benzyl bromide (1.5 equivalents) and 20 mg of tetra-n-butylammonium iodide. The resultant mixture was heated at 90° C. for 2 days. Reaction was quenched with aqueous sodium bicarbonate and stirred for ten minutes. The layers were separated and the organic layer was washed with brine. Combined aqueous layer was extracted with chloroform. Combined organic layers were dried over $Na_2SO_4$, filtered, and concentrated. The residue was chromatographed on a 50 g silica gel column, eluting with a gradient from 1:1 ethyl acetate/hexanes to 100% ethyl acetate. The title compound was collected as a white solid.

Compound 2

Compound 2 was prepared using the procedure for the preparation of Compound 1, except for substituting 4-trifluoromethylbenzyl bromide for benzyl bromide. The crude product was purified by HPLC on a Waters Sunfire C8 column, eluting with a gradient of 35%/50%/87%/100% methanol in 0.1% ammonium acetate.

Compound 3

Compound C (1.25 mmol) in 20 mL toluene solution, was combined with 4-fluorobenzyl bromide (2.0 equivalents) and 200 mg of tetra-n-butylammonium iodide. The resultant mixture was heated at 90° C. for 2 days. The reaction mixture was concentrated in vacuo; the residue was chromatographed on a 50 g silica gel column, eluting with a gradient from 20% ethyl acetate/hexanes to 100% ethyl acetate, producing the title compound.

Compound 4

Compound 4 was prepared using the procedure for the preparation of Compound 1, except for substituting 4-chlorobenzyl bromide for benzyl bromide. The crude product was purified by HPLC on a Waters Sunfire C8 column, eluting with a gradient of 35%/50%/87%/100% methanol in 0.1% ammonium acetate.

Compound 5

Compound 5 was prepared using the procedure for the preparation of Compound 1, except for substituting Compound D for Compound C. The crude product was purified by chromatography on a silica gel column, eluting with a gradient from 20% ethyl acetate/hexanes to 100% ethyl acetate.

Compound 6

Compound D (1.5 mmol) in 10 mL toluene solution, was combined with 2,4-difluorobenzyl bromide (2.5 equivalents) and 20 mg of tetra-n-butylammonium iodide. The resultant mixture was heated at 90° C. for 3 days. The solvents were removed in vacuo; the residue was chromatographed on a 50 g silica gel column, eluting with a gradient from 1:1 ethyl acetate/hexanes to 100% ethyl acetate, to produce the title compound.

Compound 7

Compound 7 was prepared using the procedure for the preparation of Compound 1, except for substituting Compound D for Compound C, and substituting 2-bromomethyl benzothiazole for benzyl bromide. The crude product was purified by HPLC on a Waters Sunfire C8 column, eluting with a gradient of 20%/60%/100% methanol in 0.1% ammonium acetate.

Compound 8

Compound D (4.7 mmol) in 20 m L of toluene, was combined with 4-fluorobenzyl bromide (2.0 eq) and 200 mg of tetra-n-butylammonium iodide. The resultant mixture was warmed at 90° C. for 60 hours. Solvents were removed in vacuo; the residue was chromatographed on a 100 g silica gel column, eluting with a gradient from 20% ethyl acetate/hexanes to 100% ethyl acetate, giving the title compound.

Compound 9

Compound 9 was prepared using the procedure for the preparation of Compound 1, except for substituting Compound D for Compound C, and substituting 1-naphthylmethyl bromide for benzyl bromide. The crude product was chromatographed on a 10 g silica column, eluting with a gradient from 20% ethyl acetate/hexanes to 100% ethyl acetate.

Compound 10

Compound 3 (5.0 mmol) was dissolved in 80 mL of methanol; 50 mg of solid sodium bicarbonate was added, and the resultant mixture was stirred at ambient temperature for 5 days. Solvents were removed in vacuo; the residue was chromatographed on a 50 g silica gel column, eluting with a gradient from 1:1 ethyl acetate/hexanes to ethyl acetate, providing the title compound.

Compound 11

Compound 10 (58 mg, 0.06 mmol) was dissolved in 0.5 mL of chloroform; three drops of valeric anhydride was added, and the solution was stirred at ambient temperature for 3 hours. Reaction was quenched with aqueous sodium bicarbonate; the resultant mixture was stirred for 10 minutes. The organic phase was removed and concentrated in vacuo. The crude product was purified by HPLC on a Waters Sunfire C8 column, eluting with a gradient of 60% to 100% acetonitrile in 0.1% ammonium acetate.

Compound 12

A solution of Compound C (1 mmol) in 20 mL of toluene was combined with pivaloyl chloride (0.18 g, 1.5 equivalents) and heated at 90° C. for 6 hours. Reaction was quenched by addition of aqueous sodium bicarbonate, the resultant mixture was stirred for ten minutes. The organic layer was separated and washed with brine. The combined aqueous layers was extracted with $CHCl_3$. The combined organic extracts were dried over $Na_2SO_4$, filtered, and concentrated. The residue was chromatographed on a 50 g silica column, eluting with a gradient of 1:1 ethyl acetate/hexane to 100% ethyl acetate to provide the title compound as a white solid.

Compound 13

Compound D (1 mmol) in 20 mL of toluene was combined with pivaloyl chloride (0.24 g, 2.0 equivalents) and heated at 90° C. for 4 hours. Reaction was quenched by the addition of aqueous sodium bicarbonate, the resultant mixture was stirred for ten minutes. The organic layer was separated and washed with brine. The combined aqueous layers was extracted with $CHCl_3$. The combined organic extracts were dried over $Na_2SO_4$, filtered, and concentrated. The residue was chromatographed on a 50 g silica column, eluting with a gradient of 1:1 ethyl acetate/hexane to 100% ethyl acetate to provide the title compound as a white solid.

Compound 14

Compound 12 (1.04 g, 1 mmol) was dissolved in methanol (20 mL). The mixture was heated at 65 ° C. for 40 hours and concentrated in vacuo to provide the title compound as a white solid.

Compound 15

Compound C (2 mmol in 20 mL of toluene) was combined with 0.5 mL of diethylcarbamoyl chloride. The resultant solution was warmed at 80° C. for 40 hours. Solvents were removed in vacuo to reduce the volume by about half. The remaining material was loaded onto a 50 g silica gel column and eluted with a gradient from 1:1 ethyl acetate/hexanes to 100% ethyl acetate, to produce the title compound.

Compound 16

Compound 16 was prepared using the procedure for the preparation of Compound 15, except for substituting N-methyl-N-phenylcarbamoyl chloride for diethylcarbamoyl chloride. The resulting mixture was heated at 90° C. for 5 days. The crude material was purified by HPLC on a Waters Sunfire C8 column, eluting with a gradient of 35%/50%/87%/100% methanol in 0.1% ammonium acetate.

Compound 17

Compound 17 was prepared using the procedure for the preparation of Compound 15, except for substituting pyrrolidinecarbamoyl chloride for diethylcarbamoyl chloride. The resulting mixture was heated at 90° C. for 5 days. The crude material was purified by HPLC on a Waters Sunfire C8 column, eluting with a gradient of 35%/50%/87%/100% methanol in 0.1% ammonium acetate.

Compound 18

Compound D (10 mmol) in 50 mL of toluene) was combined with 4.44 mL (3.5 eq) of diethylcarbamoyl chloride. The resultant solution was warmed at 80° C. for 40 hours. The reaction mixture was poured onto a pad of 40 g of silica gel and eluted with 2×80 mL washes of ethyl acetate. The combined washes were concentrated in vacuo; the residue was loaded onto a 50 g silica gel column and eluted with a gradient from 1:1 ethyl acetate/hexanes to 100% ethyl acetate, to produce the title compound.

Compound 19

Compound 15 (2.12 g, 2 mmol) was dissolved in 40 mL of methanol and the mixture was warmed at 60° C. for three days. Solvents were removed in vacuo to isolate the title compound.

Compound 20

Compound 20 was prepared using the procedure for the preparation of Compound 15, except for substituting piperidinecarbamoyl chloride for diethylcarbamoyl chloride, and the mixture was heated at 60° C. for 65 hours. The crude product was purified by HPLC on a Waters Sunfire C8 column, eluting with a gradient of 5%/50%/87%/100% methanol in 0.1% ammonium acetate.

Compound 21

Compound 21 was prepared using the procedure for the preparation of Compound 15, except for substituting morpholinecarbamoyl chloride for diethylcarbamoyl chloride, and the mixture was heated at 80° C. for 40 hours. The crude product was purified by HPLC on a Waters Sunfire C8 column, eluting with a gradient of 5%/50%/87%/100% methanol in 0.1% ammonium acetate.

Compound 22

Triphosgene (30 mg, 0.1 mmol) was dissolved in 0.5 mL of toluene; 0.1 mL of diisopropylamine was added with stirring. The solution warmed, and a precipitate formed rapidly. After ten minutes, the resultant mixture was pushed through a syringe filter into a 4-ml vial. Compound C (0.2 mmol in 2 mL of toluene) was added, and the resultant mixture was warmed at 90° C. for 40 hours. Solvents were removed in vacuo to reduce the volume by about half; the remaining material was loaded onto a 10 g silica gel column and eluted with a gradient from 1:1 ethyl acetate/hexanes to 100% ethyl acetate.

Compound 23

Compound 23 was prepared using the procedure for the preparation of Compound 22, except for substituting di-n-butylamine for diisopropylamine.

Compound 24

Compound 24 was prepared using the procedure for the preparation of Compound 22, except for substituting diisobutylamine for diisopropylamine.

Compound 25

Compound 25 was prepared using the procedure for the preparation of Compound 22, except for substituting hexamethyleneimine for diisopropylamine.

Compound 26

Compound 26 was prepared using the procedure for the preparation of Compound 22, except for substituting dicyclohexylamine for diisopropylamine.

Compound 27

Compound 27 was prepared using the procedure for the preparation of Compound 15, except for substituting dimethylcarbamoyl chloride for diethylcarbamoyl chloride, and substituting Compound D for Compound C.

Compound 28

Compound 28 was prepared using the procedure for the preparation of Compound 22, except for substituting N-ethyl-N-butylamine for diisopropylamine, and substituting Compound D for Compound C. The resultant mixture was heated at 80° C. for 40 hours.

Compound 29

Compound 22 (30 mg) was dissolved in 1.5 mL of methanol and the mixture was warmed at 90° C. for 4 hours. The crude product was purified by HPLC on a Waters Sunfire C8 column, eluting with a gradient of 35% to 65% acetonitrile in 0.1% ammonium acetate.

Compound 30

Compound 23 (30 mg) was dissolved in 2 mL of methanol and the mixture was warmed at 70° C. for 65 hours. The crude product was purified by HPLC on a Waters Sunfire C8 column, eluting with a gradient of 35% to 65% acetonitrile in 0.1% aqueous ammonium acetate.

Compound 31

Compound 26 (54 mg) was dissolved in 1.5 mL of methanol and the mixture was warmed at 90° C. for 4 hours. Solvents were removed in vacuo to give the title compound as a white solid.

Compound 32

Compound D (1.5 mmol) in 10 mL toluene solution, was combined with morpholine-carbamoyl chloride (0.6 mL, 3.5 equivalents); the resultant mixture was heated overnight at 80° C. Solvents were removed in vacuo: the residue was chromatographed on a 50 g silica gel column, eluting with a gradient from 1:1 ethyl acetate/hexanes to 100% ethyl acetate, to produce the title compound.

Compound 33

Compound C (1.5 mmol) in 10 mL toluene solution, was combined with 2,4-difluorobenzyl bromide (2.0 equivalents) and 30 mg of tetra-n-butylammonium iodide. The resultant mixture was heated at 90° C. for 3 days. Solvents were removed in vacuo; the residue was chromatographed on a 50 g silica gel column, eluting with a gradient from 1:1 ethyl acetate/hexanes to 100% ethyl acetate. The title compound was collected as a white solid.

Compound 34

Compound F (1.5 mmol) in 10 mL toluene solution, was combined with morpholine-carbamoyl chloride (0.6 mL, 3.5 equivalents); the resultant mixture was heated at 90° C. for 8 hours. Solvents were removed in vacuo; the residue was chromatographed on a 100 g silica gel column, eluting with a gradient from 1:1 ethyl acetate/hexanes to 100% ethyl acetate, to produce the title compound.

Compound 35

Compound F (1.5 mmol) in 10 mL toluene solution, was combined with 2,4-difluorobenzyl bromide (2.0 equivalents) and 100 mg of tetra-n-butylammonium iodide. The resultant mixture was heated at 90° C. for 3 days. Solvents were removed in vacuo: the residue was chromatographed on a 50 g silica gel column, eluting with a gradient from 1:1 ethyl acetate/hexanes to 100% ethyl acetate. The title compound was collected as a white solid.

Compound 36

Compound 21 (0.92 g) was dissolved in 20 mL of methanol; 20 mg of solid sodium bicarbonate was added, and the resultant mixture was warmed at 50° C. for 40 hours. Solvents were removed in vacuo; the residue was taken up in ethyl acetate and filtered through a syringe filter. The solution was concentrated in vacuo to give the title compound.

Compound 37

Compound 33 (0.54 g) was dissolved in 20 mL of methanol; 20 mg of solid sodium bicarbonate was added, and the resultant mixture was warmed at 70° C. for 40 hours. Solvents were removed in vacuo; the residue was taken up in ethyl acetate and filtered through a syringe filter. The solution was concentrated in vacuo to give the title compound.

Compound 38

Compound 1 (1.05 g, 1 mmol) was dissolved in methanol (20 mL) and heated at 65° C. for 40 hours. Solvents were removed in vacuo to provide the title compound.

Compound 39

Step 1: The intermediate was prepared using the procedure for the preparation of Compound 1, except for substituting 4-methoxybenzyl bromide for benzyl bromide.

Step 2: Compound 39 was prepared using the procedure for the preparation of Compound 38, except for substituting the intermediate obtained from Step 1 for Compound 1. The crude product was purified by HPLC on a Waters Sunfire C8 column, eluting with a gradient of 35%/65%/87%/100% acetonitrile in 0.1% ammonium acetate.

Compound 40

Compound 19 (200 mg) was combined with 20 mg of 10% palladium-on-carbon in 12 mL of methanol; the resultant mixture was first purged under nitrogen, then exchanged for a balloon of hydrogen gas. After stirring at ambient temperature for 4 hours, the balloon was removed, the mixture was purged with nitrogen and concentrated in vacuo. The residue was taken up in ethyl acetate and passed through a 0.45 micron filter to remove the catalyst. The resultant clear solution was concentrated in vacuo to give the title compound.

Compound 41

Compound 18 (200 mg) was combined with 20 mg of 10% palladium-on-carbon in 12 mL of methanol; the resultant mixture was first purged under nitrogen, then exchanged for a balloon of hydrogen gas. After stirring at ambient temperature for 4 hours, the balloon was removed, the mixture was purged with nitrogen and concentrated in vacuo. The residue was taken up in ethyl acetate and passed through a 0.45 micron filter to remove the catalyst. The resultant clear solution was concentrated in vacuo to give the title compound.

Compound 42

Compound J (0.83 mmol) was combined with 4-fluorobenzyl bromide (1.5 eq) and 0.1 eq of tetra-n-butylammonium iodide. The resultant mixture was heated at 90° C. for two days. The mixture was concentrated in vacuo; the residue was chromatographed on silica gel, eluting with a gradient of 20-100% ethyl acetate/hexanes. Fractions containing the target compound (as its 2'-acetate) were combined and concentrated in vacuo. The residue was dissolved in 15 mL of methanol; 20 mg of solid sodium bicarbonate was added, and the resultant solution was stirred overnight at 40° C. The mixture was concentrated in vacuo; the residue was chromatographed on silica gel, eluting with a gradient of 50-100% ethyl acetate/hexanes. The title compound (112 mg) was isolated as a white foam.

Compound 43

Compound J (0.83 mmol) was combined with 2,4-difluorobenzyl bromide (1.5 eq) and 0.1 eq of tetra-n-butylammonium iodide. The resultant mixture was heated at 90° C. for two days. The mixture was concentrated in vacuo; the residue was chromatographed on silica gel, eluting with a gradient of 20-100% ethyl acetate/hexanes. Fractions containing the target compound (as its 2'-acetate) were combined and concentrated in vacuo. The residue was dissolved in 15 mL of methanol; 20 mg of solid sodium bicarbonate was added, and the resultant solution was stirred overnight at 40° C. The mixture was concentrated in vacuo; the residue was chromatographed on silica gel, eluting with a gradient of 50-100% ethyl acetate/hexanes. The title compound (50 mg) was isolated as a white foam.

Compound 44

Compound 15 (200 mg) was dissolved in 1 mL of dry pyridine; 0.2 mL of propionic anhydride was added, and the resulting solution was stirred at ambient temperature for 2 hours. Reaction was quenched by the addition of 0.5 mL of methanol; the mixture was stirred for 10 minutes, then concentrated in vacuo. The residue was chromatographed on a 10 g silica gel column, eluting with a solvent gradient from 20% ethyl acetate/hexanes to ethyl acetate. A pure sample (20 mg) selected from a middle cut of the major peak was confirmed to be the title compound.

Compound 45

Compound 44 (60 mg) was dissolved in 5 mL of methanol and heated at reflux for 12 hours. Sovents were removed in vacuo; the residue was purified by HPLC on a Waters Sunfire C8 column, eluting with a gradient of 50% to 100% acetonitrile in 0.1% ammonium acetate. The title compound was isolated as a white solid (23 mg).

Compound 46

The title compound was isolated as a minor fraction (5 mg) from HPLC purification of the mixture generated during the reaction to produce Compound 45.

Compound 47

Compound 3 (435 mg) was dissolved in 2 mL of dry pyridine; 0.4 mL of propionic anhydride was added, and the resulting solution was stirred at ambient temperature for 2 hours. Reaction was quenched by the addition of 0.5 mL of methanol; the mixture was stirred for 10 minutes, then concentrated in vacuo. The residue was chromatographed on a 40g silica gel column, eluting with a solvent gradient from 20% ethyl acetate/hexanes to ethyl acetate. A pure sample (13 mg) selected from a middle cut of the major peak was confirmed to be the title compound.

Compound 48

Compound 47 (77 mg) was dissolved in 2 mL of methanol and warmed at 60° C. for 5 days. Sovents were removed in vacuo; the residue was purified by HPLC on a Waters Sunfire C8 column, eluting with a gradient of 50% to 100% acetonitrile in 0.1% ammonium acetate. The title compound was isolated as a white solid (11 mg).

Compound 49

Compound 15 (400 mg) was dissolved in 2 mL of dry pyridine; 0.4 mL of acetic anhydride was added, and the resulting solution was stirred at ambient temperature for 3 hours. Reaction was quenched by the addition of 0.5 mL of methanol; the mixture was stirred for 10 minutes, then concentrated in vacuo. The residue was chromatographed on a 10 g silica gel column, eluting with a solvent gradient from 20% ethyl acetate/hexanes to ethyl acetate. A set of mixed fractions were concentrated in vacuo and re-purified by HPLC on a Waters Sunfire C8 column, eluting with a gradient of 50% to 100% acetonitrile in 0.1% ammonium acetate. The title compound was isolated as a white solid (18.4 mg).

Compound 50

Compound 49 (330 mg) was dissolved in 5 mL of methanol and warmed at 70° C. for 3 days. Sovents were removed in vacuo; the residue was purified by chromatography on a 12-g silica gel column, eluting with a gradient from 60% ethyl acetate in hexanes to 100% ethyl acetate. The resultant impure fractions were re-purified by HPLC on a Waters Sunfire C8 column, eluting with a gradient of 50% to 100% acetonitrile in 0.1% ammonium acetate. The title compound was isolated as a white solid (64.9 mg).

Compound 51

Compound 15 (400 mg) was dissolved in 2 mL of dry pyridine; 0.4 mL of isobutyric anhydride was added, and the resulting solution was stirred at ambient temperature for 24 hours. Reaction was quenched by the addition of 0.5 mL of methanol; the mixture was stirred for 10 minutes, then concentrated in vacuo. The residue was chromatographed on a 12 g silica gel column, eluting with a solvent gradient from 20% ethyl acetate/hexanes to ethyl acetate. The resultant product (350 mg) was dissolved in 5 mL of methanol and warmed at 70 C for 3 days. Sovents were removed in vacuo; the residue was purified by chromatography on a 12-g silica gel column, eluting with a gradient from 20% ethyl acetate in hexanes to 100% ethyl acetate. The resultant impure sample was re-purified by HPLC on a Waters Sunfire C8 column, eluting with a slow gradient of 2% to 100% acetonitrile in 0.1% ammonium acetate. The title compound was isolated as a white solid (88.5 mg).

Compound 52

Compound 3 (400 mg) was dissolved in 2 mL of dry pyridine; 0.1 mL of acetic anhydride was added, and the resulting solution was stirred at ambient temperature for 4 hours. Reaction was quenched by the addition of 0.5 mL of methanol; the mixture was stirred for 10 minutes, then concentrated in vacuo. The residue was chromatographed on a 12g silica gel column, eluting with a solvent gradient from 20% ethyl acetate/hexanes to ethyl acetate. A pure sample (17 mg) selected from a middle cut of the major peak was confirmed to be the title compound.

Compound 53

Compound 52 (180 mg) was dissolved in 5 mL of methanol and warmed at 70° C. for 3 days. Sovents were removed in vacuo; the residue was purified by chromatography on a 12-g silica gel column, eluting with a gradient from 60% ethyl acetate in hexanes to 100% ethyl acetate. The title compound was isolated as a white solid (141 mg).

Compound 54

Compound 3 (400 mg) was dissolved in 2 mL of dry pyridine; 0.4 mL of isobutyric anhydride was added, and the resulting solution was stirred at ambient temperature for 20 hours. Reaction was quenched by the addition of 0.5 mL of methanol; the mixture was stirred for 10 minutes, then concentrated in vacuo. The residue was chromatographed on a 12 g silica gel column, eluting with a solvent gradient from 60% ethyl acetate/hexanes to ethyl acetate. A pure sample (6.4 mg) selected from a middle cut of the major peak was confirmed to be the title compound.

Compound 55

Compound 54 (190 mg) was dissolved in 5 mL of methanol and warmed at 60° C. for 4 days. Sovents were removed in vacuo; the residue was purified by chromatography on a 12-g silica gel column, eluting with a gradient from 60% ethyl acetate in hexanes to 100% ethyl acetate. The title compound was isolated as a white solid (140 mg).

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The

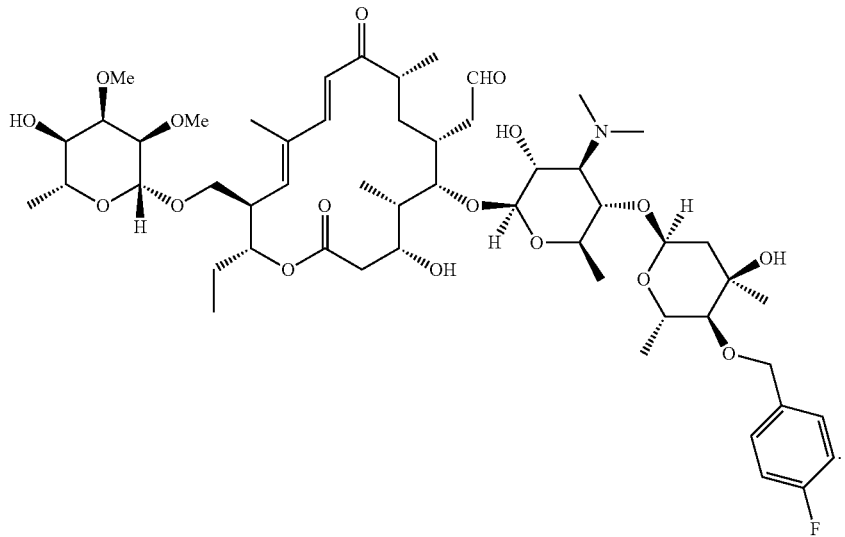

What is claimed is:

1. A method of preventing or treating filariasis in a subject in need thereof, comprising:
   administering to the subject a therapeutically effective amount of tylosin A or a salt thereof.

2. The method of claim 1, wherein the subject is a human.

3. The method of claim 1, wherein the filariasis is lymphatic filariasis or subcutaneous filariasis.

4. The method of claim 1, wherein the filariasis is caused by *Onchocerca volvulus, Wuchereria bancrofti, Brugia malayi, Brugia timori,* or *Dirofilaria immitis.*

5. A method of preventing or treating filariasis caused by *Onchocerca volvulus, Wuchereria bancrofti, Brugia malayi, Brugia timori,* or *Dirofilaria immitis* in a subject in need thereof, comprising:
   administering to the subject a therapeutically effective amount of a compound of Formula (I):

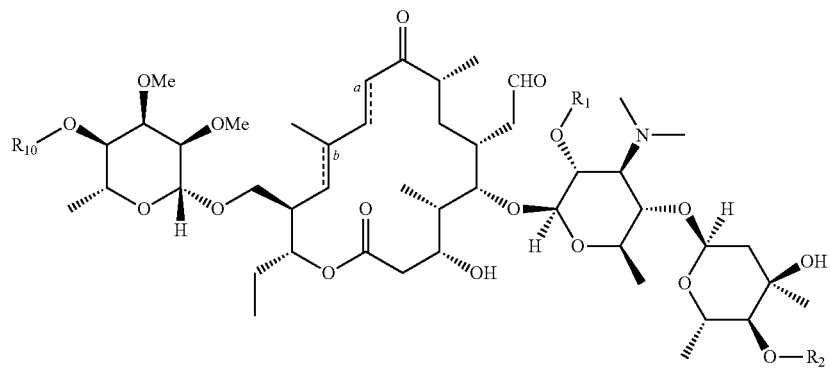

(I)

or a salt thereof, wherein:

$R_1$ represents hydrogen or —C(O)$R_3$, wherein $R_3$ represents an optionally substituted $C_1$-$C_6$-alkyl or $C_1$-$C_6$-haloalkyl;

$R_2$ represents —C(O)C($R_4$)($R_5$)($R_6$), wherein $R_4$ is selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl $C_1$-$C_4$-alkyl; and each of $R_5$ and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl -$C_1$-$C_4$-alkyl; or $R_2$ represents —C(O)N($R_7$)($R_8$), wherein each of $R_7$ and $R_8$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl -$C_1$-$C_4$-alkyl, or $R_7$ and $R_8$ together with the nitrogen atom to which they are attached form an optionally substituted saturated or partially saturated heterocyclic ring; or $R_2$ represents —CH$_2$-$A_1$, wherein $A_1$ represents a 6-to 10-membered aryl or a 5-to 10-membered heteroaryl and $A_1$ is unsubstituted or substituted with one or more $R_A$, wherein each $R_A$ is independently selected from the group consisting of halogen, $C_1$-$C_6$-alkyl, $C_1$-$C_6$-haloalkyl, and —O—$R_9$, where $R_9$ represents $C_1$-$C_6$-alkyl;

$R_{10}$ represents hydrogen or —C(O)$R_{11}$, wherein $R_{11}$ represents an optionally substituted $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, or $C_3$-$C_8$-cycloalkyl —$C_1$-$C_4$-alkyl; and each of a and b independently represents either a single bond or a double bond.

6. The method of claim 5, wherein $R_{10}$ is —C(O)$R_{11}$.

7. The method of claim 6, wherein $R_{11}$ is $C_1$-$C_6$-alkyl.

8. The method of claim 6, wherein both a and b represent a double bond and wherein $R_1$ is —C(O)CH$_3$, $R_2$ is —C(O)N(CH$_2$CH$_3$)$_2$, and $R_{11}$ is —CH$_2$CH$_3$; $R_1$ is hydrogen, $R_2$ is —C(O)N(CH$_2$CH$_3$)$_2$, and $R_{11}$ is —CH$_2$CH$_3$; $R_1$ is —C(O)CH$_2$CH$_3$, $R_2$ is —C(O)N(CH$_2$CH$_3$)$_2$, and $R_{11}$ is —CH$_2$CH$_3$; $R_1$ is —C(O)CH$_3$, $R_2$ is

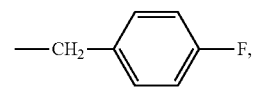

and $R_{11}$ is —CH$_2$CH$_3$; $R_1$ is hydrogen, $R_2$ is

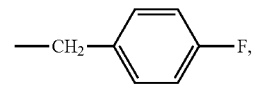

and $R_{11}$ is —CH$_2$CH$_3$; $R_1$ is —C(O)CH$_3$, $R_2$ is —C(O)N(CH$_2$CH$_3$)$_2$, and $R_{11}$ is —CH$_3$; $R_1$ is hydrogen, $R_2$ is —C(O)N(CH$_2$CH$_3$)$_2$, and $R_{11}$ is —CH$_3$; $R_1$ is hydrogen, $R_2$ is —C(O)N(CH$_2$CH$_3$)$_2$, and $R_{11}$ is —CH(CH$_3$)$_2$; $R_1$ is —C(O)CH$_3$, $R_2$ is

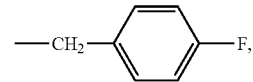

and R$_{11}$ is —CH$_3$; R$_1$ is hydrogen, R$_2$ is

—CH$_2$—⟨C$_6$H$_4$⟩—F, and R$_{11}$ is —CH$_3$; R$_1$ —C(O)CH$_3$, R$_2$ is

—CH$_2$—⟨C$_6$H$_4$⟩—F, and R$_{11}$ is —CH(CH$_3$)$_2$; or R$_1$ is hydrogen, R$_2$ is

—CH$_2$—⟨C$_6$H$_4$⟩—F, and R$_{11}$ is —CH(CH$_3$)$_2$.

9. The method of claim 5, wherein the compound has a structure corresponding to Formula (I -1):

(I-1)

[structure of macrolide compound]

or a salt thereof.

10. The method of claim 9, wherein R$_1$ is hydrogen.

11. The method of claim 9, wherein R$_1$ is —C(O)R$_3$.

12. The method of claim 11, wherein R$_3$ is methyl, isopropyl, or n-butyl.

13. The method of claim 9, wherein R$_2$ is —C(O)N(R$_7$)(R$_8$) and each of R$_7$ and R$_8$ are independently selected from the group consisting of C$_1$-C$_6$-alkyl, aryl, and C$_3$-C$_8$-cycloalkyl, or R$_7$ and R$_8$ together with the nitrogen atom to which they are attached form an optionally substituted saturated or partially saturated heterocyclic ring.

14. The method of claim 13, wherein the heterocyclic ring is a pyrrolidine, a piperidine, an azepane, or a morpholine.

15. The method of claim 9, wherein R$_2$ is —CH$_2$-A$_1$ and A$_1$ is an unsubstituted phenyl or a phenyl substituted with one or more R$_4$.

16. The method of claim 15, wherein R$_4$ is halogen.

17. The method of claim 9, wherein both a and b represent a double bond.

18. The method of claim 17, wherein R$_1$ is —C(O)CH$_3$ and R$_2$ is

—CH$_2$—⟨C$_6$H$_5$⟩;

R$_1$ is —C(O)CH$_3$ and R$_2$ is

—CH$_2$—⟨C$_6$H$_4$⟩—CF$_3$;

R$_1$ is —C(O)CH$_3$ and R$_2$ is

—CH$_2$—⟨C$_6$H$_4$⟩—F;

R$_1$ is —C(O)CH$_3$ and R$_2$ is

—CH$_2$—⟨C$_6$H$_4$⟩—Cl;

R$_1$ is —C(O)CH(CH$_3$)$_2$ and R$_2$ is

—CH$_2$—⟨C$_6$H$_5$⟩;

R$_1$ is —C(O)CH(CH$_3$)$_2$ and R$_2$ is

—CH$_2$—⟨C$_6$H$_3$(F)⟩—F;

R₁ is —C(O)CH(CH₃)₂ and R₂ is

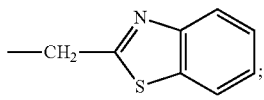

R₁ is —C(O)CH(CH₃)₂ and R₂ is

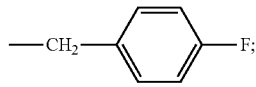

R₁ is —C(O)CH(CH₃)₂ and R₂ is

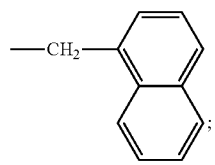

R₁ is hydrogen and R₂ is

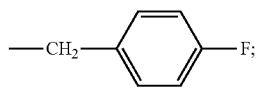

R₁ is —C(O)(CH₂)₃CH₃ and R₂ is

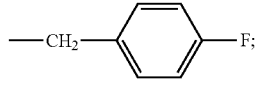

R₁ is —C(O)CH₃ and R₂ is —C(O)C(CH₃)₃; R₁ is —C(O)CH(CH₃)₂ and R₂ is —C(O)C(CH₃)₃; R₁ is hydrogen and R₂ is —C(O)C(CH₃)₃; R₁ is —C(O)CH₃ and R₂ is —C(O)N(CH₂CH₃)₂; R₁ is —C(O)CH₃ and R₂ is —C(O)N(CH₃)(C₆H₅); R₁ is —C(O)CH₃ and R₂ is

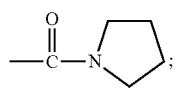

R₁ is —C(O)CH(CH₃)₂ and R₂ is —C(O)N(CH₂CH₃)₂; R₁ is hydrogen and R₂ is —C(O)N(CH₂CH₃)₂; R₁ is —C(O)CH₃ and R₂ is

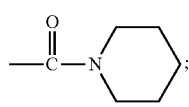

R₁ is —C(O)CH₃ and R₂ is

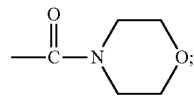

R₁ is —C(O)CH₃ and R₂ is —C(O)N(CH(CH₃)₂)₂; R₁ is —C(O)CH₃ and R₂ is —C(O)N((CH₂)₃CH₃)₂; R₁ is —C(O)CH₃ and R₂ is —C(O)N((CH₂CHCH₃)₂)₂; R₁ is —C(O)CH₃ and R₂ is

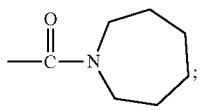

R₁ is —C(O)CH₃ and R₂ is

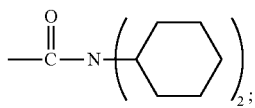

R₁ is —C(O)CH(CH₃)₂ and R₂ is —C(O)N(CH₃)₂; R₁ is —C(O)CH(CH₃)₂ and R₂ is —C(O)N(CH₂CH₃)((CH₂)₃CH₃); R₁ is hydrogen and R₂ is —C(O)N(CH(CH₃)₂)₂; R₁ is hydrogen and R₂ is —C(O)N((CH₂)₃CH₃)₂; R₁ is H and R₂ is

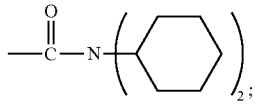

R₁ is —C(O)CH(CH₃)₂ and R₂ is

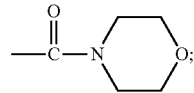

R₁ is —C(O)CH₃ and R₂ is

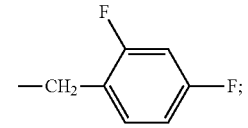

R₁ is —C(O)(CH₂)₃(CH₃) and R₂ is

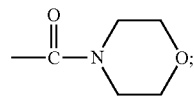

$R_1$ is —C(O)(CH$_2$)$_3$(CH$_3$) and $R_2$ is

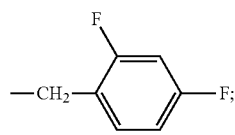

$R_1$ is hydrogen and $R_2$ is

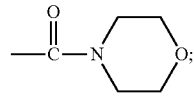

$R_1$ is hydrogen and $R_2$ is

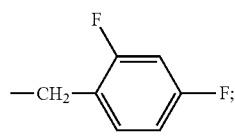

$R_1$ is hydrogen and $R_2$ is

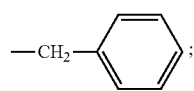

or $R_1$ is hydrogen and $R_2$ is

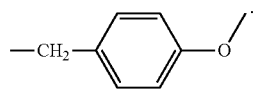

19. The method of claim 17, wherein $R_1$ is hydrogen and $R_2$ is

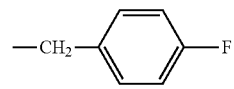

or —C(O)N(CH$_2$CH$_3$)$_2$.

20. The method of claim 9, wherein both a and b represent a single bond.

21. The method of claim 20, wherein $R_1$ is hydrogen and $R_2$ is —C(O)N(CH$_2$CH$_3$)$_2$; $R_1$ is —C(O)CH(CH$_3$)$_2$ and $R_2$ is —C(O)N(CH$_2$CH$_3$)$_2$; $R_1$ is hydrogen and $R_2$ is

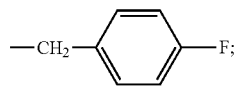

or $R_1$ is hydrogen and $R_2$ is

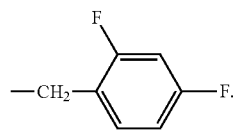

22. The method of claim 9, wherein $R_2$ is —C(O)N($R_7$)($R_8$) and both of $R_7$ and $R_8$ are $C_1$-$C_6$ alkyl.

23. The method of claim 17, wherein $R_1$ is hydrogen, $R_2$ is —C(O)N($R_7$)($R_8$) and both of $R_7$ and $R_8$ are —CH$_2$CH$_3$.

24. A method of preventing or treating filariasis caused by *Onchocerca volvulus, Wuchereria bancrofti, Brugia malayi, Brugia timori*, or *Dirofilaria immitis* in a subject in need thereof, comprising:

administering to the subject a therapeutically effective amount of a compound of Formula (III):

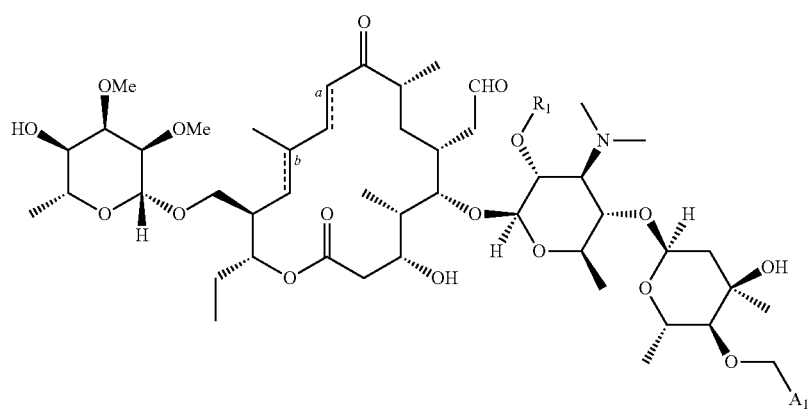

or a salt thereof, wherein:

R$_1$ represents hydrogen or —C(O)R$_3$, where R$_3$ represents C$_1$-C$_6$-alkyl;

A$_1$ represents a 6 -to 10-membered aryl or a 5 -to 10-membered heteroaryl and A$_1$ is unsubstituted or substituted with one or more R$_4$, wherein each R$_4$ is independently selected from the group consisting of halogen, C$_1$-C$_6$-alkyl, C$_1$-C$_6$-haloalkyl, and —O—R$_9$, where R$_9$ represents C$_1$-C$_6$-alkyl; and each of a and b independently represents either a single bond or a double bond.

25. The method of claim 24, wherein R$_1$ is hydrogen.

26. The method of claim 24, wherein A$_1$ is phenyl substituted with one R$_4$.

27. The method of claim 26, wherein R$_4$ is halogen.

28. The method of claim 24, wherein the compound has a structure corresponding to: